(12) United States Patent
Healy

(10) Patent No.: US 11,053,541 B2
(45) Date of Patent: Jul. 6, 2021

(54) SYSTEMS AND METHODS FOR SEQUENCING IN EMULSION BASED MICROFLUIDICS

(71) Applicant: Bio-Rad Laboratories, Inc., Hercules, CA (US)

(72) Inventor: John Healy, Acton, MA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 972 days.

(21) Appl. No.: 15/699,557

(22) Filed: Sep. 8, 2017

(65) Prior Publication Data

US 2018/0073074 A1 Mar. 15, 2018

Related U.S. Application Data

(63) Continuation of application No. 14/290,867, filed on May 29, 2014, now Pat. No. 9,809,851.

(60) Provisional application No. 61/828,582, filed on May 29, 2013.

(51) Int. Cl.
*C12Q 1/6874* (2018.01)
*G16B 30/00* (2019.01)
*C12N 15/10* (2006.01)
*G16B 20/00* (2019.01)

(52) U.S. Cl.
CPC ....... *C12Q 1/6874* (2013.01); *C12N 15/1075* (2013.01); *G16B 30/00* (2019.02); *G16B 20/00* (2019.02)

(58) Field of Classification Search
None
See application file for complete search history.

(56) References Cited

U.S. PATENT DOCUMENTS

| | | |
|---|---|---|
| 8,528,589 B2 | 9/2013 | Miller et al. |
| 8,535,889 B2 | 9/2013 | Larson et al. |
| 9,555,411 B2 | 1/2017 | Kiani et al. |
| 2008/0166720 A1 | 7/2008 | Hsieh et al. |
| 2009/0081675 A1 | 3/2009 | Colston et al. |
| 2011/0053798 A1 | 3/2011 | Hindson et al. |
| 2011/0151578 A1 | 6/2011 | Abate et al. |
| 2011/0218123 A1 | 9/2011 | Weitz et al. |
| 2011/0250597 A1 | 10/2011 | Larson et al. |
| 2011/0267457 A1 | 11/2011 | Weitz et al. |
| 2012/0015822 A1 | 1/2012 | Weitz et al. |
| 2012/0132288 A1 | 5/2012 | Weitz et al. |
| 2012/0208241 A1 | 8/2012 | Link |
| 2012/0219947 A1 | 8/2012 | Yurkovetsky et al. |
| 2012/0220494 A1 | 8/2012 | Samuels et al. |
| 2012/0222748 A1 | 9/2012 | Weitz et al. |
| 2012/0302448 A1 | 11/2012 | Hutchison et al. |
| 2012/0309002 A1 | 12/2012 | Link |
| 2014/0354795 A1 | 12/2014 | Tracy et al. |
| 2015/0065396 A1 | 3/2015 | Kiani et al. |

FOREIGN PATENT DOCUMENTS

| | | |
|---|---|---|
| CN | 101240341 A | 8/2008 |
| EP | 2364774 A2 | 9/2011 |
| EP | 2662135 A2 | 11/2013 |
| WO | 2000-040758 A2 | 7/2000 |
| WO | 2007/081385 A2 | 7/2007 |
| WO | 2007/081387 A1 | 7/2007 |
| WO | 2007-133710 A2 | 11/2007 |
| WO | 2009/085215 A1 | 7/2009 |
| WO | 2012/078710 A1 | 6/2012 |
| WO | 2012/135201 A1 | 10/2012 |
| WO | 2012/135259 A1 | 10/2012 |
| WO | 2012/135327 A1 | 10/2012 |
| WO | 2013/095737 A2 | 6/2013 |
| WO | 2013/122826 A1 | 8/2013 |
| WO | 2013/165748 A1 | 11/2013 |
| WO | 2014/043388 A1 | 3/2014 |
| WO | 2014/093976 A1 | 6/2014 |
| WO | 2014/117088 A1 | 7/2014 |
| WO | 2014/176599 A1 | 10/2014 |

OTHER PUBLICATIONS

Partial European Search Report dated Nov. 23, 2016 in EP Application 14804752.5 all pages.
Supplementary Partial European Search Report dated Dec. 5, 2016 in EP 14804752, 7 pages.
Extended European Search Report dated Apr. 28, 2017 in EP 14804752, 12 pages.
International Search Report and Written Opinion of PCT/US2014/040082 dated Dec. 4, 2014, 26 pages.
Abate, et al.; "High throughput injection with microfluidics using picoinjectors"; Proceedings of the National Academy of Sciences USA; vol. 107; 2010; pp. 19163-19166.
Anthony, S.. "Harvard Cracks DNA Storage, Crams 700 Terabytes of Data into a Single Gram," Extreme Tech Website, Aug. 17, 2012, 3 pages, accessed online, <http://www.extremetech. com/extreme/134672.

(Continued)

*Primary Examiner* — John S Brusca
(74) *Attorney, Agent, or Firm* — Kilpatrick Townsend and Stockton LLP

(57) ABSTRACT

Methods, libraries, and kits for nucleotide sequencing are provided. For example, methods can comprise providing a plurality of partitions, the partitions comprising a set of two or more different primers and a target nucleic acid, wherein different partitions contain different sets of primers with a majority of primers in the sets being common with a different primer set but wherein any two different partitions having a common primer contain no more than one common primer; and hybridizing the target nucleic acid to the primers in the reaction partitions under conditions in which fully complementary primers hybridize to the target sequence and primers that are not fully complementary do not hybridize to the target nucleic acid.

22 Claims, 27 Drawing Sheets
(18 of 27 Drawing Sheet(s) Filed in Color)
Specification includes a Sequence Listing.

(56) References Cited

OTHER PUBLICATIONS

Arneson, Nona, et al., "Whole-Genome Amplification by Degenerate Oligonuleotide Primed PCR (DOP-PCR)," Cold Spring Harbor Protocols, Jan. 2008, vol. 3, No. 1, pp. 1-6.

Calero, O., et al., "Apolipoprotein E genotyping method by Real Time PCR. a fast and cost-effective alternative to the TaqMan<(>R) and FRET assays," Journal of Neuroscience Methods, Oct. 15, 2009, vol. 183, No. 2, pp. 238-240.

Fitzgerald, J, "Advances in RainDance Sequence Enrichment Technology and Applications in Cancer Research," RainDance Technologies Presentation, Mar. 17, 2011, 37 pages, accessed online, http://gqinnovationcenter.com/documents/rendezVous/7-Fitzgerald RDT .pdf>.

Miller, Jason, R., et al., "Assembly Algorithms for Next-Generation Sequencing Data," Genomics, 2010, vol. 95; pp. 315-327.

Skiena, S. et al.; "Restricting SBH ambiguity via restriction enzymes"; Discrete Applied Mathematics; Feb. 9, 2007; vol. 155, No. 6-7; pp. 857-867; Elsevier Science, Amsterdam, NL.

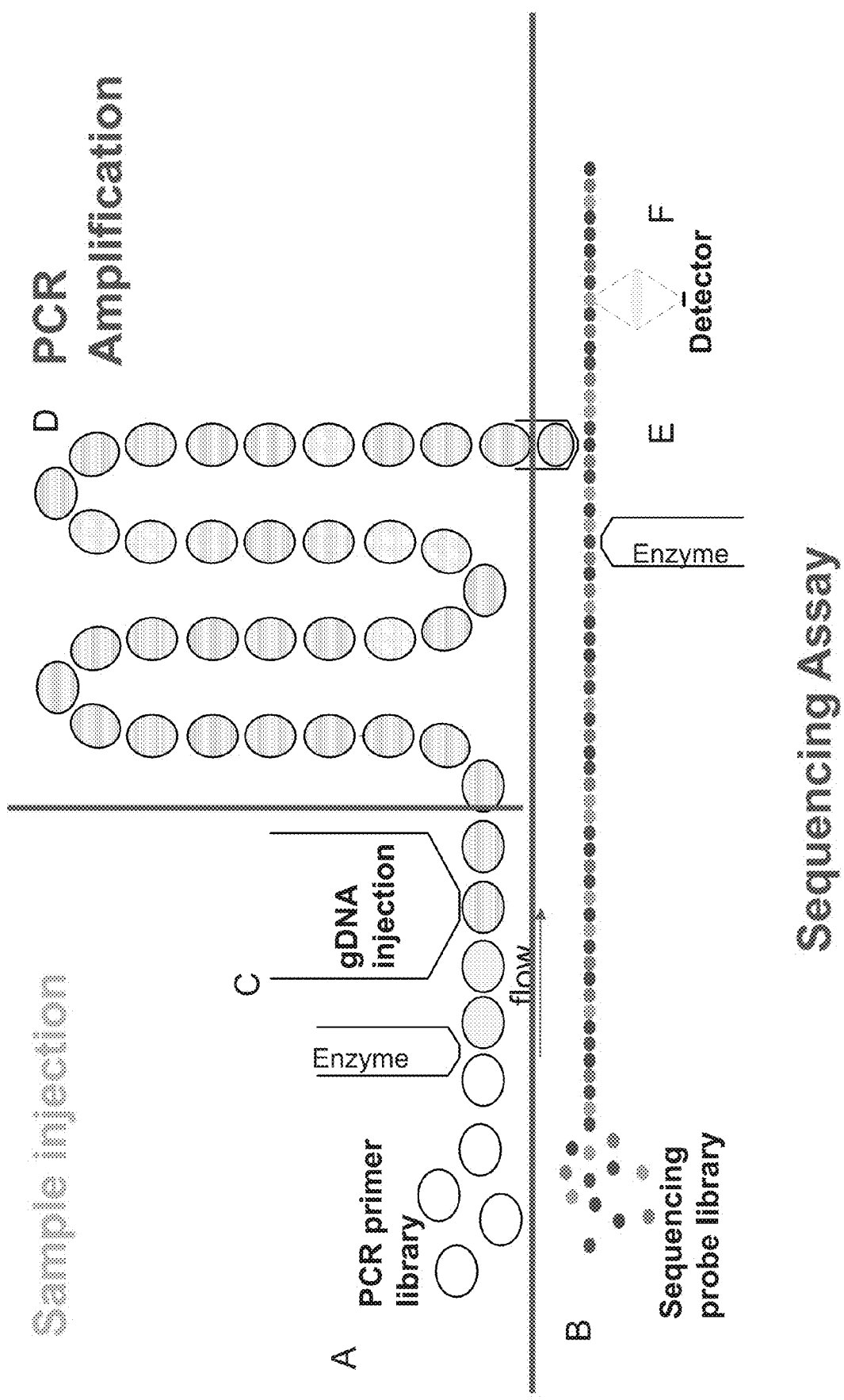
Figure 1: Microfluidic Workflow

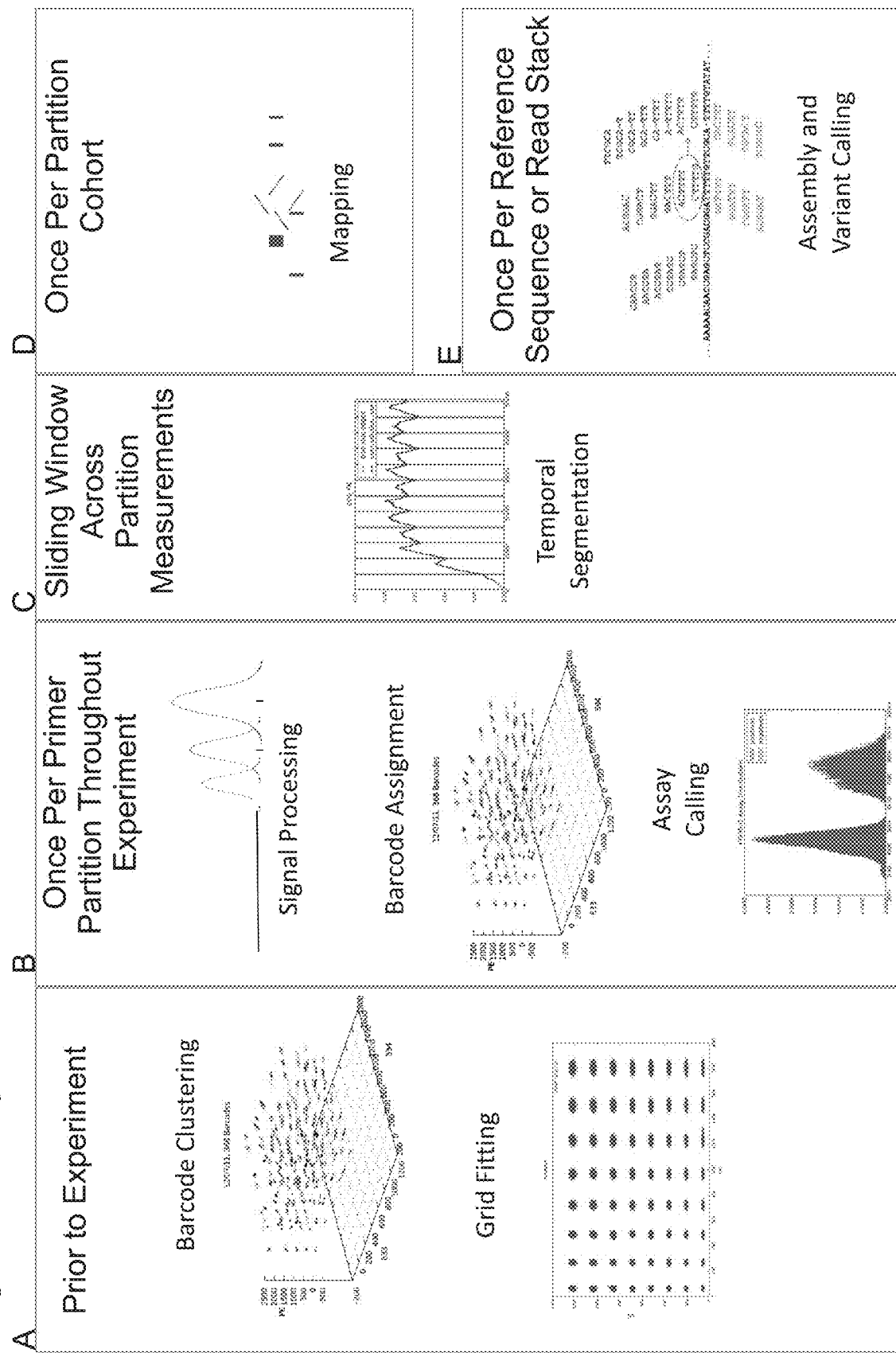
Figure 2: Analysis Software Architecture

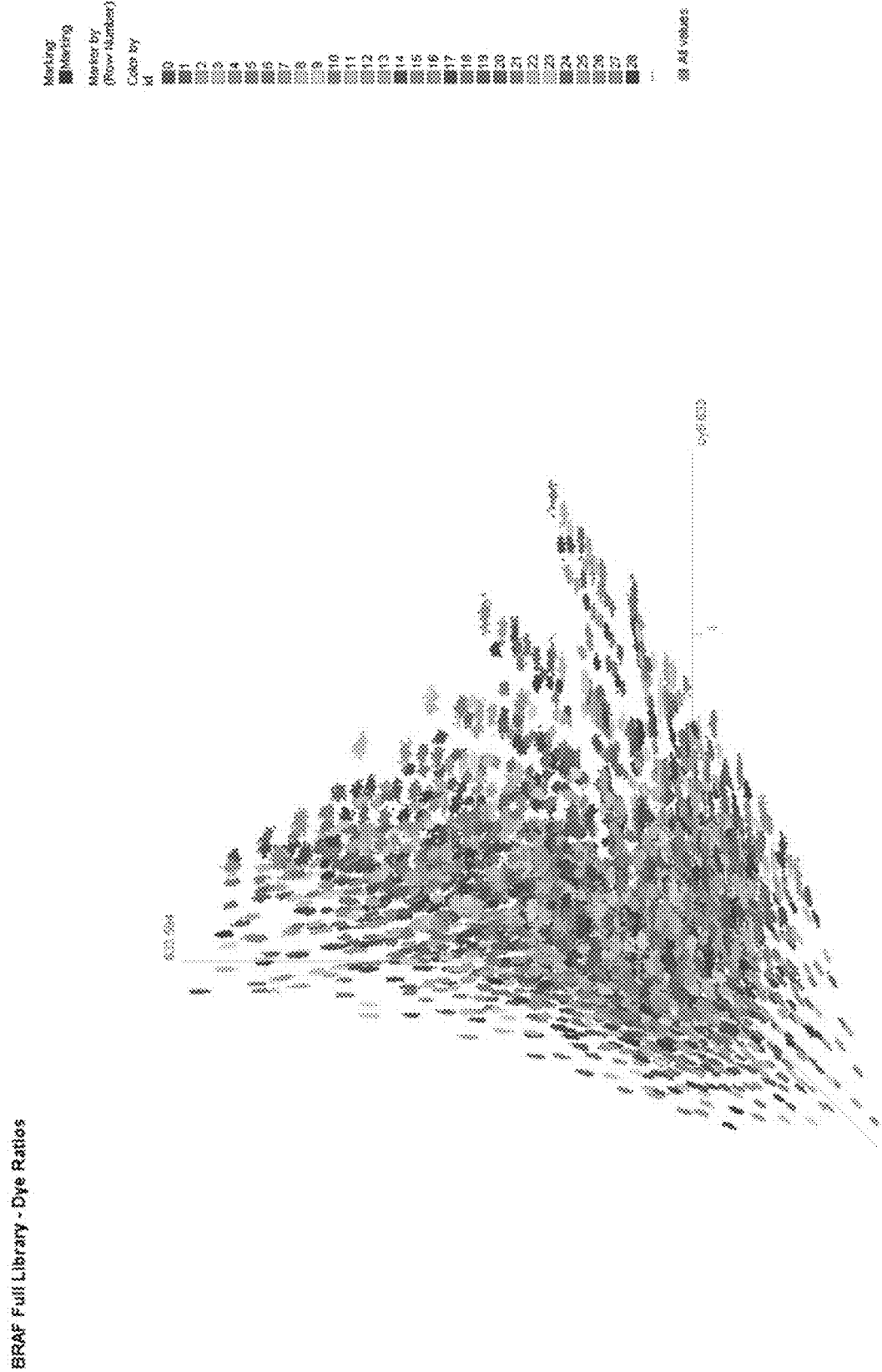
Figure 3A: Four Dimensional Dye Profile Clustering
BRAF Full Library - Dye Ratios

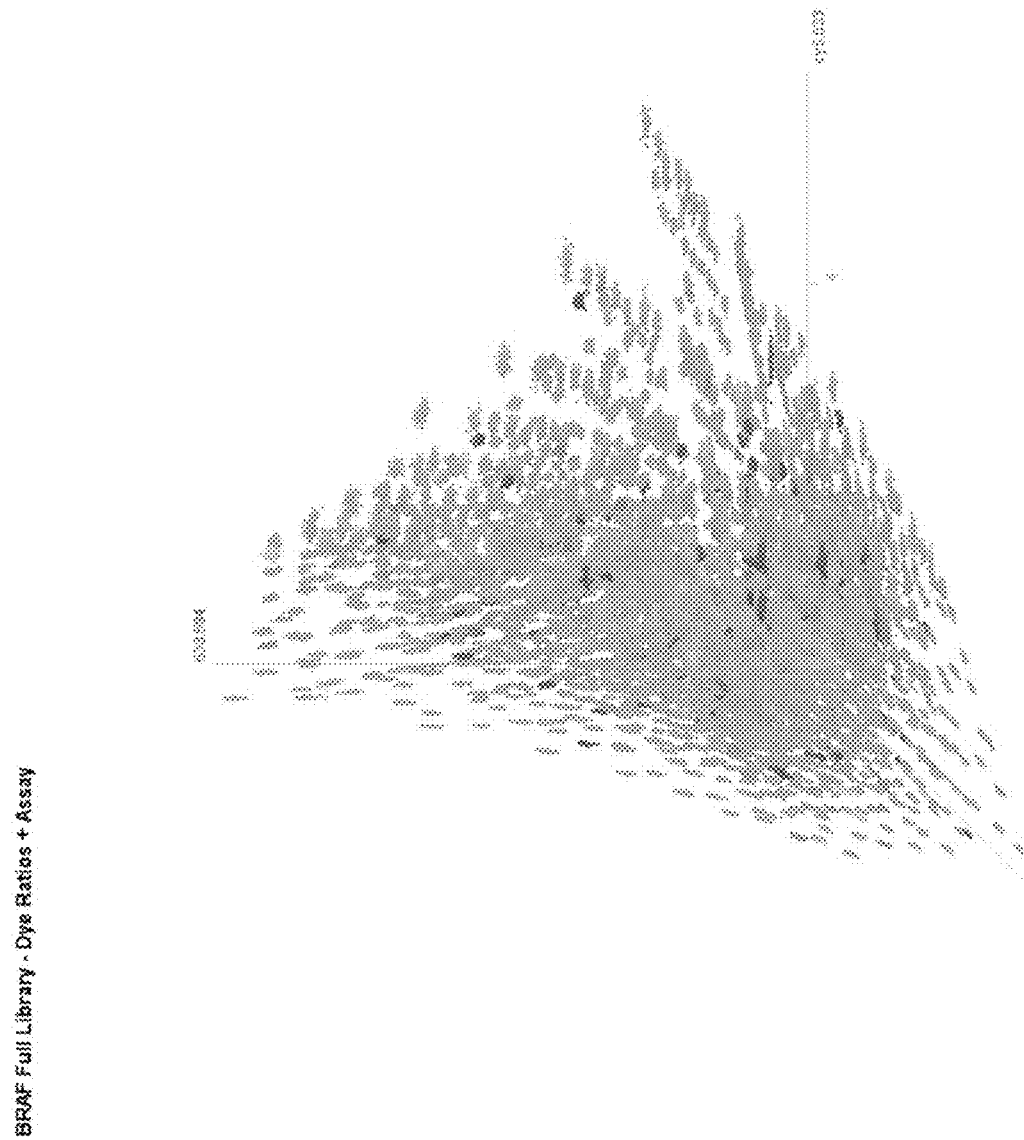
Figure 3B: Four Dimensional Dye Profiles – Colored by Assay Intensity

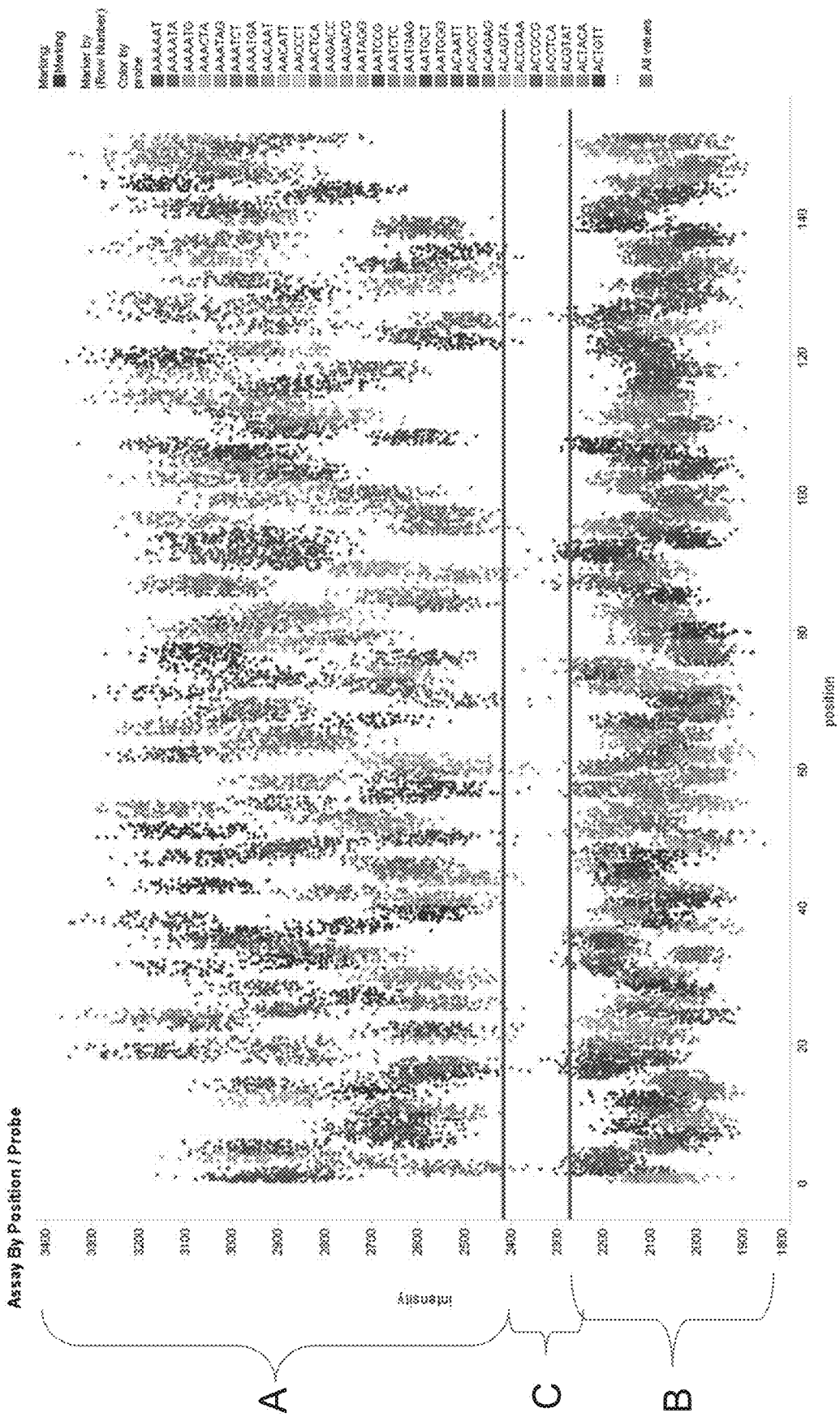

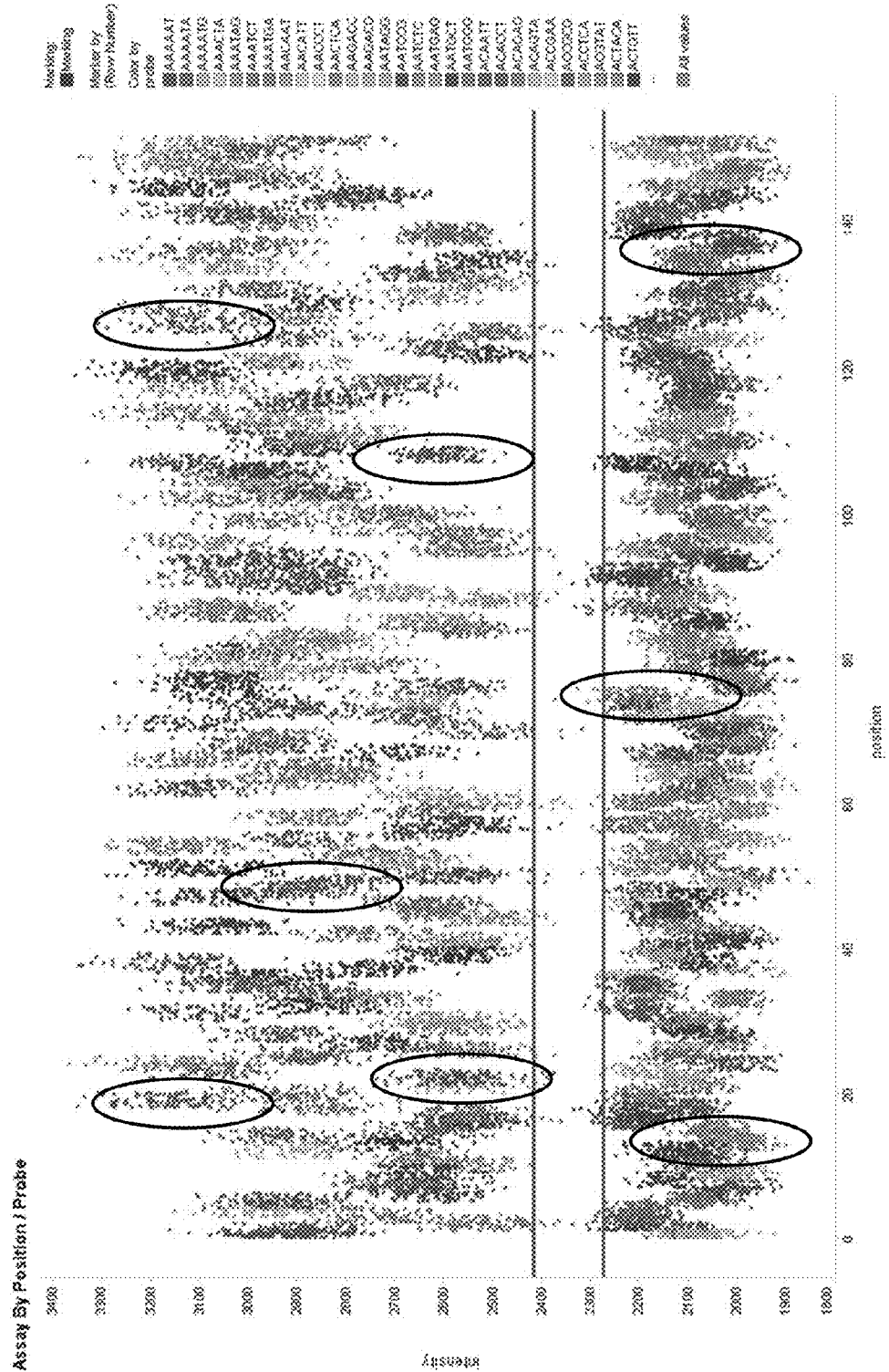
Figure 4B: Assay Intensities of Primers Containing 3 Degenerate Bases

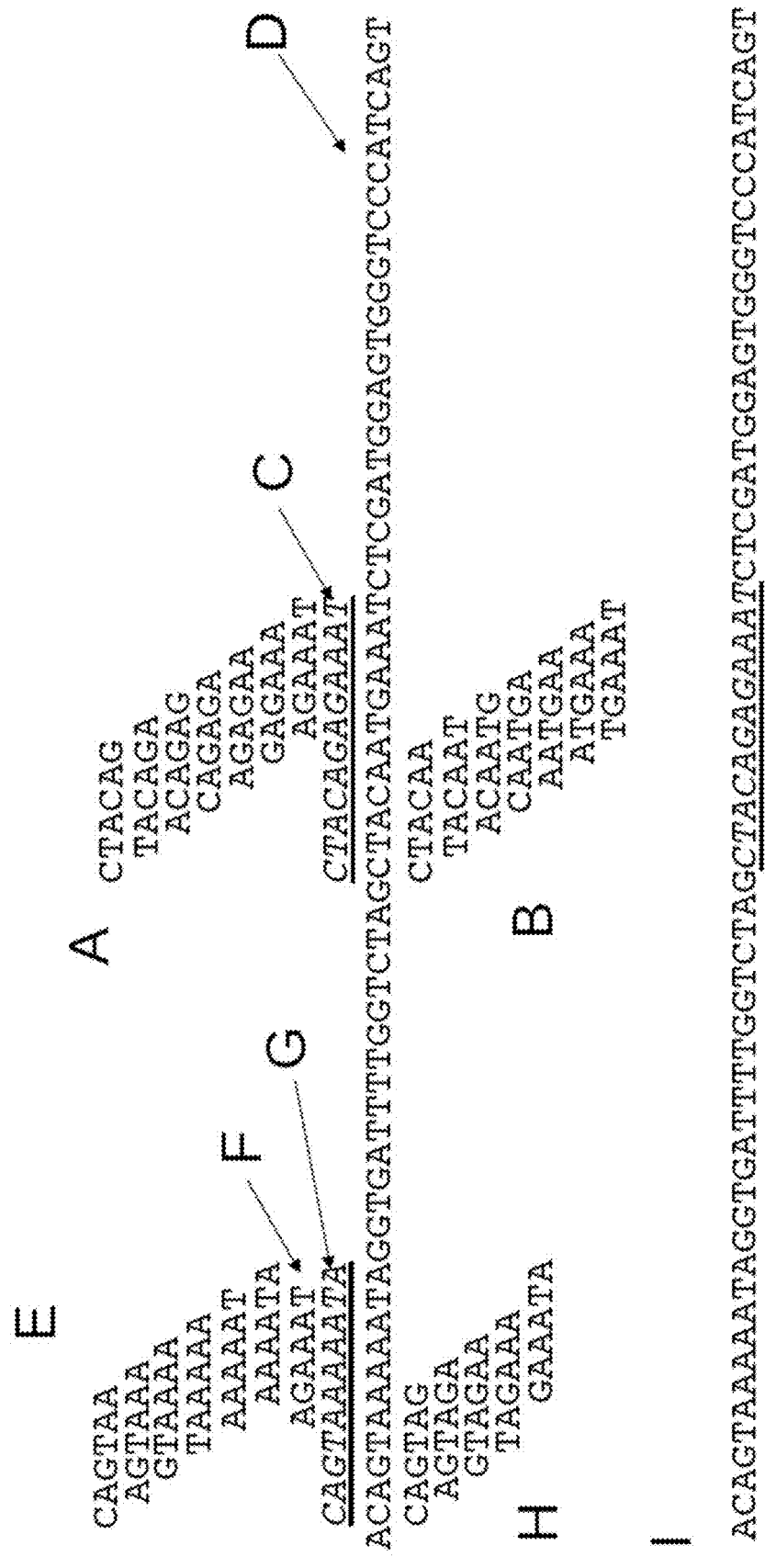

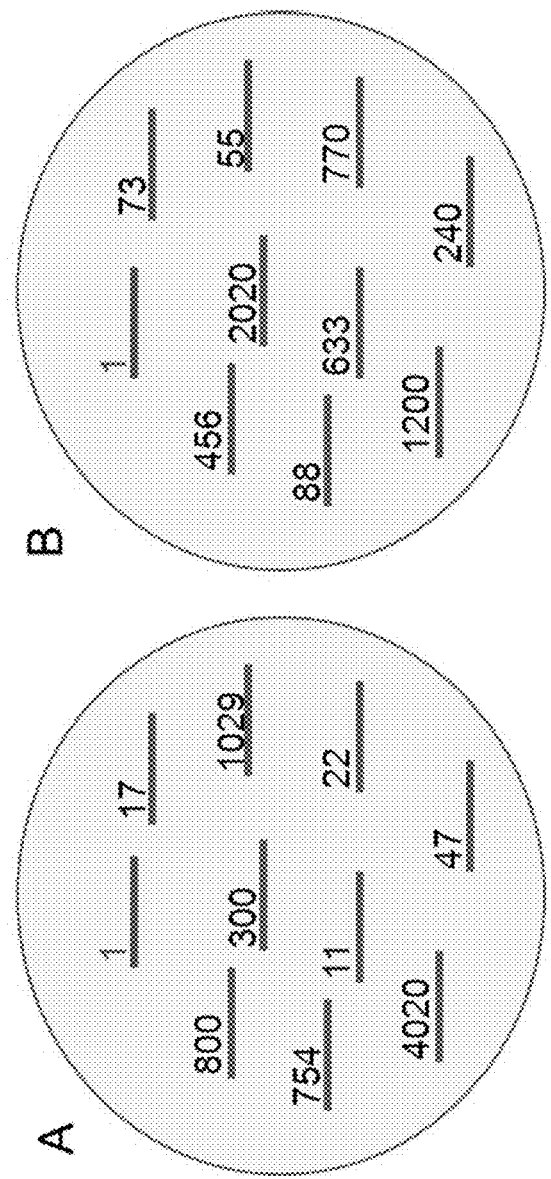
Figure 6A: Example of Multiplexed Primer Partitioning

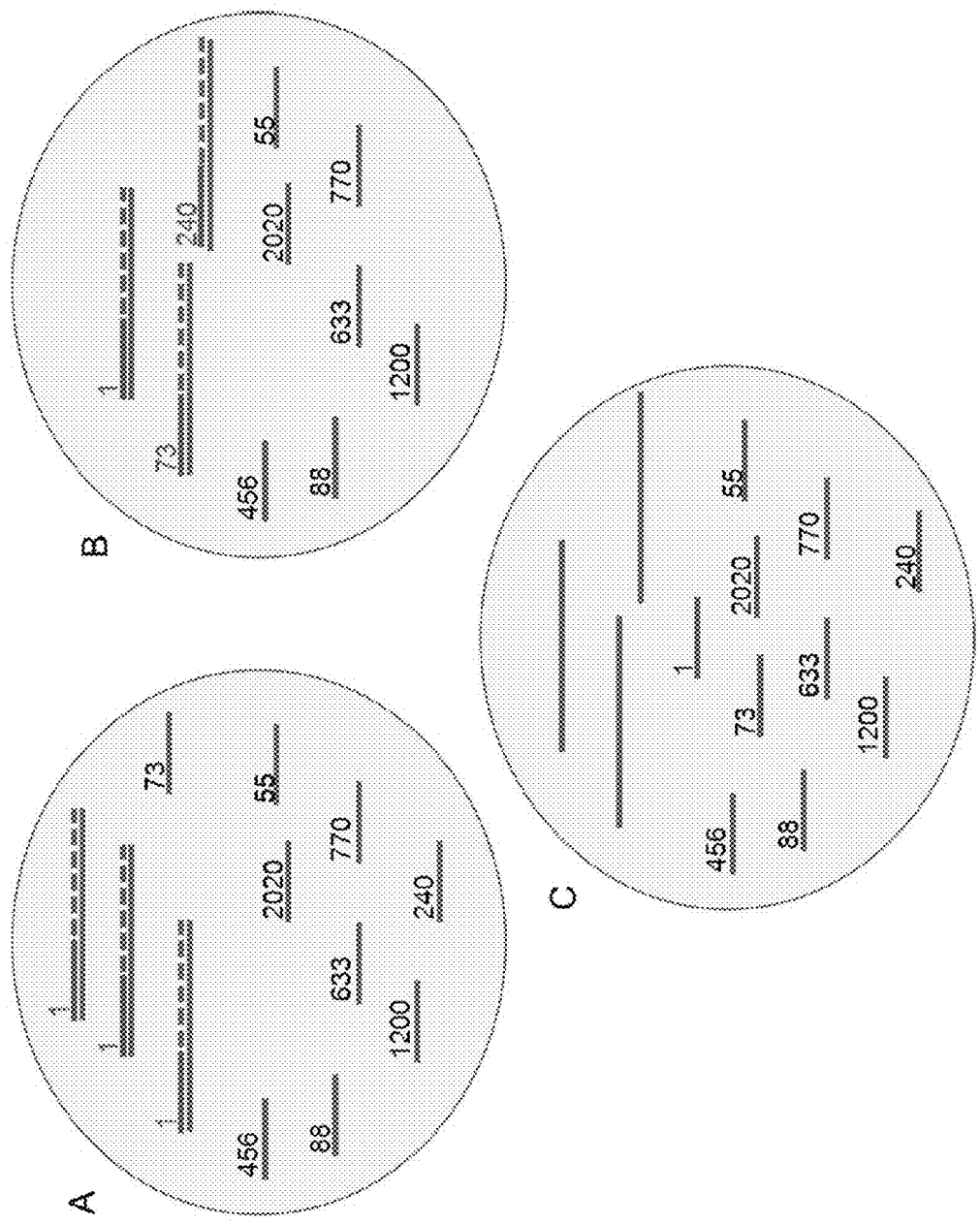
Figure 6B: Positive and Negative Outcomes for Multiplexed Partitions

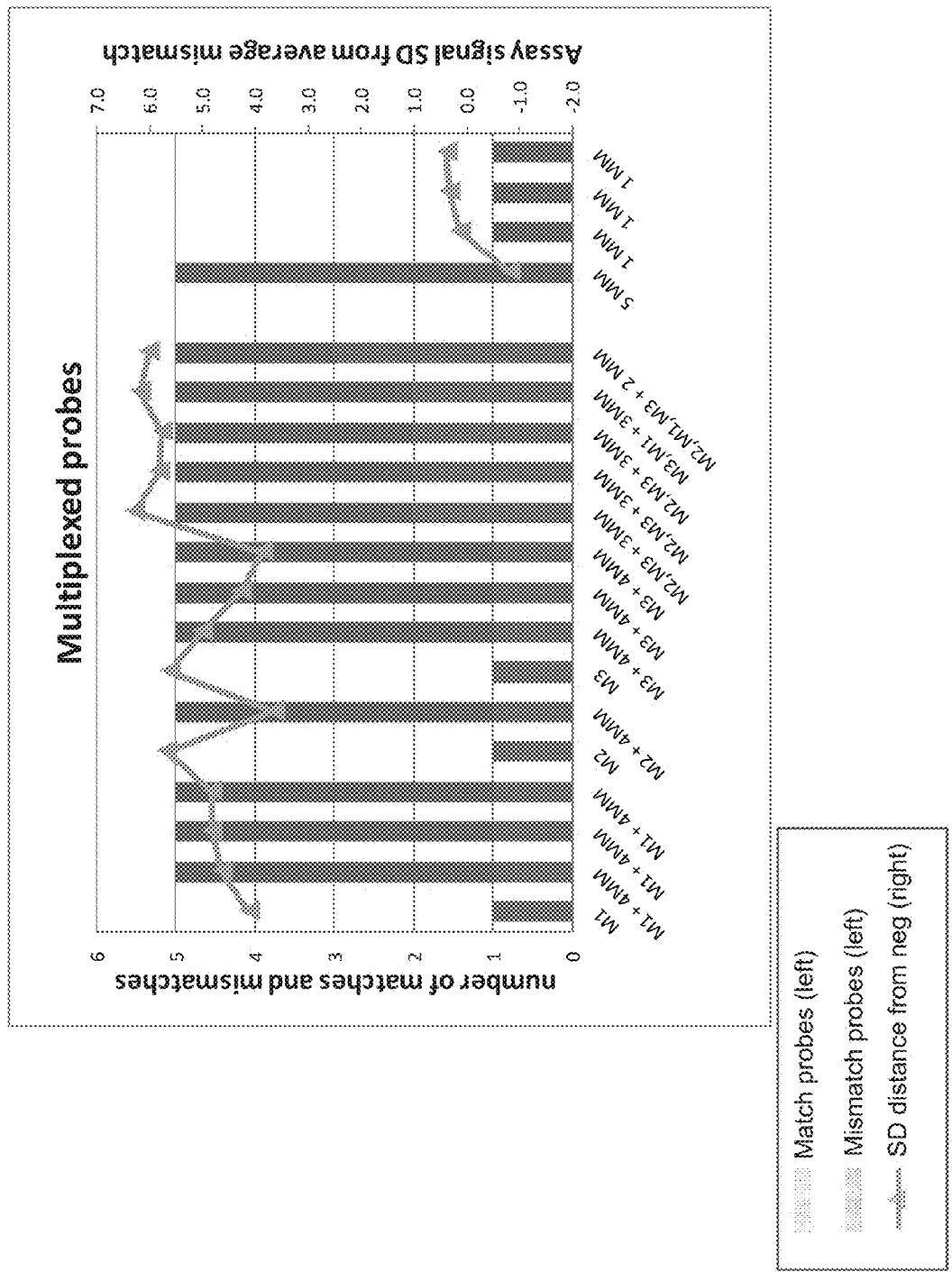
Figure 7A: Results of 5-plex Experiment

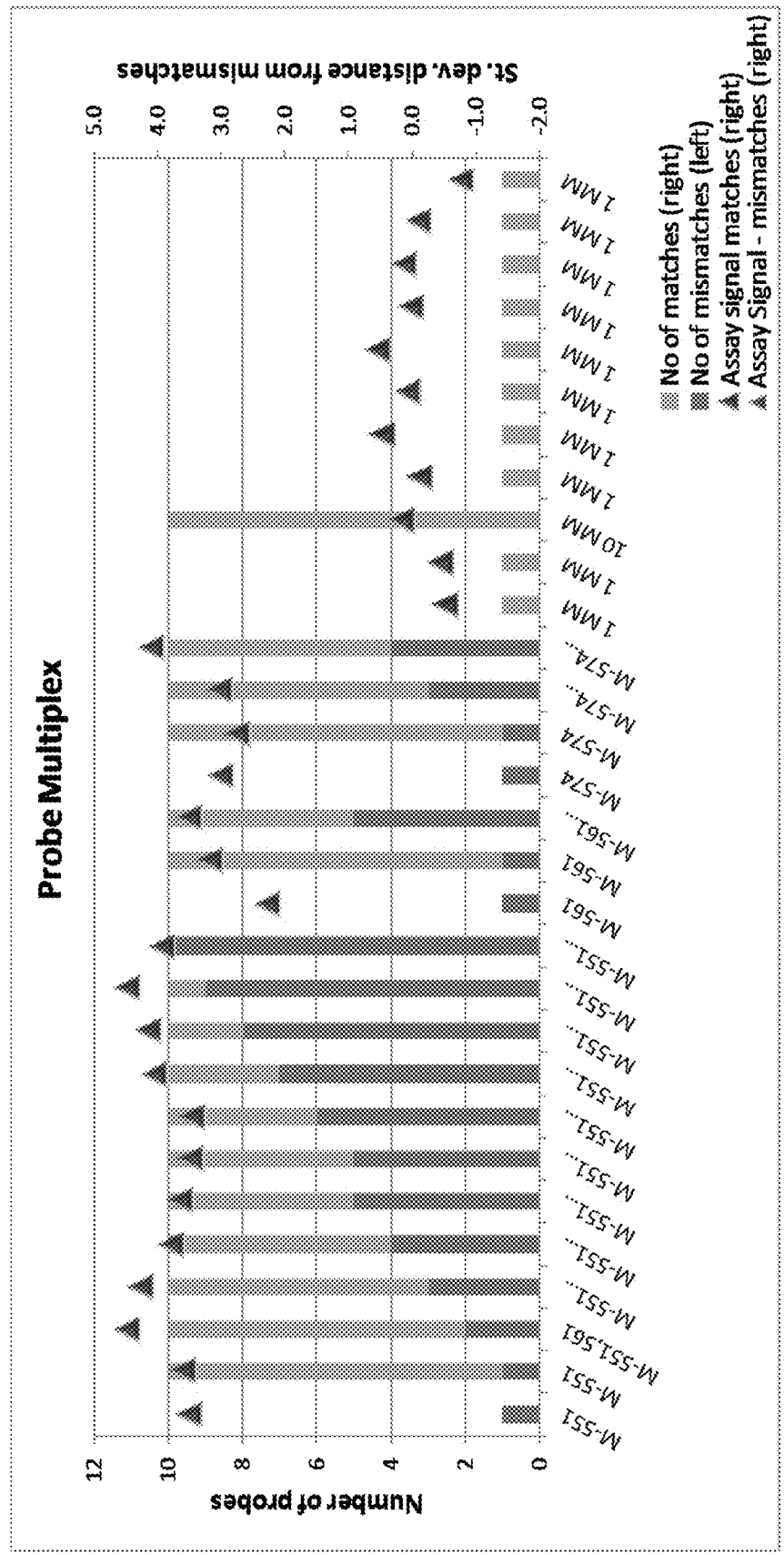
Figure 7B: Results of 10-plex Experiment

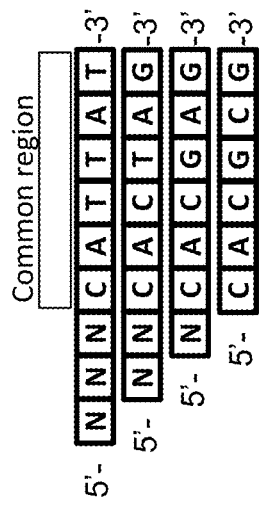
Figure 8: Degenerate Bases in Primer Oligos

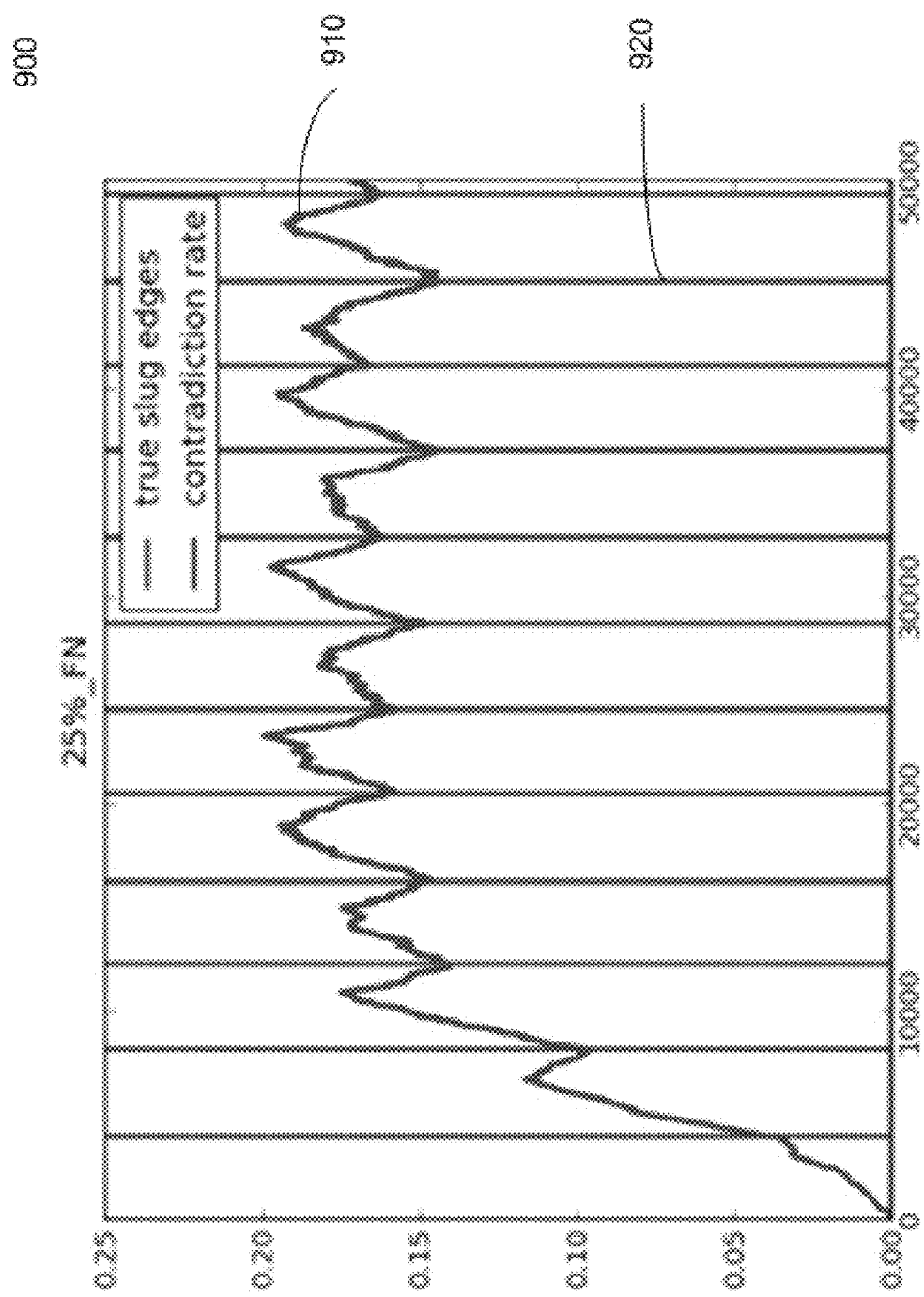
Figure 9: Temporal Segmentation Based on Contradiction Rate

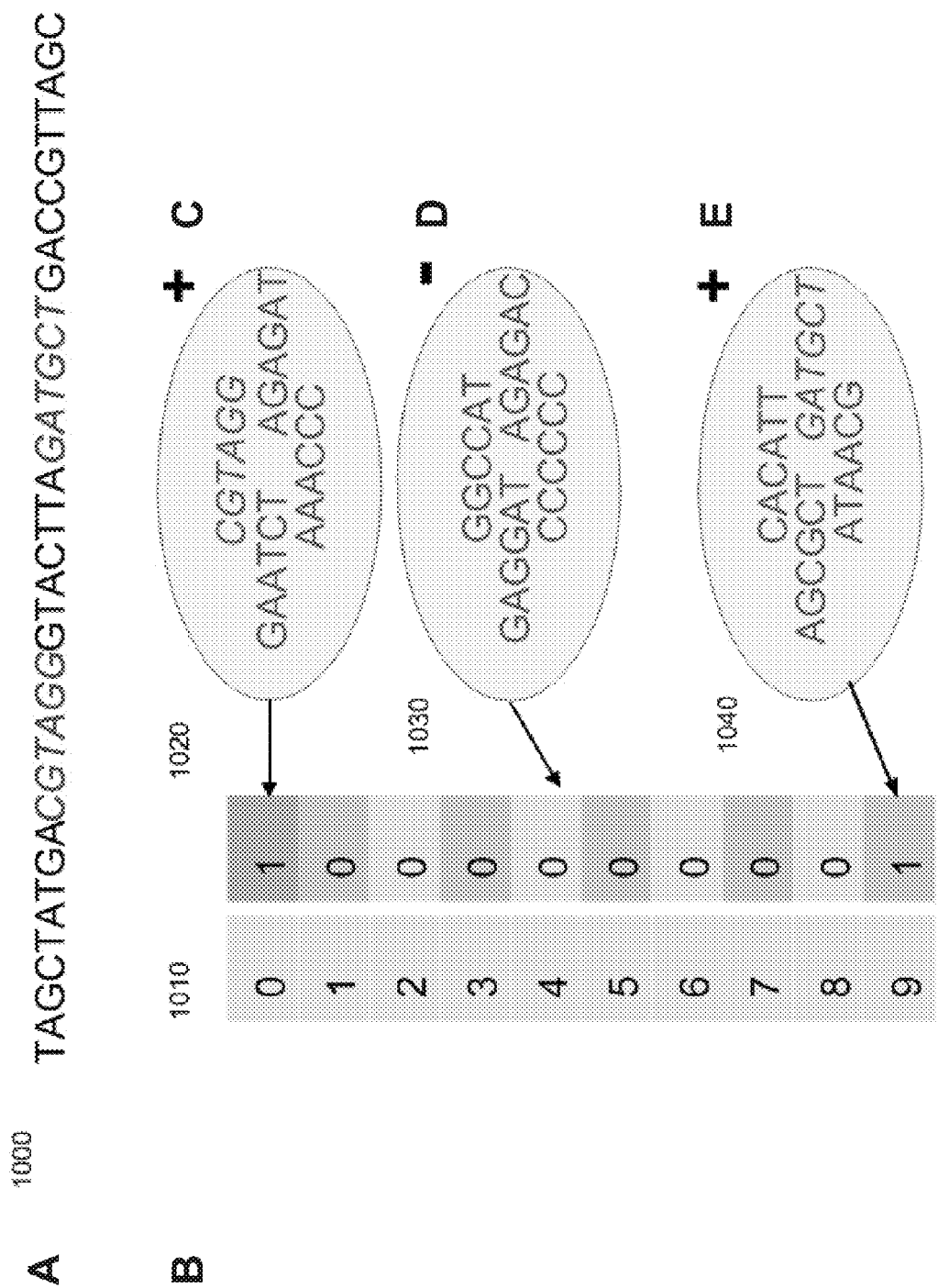
Figure 10: Partition Vector for a Reference Sequence

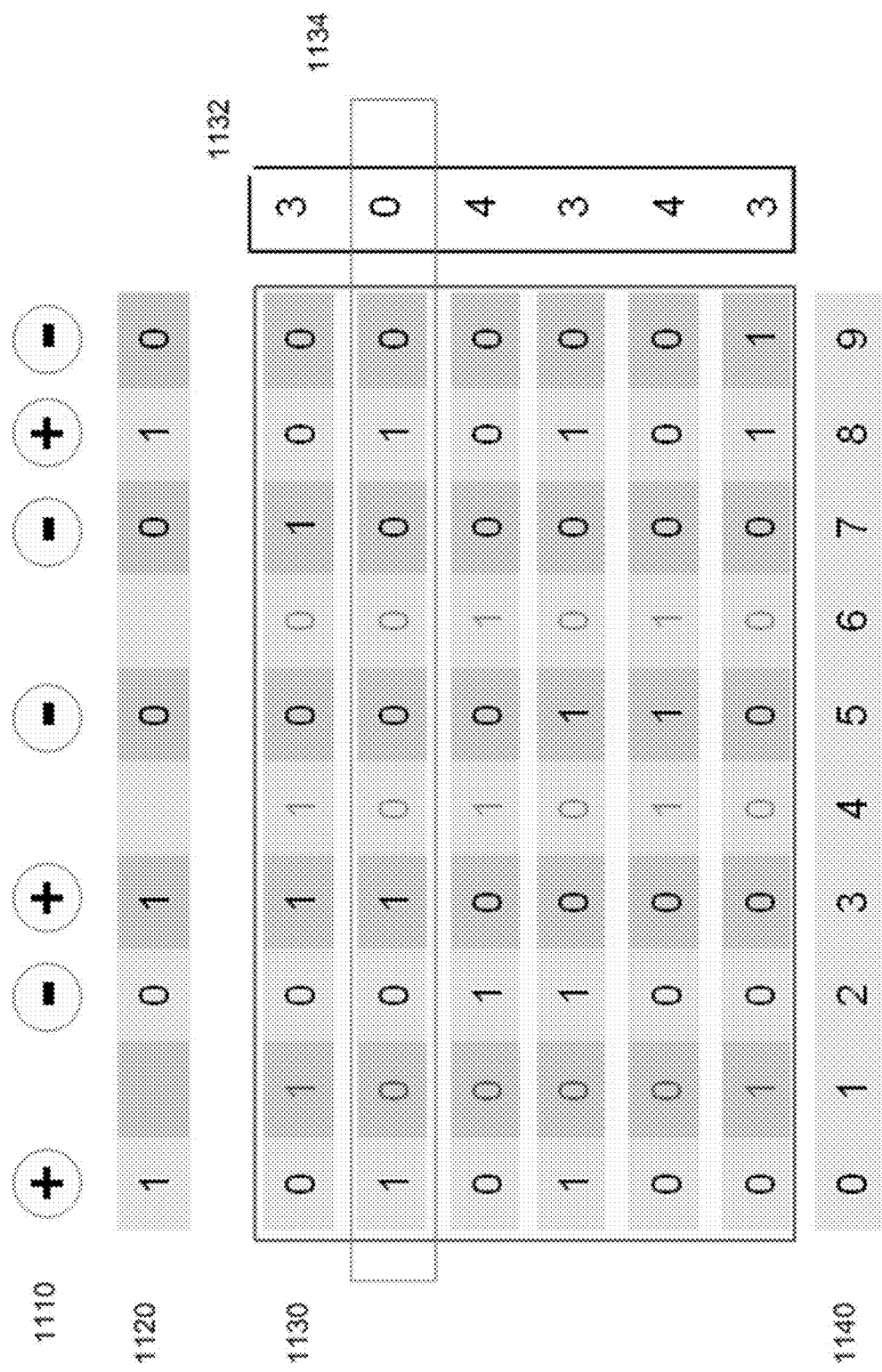
Figure 11: Process for Computing Mapping Scores

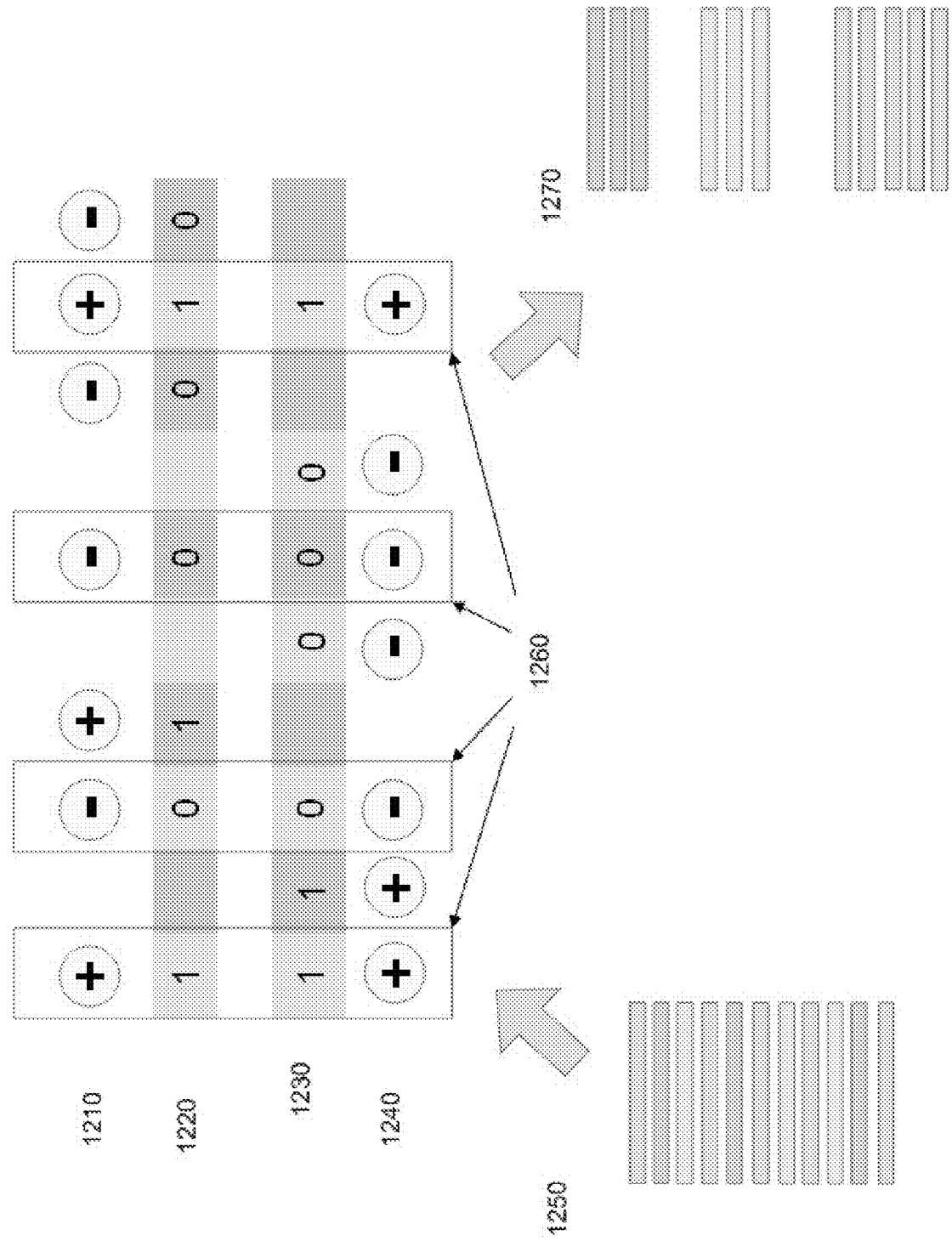

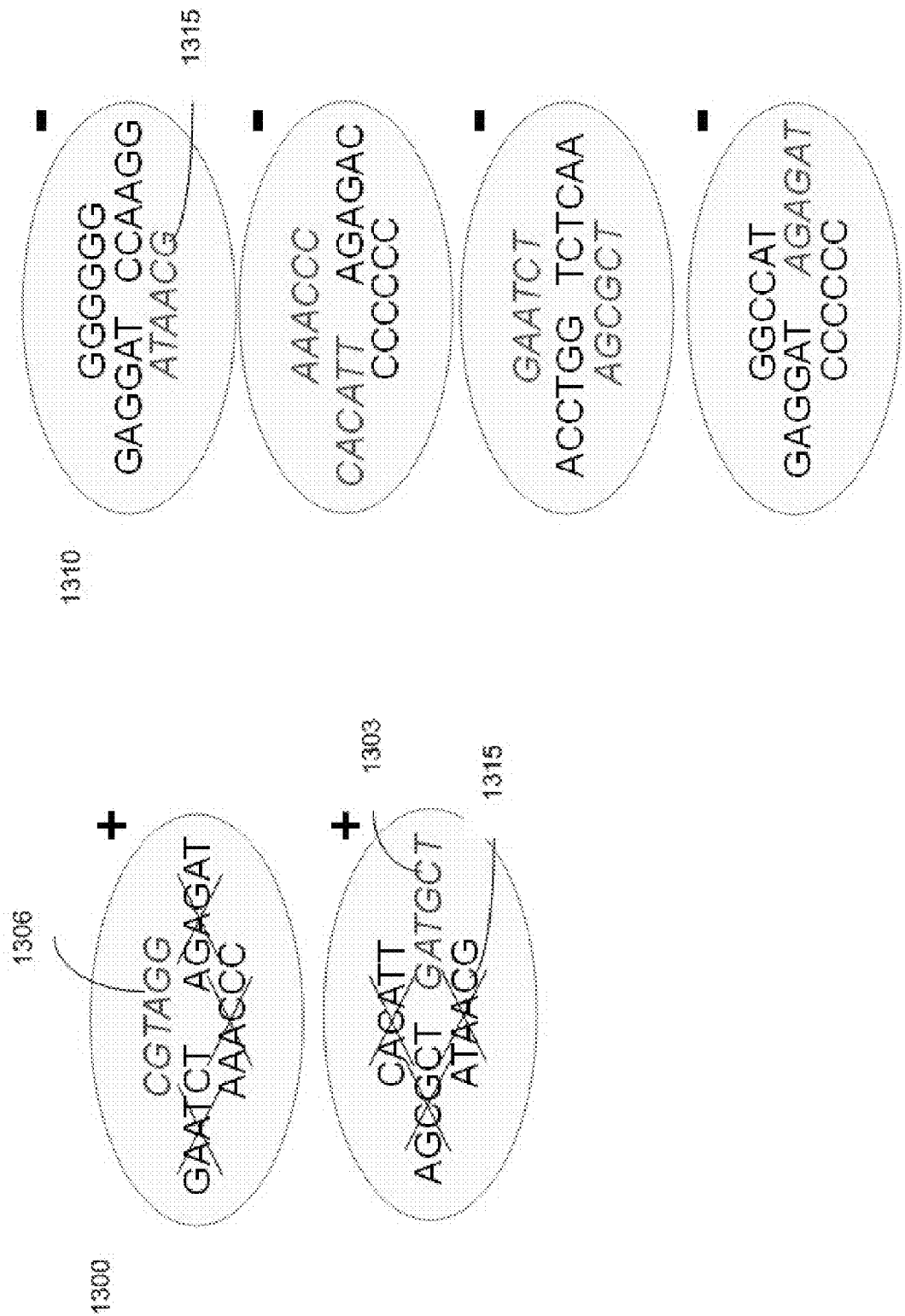
Figure 13: Negation Within a Cohort

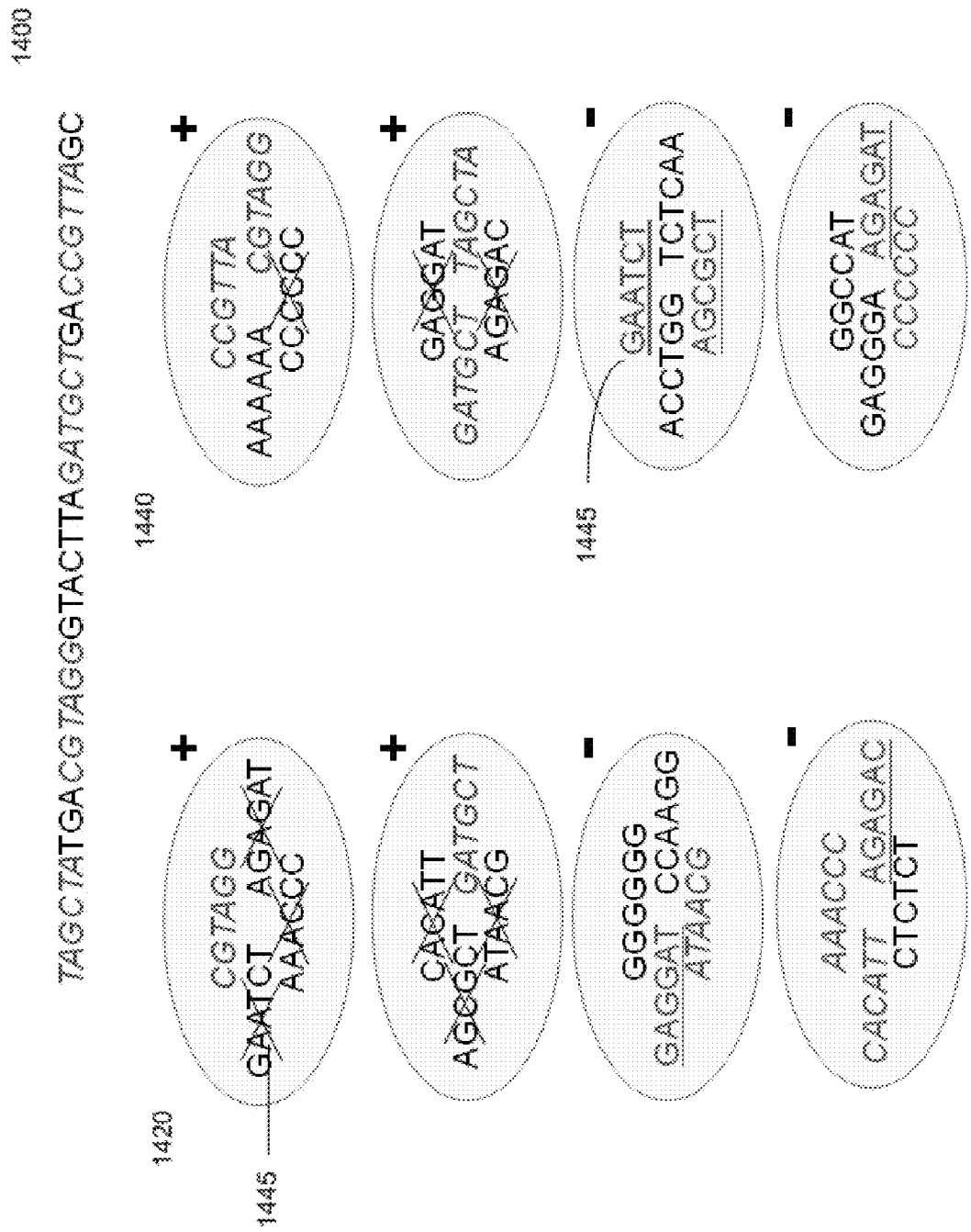
Figure 14: Negation Between Cohorts

Figure 15: Illustration of Gapped Primers

A

| Three classes of probes | | |
|---|---|---|
| GGACTT | == GGACTT | (4096 possible probes) |
| GNGNANCTT | == G-G-A-CTT | (4096 possible probes) |
| GGANCNTNT | == GGA-C-T-T | (4096 possible probes) |

B

Two different classes of gapped probes:
```
GGG-G-G-A      GAG-G-G-T
A-G-G-GCT      G-G-G-GAT
T-G-G-GGG      T-A-A-AGA
```

| Target Molecule | AATGGGTAGGGGGGTATAATTGAGAGATGAGGTGT | |
|---|---|---|
| Non-gapped hexamer probes | GGGGGG | GAGAGA |

Figure 16: Illustration of Assembly Process

| Stage | Description | Content |
|---|---|---|
| Stage 1 | Find an unambiguous path in overlap graph | A-T-CCT-G  GGG-A-A-T  G-G-G-GAT<br>T-CCT-C-G  GG-A-A-TT  G-G-GAT-A<br>CCT-G-G  G-A-A-TTG  G-GAT-A-G<br>GCT-G-G-G  A-A-TTG-G  GAT-A-G-G<br>GT-G-G-GG  A-A-TTG-G  GAT-A-G-G<br>T-G-G-GGG  A-TTG-G-G  AT-A-G-GT<br>G-G-GGG-A  TTG-G-G-G<br>G-GGG-A-A  TG-G-G-GA |
| Stage 2 | Initial scaffold | A-T-GGT-G-G-GGG-A-A-TTG-G-GAT-A-G-GT |
| Stage 3 | Leverage negatives to eliminate incorrect fill-in | Incorrect fill-in → T-A-A-AGA<br>Countering negative → GATAAA |
| Stage 4 | Fill in gaps with unambiguous positives | ATG-G-A-G    TATAAT    AGGTGT |
| Stage 5 | Fill in remaining gaps with positives that are unambiguous relative to scaffold + stages 3&4 | GGG-T-T-A    ATG-G-T-T<br>T-A-A-AGA |
| Stage 6 | Final assembly | AATGGGTAGGGGGTATAATTGAGAGATGAGGTGT |
| Stage 7 | Reference sequence (optional)<br>Leverage negatives to add confidence to variant calls | AATGGGTAGGGGTGGTATAATT-AGAGAGATGAGGTGT<br>AGGTG    AATT-AG<br>GGGTGG    ATT-AGA |

SYSTEMS AND METHODS FOR SEQUENCING IN EMULSION BASED MICROFLUIDICS

CROSS-REFERENCES TO RELATED APPLICATIONS

The present application is a continuation of U.S. patent application Ser. No. 14/290,867, filed on May 29, 2014, which claims benefit of priority to U.S. Provisional Patent Application No. 61/828,582, filed on May 29, 2013, each of which is incorporated herein by reference in its entirety.

REFERENCE TO SUBMISSION OF A SEQUENCE LISTING AS A TEXT FILE

The instant application contains a Sequence Listing which has been submitted electronically in ASCII format and is hereby incorporated by reference in its entirety. Said ASCII copy, created on Feb. 5, 2021, is named 097505-1061115-103320US_SL.txt and is 5,284 bytes in size.

BACKGROUND OF THE INVENTION

DNA sequencing is the process of determining the precise order of nucleotides within a DNA molecule, e.g., the order of the four bases—adenine, guanine, cytosine, and thymine—in a strand of DNA. The advent of rapid DNA sequencing methods has greatly accelerated biological and medical research and discovery.

Knowledge of DNA sequences has become useful for basic biological research, and in numerous applied fields such as diagnostic, biotechnology, forensic biology, and biological systematics. The rapid speed of sequencing attained with modern DNA sequencing technology has been instrumental in the sequencing of complete DNA sequences, or genomes of numerous types and species of life, including the human genome and other complete DNA sequences of many animal, plant, and microbial species.

BRIEF SUMMARY OF THE INVENTION

The patent or application file contains at least one drawing executed in color. Copies of this patent or patent application publication with color drawings will be provided by the Office upon request and payment of the necessary fee.

Provided herein are methods for determining a nucleotide sequence in a target nucleic acid. In some embodiments, the method comprises, partitioning a mixture comprising a plurality of copies of a target nucleic acid, thereby generating a plurality of target partitions; providing a series of primers in a plurality of primer partitions, wherein at least a majority of the primer partitions comprise two or more different primers having at least 4 designated nucleotides, with other nucleotide positions of the primers, if any, being degenerate positions or universal nucleotides; combining (i) at least a portion of the target partitions and (ii) primer partitions on a one-for-one basis to form a plurality of reaction partitions; hybridizing the target nucleic acid to the primers in the reaction partitions under conditions in which fully complementary primers hybridize to the target sequence and primers that are not fully complementary do not hybridize to the target nucleic acid; determining which primers in the series bind to the target nucleic acid; and determining the nucleotide sequence in a target nucleic acid based on which primers bind to the target nucleic acid.

In some embodiments, the series of primers comprises primers of at least 2, 3, or 4 different number of designated nucleotides over 4, 5, 6, 7, 8, 9, or 10 nucleotides, e.g., some primers have one number (e.g., X>4) of designated nucleotides and other primers in the series have a different number (e.g., Y>4).

In some embodiments, at least 100, 500, 1000, or 10000 portions of the target partition are generated; and the combining comprises combining each of the 100, 500, 1000, or 10000 portions with a different primer partition.

In some embodiments, the target nucleic acid is an amplicon.

In some embodiments, the target nucleic acid comprises a fluorescent moiety and is annealed to a quenching oligonucleotide that comprises a quencher, wherein annealing of the quencher to the target nucleic acid quenches fluorescence of the fluorescence moiety. In some embodiments, the determining comprises contacting the target nucleic acid annealed to the quencher oligonucleotide with a primer-dependent polymerase, wherein extension of the primers, if hybridized, results in displacement of the quencher oligonucleotide, thereby generating a fluorescent signal. In some embodiments, the primer portions comprise multiple primers having different sequences, and wherein the determining comprises: detecting the presence or absence of the fluorescent signal, wherein presence of the fluorescent signal indicates that one of the multiple primers hybridized to the target nucleic acid and lack of the fluorescent signal indicates none of the multiple primers hybridized to the target nucleic acid; and the method further comprises deconvoluting the nucleotide sequence of the target nucleic acid based on the presence or absence of the fluorescent signal and the sequences of the primers.

In some embodiments, the primer partitions contain one or more spectroscopic substances that coincide with particular primers in the partition such that the sequences of the primers in the partition is determinable by detection of a spectroscopic characteristic of the partition and wherein the determining further comprises detecting the spectroscopic characteristic and correlating the spectroscopic characteristic to the sequences of the primers.

In some embodiments, the series of primers comprise n number of sets of primers, with different partitions containing different sets of primers, wherein different sets of primers have 2-20 different unique primers and different primer partitions have no more than one primer in common, wherein n is between 1000-300,000. In some embodiments, partitions for each of the n sets contain one or more spectroscopic substances such that each of the n sets can be distinguished by a spectroscopic characteristic. In some embodiments, at least a majority of the primers in the set occur in two different sets of primers.

In some embodiments, no two primers in a primer partition has a sequence overlap of greater than two nucleotides.

In some embodiments, some of the primers in the series have 6-18 (e.g., 6, 7, 8, 9, 10, 11, 12, 13, 14, 15, 16, 17, or 18) designated nucleotides.

In some embodiments, the designated nucleotides are contiguous. In some embodiments, at least some of the designated nucleotides are non-contiguous such that at least two of the designated nucleotides are separated by at least one degenerate nucleotide position or universal nucleotide.

In some embodiments, the series has between 400-16000 primers of different sequence.

In some embodiments, the target nucleic acid is between 50-1000 nucleotides long.

In some embodiments, the target nucleic acid comprises a 3' stem loop.

In some embodiments, the partitions are drops. In some embodiments, the drops are contained in an emulsion.

Also provided is a a library of at least n different primer partitions, wherein the primer partitions comprise n number of sets of primers, with different partitions containing different sets of primers, wherein each set of primers have 2-20 different unique primers and different primer partitions have no more than one primer in common. In some embodiments, n is between 1000-300000. In some embodiments, the different primers have at least 4 designated nucleotides, with other nucleotide positions of the primers, if any, being degenerate positions or universal nucleotides. In some embodiments, the primer partitions comprise n number of sets of primers, with different partitions containing different sets of primers, wherein each set of primers have 8-12 different unique primers and different primer partitions have no more than one primer in common. In some embodiments, partitions for each of the n sets contain one or more spectroscopic substances such that each of the n sets can be distinguished by a spectroscopic characteristic.

In some embodiments, at least a majority of primers in the set occur in two different sets of primers.

In some embodiments, no two primers in a primer partition has a sequence overlap of greater than one, two, or three nucleotides.

In some embodiments, some of (or a majority of) the primers have 6-18 designated nucleotides.

In some embodiments, some of, a majority of, or all of the designated nucleotides are contiguous.

In some embodiments, at least some of the designated nucleotides are non-contiguous such that at least two of the designated nucleotides are separated by at least one degenerate nucleotide position or universal nucleotide.

In some embodiments, the library comprises 400-16000 primers of different sequence.

In some embodiments, the partitions are drops. In some embodiments, the drops are contained in an emulsion.

Also provided is a vessel comprising the library as described above or elsewhere herein. In some embodiments, the vessel comprises one or more microfluidic channel in fluid communication with the library.

Also provided is a system for generating a nucleotide sequence of a target nucleic acid. In some embodiments, the system comprises a first vessel comprising a series of primers in a plurality of primer drops, wherein at least a majority of the primer drops comprise two or more different primers having at least 4 designated nucleotides, with other nucleotide positions of the primers, if any, being degenerate positions or universal nucleotides; a first microfluidic channel providing fluid communication between the first vessel and a detector; and the detector.

In some embodiments, the system further comprises a second vessel comprising primer pairs for amplifying the target nucleic acid; a second microfluidic channel providing fluid communication between the second vessel and the first microfluidic channel; and a sample nucleic acid vessel in fluid communication with the second microfluidic channel.

In some embodiments, the system further comprises a first droplet injector configured to inject nucleic acids from the sample nucleic acid vessel into drops comprising primer pairs from the second vessel and located in the second microfluidic channel to form mixture drops; and a second droplet injector configured to inject portions of the mixture drops into primer drops that travel down the first microfluidic channel.

In some embodiments, the drops are contained in an emulsion.

In some embodiments, a portion of the second microfluidic channel is serpentine.

In some embodiments, the first vessel comprises at least 100, 500, 1000, or 10000 of said primer drops.

In some embodiments, the system further comprises one or more pump for pushing drops through one or more of the microfluidic channels.

In some embodiments, at least a majority of primers in the set occur in two different sets of primers. In some embodiments, no two primers in a primer partition has a sequence overlap of greater than one, two, or three nucleotides.

In some embodiments, some of, a majority of, or all of the primers in the series have 6-18 designated nucleotides.

In some embodiments, the designated nucleotides are contiguous.

In some embodiments, at least some of the designated nucleotides are non-contiguous such that at least two of the designated nucleotides are separated by at least one degenerate nucleotide position or universal nucleotide.

In some embodiments, the series has between 400-16000 primers of different sequence.

Also provided are methods of determining the nucleotide sequence of a target nucleic acid based on hybridization of primers. In some embodiments, the method comprises: receiving a data from an experiment involving hybridization of a plurality of primers to a target nucleic acid, the data comprising positive hybridization and negative primer hybridization results; assembling a scaffold nucleotide sequence based on positively hybridizing primers, wherein the scaffold comprises unambiguous nucleotides based on the positively hybridizing primers; performing one or both of: (a) correcting the scaffold sequence by removing or changing one or more nucleotide in the scaffold sequence that is inconsistent with the negative primer hybridization results; (b) determining ambiguous options for scaffold portions that are ambiguous based on positively hybridizing primers; and resolving at least one of said ambiguous options based on negatively hybridizing primers, thereby determining the nucleotide sequence of a target nucleic acid based on hybridization of primers.

Also provided are methods of subdividing a constant stream of data signals representing hybridization in a plurality of reaction partitions generated from merging of portions of a target nucleic acid partition into a primer partition. In some embodiments, the method comprises obtaining the constant data stream; determining a rate of self-contradiction among reaction partitions as a function of time across a sliding window of fixed length; detecting minima in the rate; and subdividing the data using the minima as borders, wherein borders delineate the ends of signal from target nucleic acid partitions.

Also provided are methods of determining a nucleotide sequence of a target nucleic acid based on hybridization of primers. In some embodiments, the method comprises receiving, by a computer system, data from an experiment involving hybridization of a plurality of primers to a target nucleic acid, the data comprising positive hybridization and negative primer hybridization results; analyzing, by the computer system, the data to identify a first cohort of primers as positively hybridizing to the target nucleic acid and a second cohort of primers as not hybridizing to the target nucleic acid; assembling, by the computer system, a scaffold nucleotide sequence based on the first cohort of primers, wherein the scaffold nucleotide sequence comprises unambiguous positions where a particular nucleotide is specified and ambiguous positions where a particular nucleotide is not specified; resolving, by the computer system, at least one of said ambiguous positions based on the second cohort of primers.

In some embodiments, resolving a first ambiguous position includes: determining that a first primer of the first cohort does not align to a first ambiguous position when such an alignment is consistent with a second primer of the second cohort also aligning to the first ambiguous position.

In some embodiments, resolving a first ambiguous position includes: identifying one or more unambiguous primers of the first cohort by excluding alignment positions for the unambiguous primers based on the second cohort of primers; using the one or more unambiguous primers of the first cohort to determine one or more nucleotides at one or more ambiguous positions, thereby obtaining an updated scaffold nucleotide sequence.

In some embodiments, the method further comprises: identifying a first subset of ambiguous primers, the first subset being a subset of the first cohort of primers, wherein an ambiguous primer aligns to multiple positions in the updated scaffold nucleotide sequence; excluding alignment positions of a first ambiguous primer of the first subset based on the second cohort of primers, thereby making the first ambiguous primer into a first unambiguous primer; and using the first unambiguous primer to resolve a second ambiguous position in the updated scaffold nucleotide sequence.

In some embodiments, assembling the scaffold nucleotide sequence is further based on the second cohort of primers. In some embodiments, assembling the scaffold nucleotide sequence includes: determining that a first primer of the first cohort does not align to a first position of the scaffold nucleotide sequence when such an alignment is consistent with a second primer of the second cohort also aligning to the first position. In some embodiments, the method further comprises: identifying the first position as an ambiguous position based on determining that the first primer of the first cohort does not align to the first position of the scaffold nucleotide sequence. In some embodiments, the first cohort of primers includes primers having a gap between nucleotides.

In some embodiments, the method further comprises resolving ambiguous options in the scaffold by comparing the scaffold to a reference sequence.

In some embodiments, the data from an experiment involving hybridization of a plurality of primers to a target nucleic acid represents hybridization of different primers have at least 4 designated nucleotides, with other nucleotide positions of the primers, if any, being degenerate positions or universal nucleotides.

In some embodiments, the data from an experiment involving hybridization of a plurality of primers to a target nucleic acid represents hybridization of primers within primer partitions, the primer partitions comprising n number of sets of primers, with different partitions containing different sets of primers, wherein each cohort of primers have 8-12 different unique primers and different primer partitions have no more than one primer in common.

In some embodiments, said data further comprises data from partitions for each of the n sets contain one or more spectroscopic substances such that each of the n sets can be distinguished by a spectroscopic characteristic.

In some embodiments, at least a majority of primers in the cohort occur in two different sets of primers. In some embodiments, no two primers in a primer partition has a sequence overlap of greater than two nucleotides. In some embodiments, some of (or a majority of) the primers have 6-18 designated nucleotides. In some embodiments, the designated nucleotides are contiguous.

In some embodiments, at least some of (or a majority of) the designated nucleotides are non-contiguous such that at least two of the designated nucleotides are separated by at least one degenerate nucleotide position or universal nucleotide.

In some embodiments, the plurality has between 400-16000 primers of different sequence.

Also provided is a method of identifying primer/target nucleic acid partitions as being generated from a same target nucleic acid partition mixture drop. In some embodiments, the method comprises: receiving a data signal obtained by a detector over a time period, the data signal including signals from a plurality of reaction partitions generated from a plurality of mixture drops, each mixture drop corresponding to a cohort of partitions and including copies of at least one target nucleic acid, each partition including one or more primers, wherein the data signal includes data about whether at least one primer in a partition hybridizes to a target nucleic acid; identifying a hybridization status of each partition based on the respective signal of the respective partition, the hybridization status of a partition indicating whether a primer in the partition hybridized to a target nucleic acid, wherein a signal of a particular partition corresponds to a particular time; for each of a plurality of particular times in the time period: for a time window around the particular time: calculating an amount of partitions that have contradictory hybridization statuses and include a same primer, thereby obtaining a temporal function; identifying extrema in the temporal function; and determining a cohort of successive partitions occurring between corresponding extrema in the temporal function as corresponding to a same mixture drop.

In some embodiments, the extrema are minima between peaks. In some embodiments, the amount of partitions that have contradictory hybridization statuses corresponds to an amount of primers that are in partitions with contradictory hybridization statuses.

In some embodiments, the amount of partitions is normalized by a number of distinct partitions in the time window, wherein two partitions are distinct when the two partitions include at least one different primer.

In some embodiments, the time window is specified as a number of partitions, and wherein the time window is centered around a partition at the particular time. In some embodiments, the number of partitions in the time window is selected based on the number of partitions created from a mixture drop.

In some embodiments, the method further comprises: identifying that a first cohort of successive partitions correspond to a first mixture drop that includes a first target nucleic acid; determining whether each primer in the first cohort hybridizes to the first target nucleic acid based on the signals for the first cohort; using the primers in the first cohort and a hybridization state of the primers in the first cohort to determine a nucleotide sequence of the first target nucleic acid.

Also provided is a method of identifying a mixture drop as including a target nucleic. In some embodiments, the method comprises: receiving a hybridization status of each of a plurality of partitions, each partition including one or more primers, wherein each of a plurality of mixture drops is partitioned and each includes copies of one or more target nucleic acids, the hybridization status of a partition indicating whether at least one primer in the partition hybridized to a target nucleic acid; identifying a first cohort of partitions as corresponding to a first mixture drop; creating a first bit vector for the first cohort of partitions, wherein each value in the bit vector corresponds to a hybridization status of a respective partition of the first cohort cohort; comparing the first bit vector to a plurality of reference bit vectors to obtain a difference value relative to each of the plurality of reference bit vectors, each reference bit vector corresponding to a different reference nucleic acid and including values of hybridization status of each partition in the first cohort relative to the reference nucleic acid; and identifying a first target nucleic acid in the first mixture drop based on the difference values.

In some embodiments, comparing the first bit vector to a first reference bit vector includes: incrementing a counter for each partition of the first cohort that has a different hybridization status from the first reference bit vector. In some embodiments, the reference nucleic acid with a lowest counter is selected as the first target nucleic acid. In some embodiments, the reference nucleic acid with a lowest counter is selected as the first target nucleic acid when the lowest counter is at least a predetermine amount less than a next highest counter.

In some embodiments, each of the reference nucleic acids has a known sequence. V the method further comprises: for each reference nucleic acid: creating a reference bit vector by determining an expected hybridization status for each partition in the first cohort, the expected hybridization status for a partition being determined based on the primers in the partition.

In some embodiments, the reference nucleic acids correspond to nucleic acids in other mixture drops. In some embodiments, the method further comprises: clustering bit vectors of a plurality of mixture drops; and identifying a first cluster of mixture drops that include the first target nucleic acid based on a similarity of the bit vectors of the first cluster.

In some embodiments, the method further comprises: using the primers in the first cohort of partitions to determine a nucleotide sequence of the first target nucleic acid.

In some embodiments, each partition includes a plurality of primers, the method further comprising: identifying primers in the first cohort of partitions that positively hybridize to the first target nucleic acid; assembling the identified primers to determine the nucleotide sequence of the first target nucleic acid.

Also provided is a method of determining a hybridization state of a primer for a mixture drop. In some embodiments, the method comprises: receiving a data signal obtained by a detector over a time period, the data signal including signals from a plurality of partitions of a plurality of mixture drops, each mixture drop corresponding to a cohort of partitions and including copies of at least one target nucleic acid, each partition including a plurality of primers; identifying a first cohort of partitions as corresponding to a first mixture drop; determining that the first cohort of partitions corresponds to a first target nucleic acid; determining a hybridization status of each partition of the first cohort based on the respective signal of the respective partition, the hybridization status of a partition indicating whether at least one primer in the partition hybridized to the first target nucleic acid; identifying the primers in each partition of the first cohort, wherein a plurality of the partitions of the first cohort include a first primer; determining whether the first primer is in any partitions of the first cohort having a negative hybridization status; and determining whether the first primer hybridized to the first target nucleic acid based on whether the first primer is in any partitions of the first cohort having a negative hybridization status.

In some embodiments, the first primer is determined not to have hybridized to the first target nucleic acid when the first primer is in one or more partitions having a negative hybridization status.

In some embodiments, the first primer is determined not to have hybridized to the first target nucleic acid when the first primer is in at least a specified proportion of partitions having a negative hybridization status relative to partitions having a positive hybridization status.

In some embodiments, the method further comprises: determining a plurality of other sets of partitions as corresponding to the first target nucleic acid; identifying the primers in each of the other sets of partitions; determining whether the first primer is in any partitions of the other sets having a negative hybridization status; and determining whether the first primer hybridized to the first target nucleic acid based on whether the first primer is in any partitions of the other sets having a negative hybridization status.

In some embodiments, the method further comprises: determining a group of primers that hybridize to the first target nucleic acid; and using the sequences of the group of primers to assemble a nucleotide sequence of the first target nucleic acid.

In some embodiments, assembling the nucleotide sequence of the first target nucleic acid includes using a reference sequence for the first target nucleic acid.

Other aspects of the invention are described elsewhere herein.

Definitions

The term "nucleic acid amplification" or "amplification reaction" refers to any in vitro means for multiplying the copies of a target sequence of nucleic acid. Such methods include but are not limited to polymerase chain reaction (PCR), DNA ligase chain reaction (see U.S. Pat. Nos. 4,683,195 and 4,683,202; PCR Protocols: A Guide to Methods and Applications (Innis et al., eds, 1990)), (LCR), QBeta RNA replicase, and RNA transcription-based (such as TAS and 3 SR) amplification reactions as well as others known to those of skill in the art.

"Amplifying" refers to a step of submitting a solution to conditions sufficient to allow for amplification of a polynucleotide. Components of an amplification reaction include, e.g., primers, a polynucleotide template, polymerase, nucleotides, and the like. The term amplifying typically refers to an "exponential" increase in target nucleic acid. However, amplifying as used herein can also refer to linear increases in the numbers of a select target sequence of nucleic acid, such as is obtained with cycle sequencing.

"Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step. PCR can be performed as end-point PCR (i.e., only monitored at an end point) or as quantitative PCR (monitored in "real time").

A "primer" refers to a polynucleotide sequence that hybridizes to a sequence on a target nucleic acid and serves as a point of initiation of nucleic acid synthesis. Primers can be of a variety of lengths but are less than 50 nucleotides in length, for example 5-30 nucleotides, in length. The length and sequences of primers for use in PCR can be designed based on principles known to those of skill in the art, see, e.g., Innis et al., supra.

A "template" refers to a polynucleotide sequence that comprises the polynucleotide to be amplified, flanked by or a pair of primer hybridization sites. Thus, a "target template" comprises the target polynucleotide sequence flanked by hybridization sites for a "forward" primer and a "reverse" primer.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications including but not limited to capping with a fluorophore (e.g., quantum dot) or another moiety.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

A "polymerase" refers to an enzyme that performs template-directed synthesis of polynucleotides, e.g., DNA and/or RNA. The term encompasses both the full length polypeptide and a domain that has polymerase activity. DNA polymerases are well-known to those skilled in the art, including but not limited to DNA polymerases isolated or derived from *Pyrococcus furiosus, Thermococcus litoralis,* and *Thermotoga maritime,* or modified versions thereof. Additional examples of commercially available polymerase enzymes include, but are not limited to: Klenow fragment (New England Biolabs® Inc.), Taq DNA polymerase (QIAGEN), 9°N™ DNA polymerase (New England Biolabs® Inc.), Deep Vent™ DNA polymerase (New England Biolabs® Inc.), Manta DNA polymerase (Enzymatics®), Bst DNA polymerase (New England Biolabs® Inc.), and phi29 DNA polymerase (New England Biolabs® Inc.). Polymerases include both DNA-dependent polymerases and RNA-dependent polymerases such as reverse transcriptase. At least five families of DNA-dependent DNA polymerases are known, although most fall into families A, B and C. There is little or no sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli,* three types of DNA polymerases have been found, DNA polymerases I (family A), II (family B), and III (family C). In eukaryotic cells, three different family B polymerases, DNA polymerases $\alpha$, $\delta$, and $\epsilon$, are implicated in nuclear replication, and a family A polymerase, polymerase $\gamma$, is used for mitochondrial DNA replication. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

The terms "label," "detectable label, "detectable moiety," and like terms refer to a composition detectable by spectroscopic, photochemical, biochemical, immunochemical, chemical, or other physical means. For example, useful labels include fluorescent dyes (fluorophores), luminescent agents, electron-dense reagents, enzymes (e.g., as commonly used in an ELISA), biotin, digoxigenin, $^{32}$P and other isotopes, haptens, and proteins which can be made detectable, e.g., by incorporating a radiolabel into the peptide or used to detect antibodies specifically reactive with the peptide. The term includes combinations of single labeling agents, e.g., a combination of fluorophores that provides a unique detectable signature, e.g., at a particular wavelength or combination of wavelengths. Any method known in the art for conjugating label to a desired agent may be employed, e.g., using methods described in Hermanson, *Bioconjugate Techniques* 1996, Academic Press, Inc., San Diego.

A "stem loop," also known as a "hairpin" or "hairpin loop," refers to a secondary structure formed by a single-stranded oligonucleotide when complementary bases in a first part of the linear strand hybridize with bases in a second part of the same strand. The sequence in the second part of the sequences is the reverse complement of the first part sequence, thereby allowing for hybridization.

As used herein, the term "partitioning" or "partitioned" refers to separating a sample into a plurality of portions, or "partitions." Partitions can be solid or fluid. In some embodiments, a partition is a solid partition, e.g., a microchannel. In some embodiments, a partition is a fluid partition, e.g., a droplet. In some embodiments, a fluid partition (e.g., a droplet) is a mixture of immiscible fluids (e.g., water and oil). In some embodiments, a fluid partition (e.g., a droplet) is an aqueous droplet that is surrounded by an immiscible carrier fluid (e.g., oil).

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1: Microfluidic Workflow.

FIG. 1 is a high-level schematic of the microfluidic device used in sequencing. There are two reservoirs that are preloaded with emulsified reagents prior to running the sequencing experiment. Reservoir A contains emulsified reagents necessary for performing a PCR reaction, including at least one PCR primer pair. Reservoir B contains emulsified reagents necessary for the sequencing assay including at least one sequencing primer oligo. Injection point C is where a small portion of the genomic DNA sample gets injected into each of the PCR partitions. The serpentine channel in section D flows across at least two distinct thermal zones and acts as an online thermal cycler. Each of the PCR partitions ends up at the second injection point E where the amplified material contained therein is injected into a series of relatively smaller sequencing primer partitions. The sequencing primer partitions flow downstream of injection point E to the optical detector at point F. The optical detector at F reads the fluorescent signal from each primer partition.

FIG. 2: Software Architecture

FIG. 2 is laid out to show which software modules are executed at which stage of the process and acting at which temporal granularity and operating on which inputs. For example, the signal processing module is executed once for every primer partition measured by the optical detector. Figure discloses SEQ ID NO: 9.

FIG. 3A: Four Dimensional Dye Profile Clusters

Figure 17:
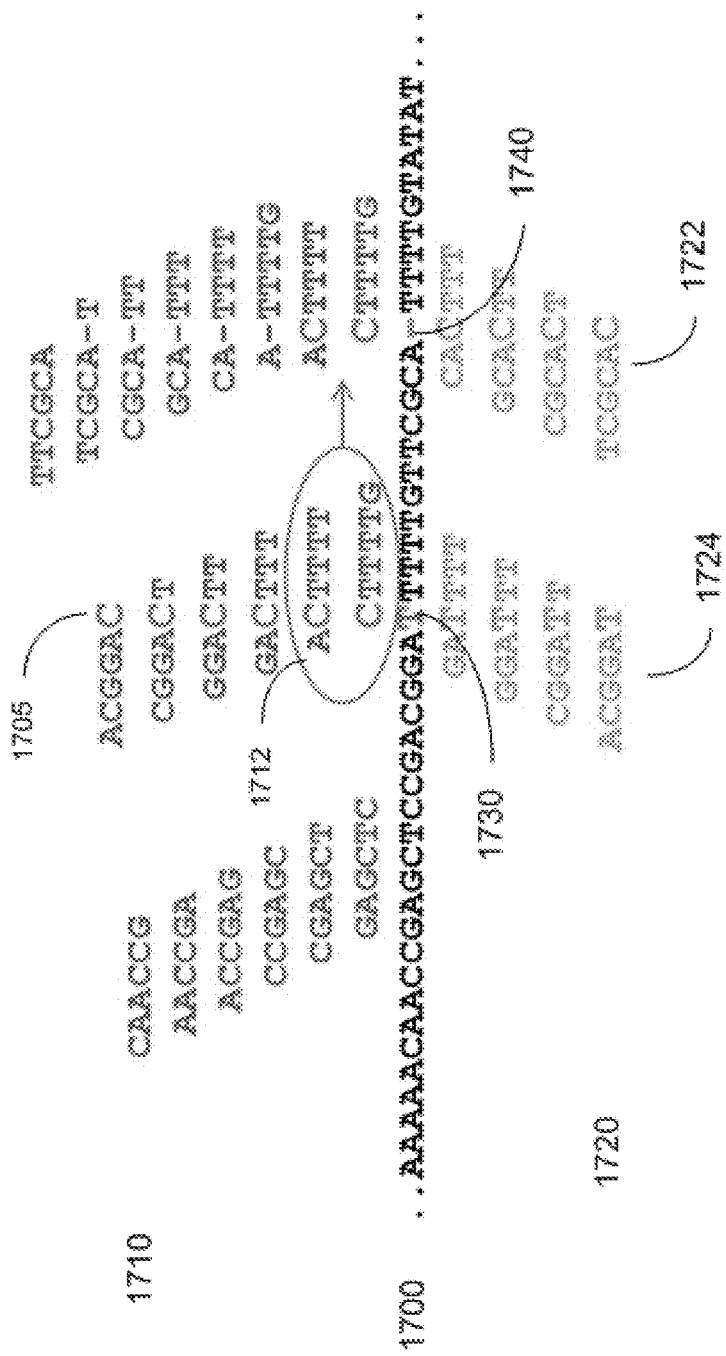

Each point in the plot represents a single primer partition measurement. Each cluster in the figure is a collection of dye intensity readings from primer partitions that correspond to the same partition. In this experiment, each partition corresponds to a single primer oligo sequence. The clusters are colored by the primer identity.

FIG. 3B: Four Dimensional Dye Profile Clusters—Colored by Assay Intensity

FIG. 3B shows the same data as in FIG. 3A but is instead colored by the assay dye intensity measured for each partition. Darker clusters showed brighter assay fluorescence.

FIG. 4A: Assay Intensity Clusters by Sequence Position

FIG. 4A is a scatter plot showing the assay intensity data from a sequencing experiment that used the present invention to sequence exon 15 of the BRAF gene in a sample known to contain a mutation. Each point in the plot represents the assay fluorescence intensity for an individual primer partition read by the optical detector. Each point is colored according to the identity of the primer partition. In this experiment, the partition identity and the single primer contained therein are the same. The points in the scatter plot naturally cluster in the y-axis as a function of the mean assay intensity observed among the partitions containing a particular primer. The point clusters labeled as set A are deliberately ordered about the X axis by the position of their corresponding primer with respect to the final consensus sequence assembly for this target. Set A contains all of the point clusters corresponding to primer partitions that were called as being positive for the sequencing assay. Set B contains all of the point clusters corresponding to primer partitions that were called as being negative for the sequencing assay. The clusters in set B are ordered randomly about the X axis and only represent a random sample of the entirety of assay-negative drops from the experiment. Region C represents our "no call zone" which delineates an assay intensity range wherein assay calls will not be made for primer partitions.

FIG. 4B: Assay Intensities of Primers Containing 3 Degenerate Bases

FIG. 4B is identical to FIG. 4A with the exception of circles surrounding all of the point clusters that represent primer partitions that contained primer oligos that had at least 3 degenerate bases used in their manufacture.

FIG. 5: Reference-assisted Assembly of BRAF Target

FIG. 5 depicts the reference-assisted assembly process that was performed by the assembly software for an amplicon representing exon 15 of the BRAF gene. The wild type sequence "D" was used as the reference for the comparative assembly process. In the figure, only a subsequence of the full reference sequence is depicted. The sets of primers that yielded positive assay calls, sets "A" and "E" were used to initialize the hypothesis space of potential mutations with respect to the wild type. Positive primer "G" was found to align to the reference sequence at the location near set "E" within an edit distance of 1 while aligning at the location near set "A" with a larger edit distance of 2. However, the hypothesis that is generated by the consensus of set "A" was found by the software to have a much higher likelihood of being correct. The software used both the positive set "E" combined with the negatively binding primers of set "H" to form a consensus in that region of the reference that matches the wildtype and with far higher likelihood of being correct than the G/A mismatch hypothesized by primer "G". The final consensus sequence that was called for this target is listed in sequence "I" and contains the correctly called 2-nucleotide substitution mutation from the sample as corroborated through the Sanger sequencing method. This illustrates the basic steps of the reference assisted assembly; look for alignments against the reference sequence for every primer within some edit distance threshold, use the overlap relationships with other positive and negative primers to rank the candidate alignments and do this for every base position in the reference sequence. Then choose the maximum likelihood hypotheses at every position of the reference. If any primers are left outside of the final collection of winning hypothetical consensus sequences, then they are compared with other primers to attempt a reference-free assembly of a potential insert with respect to the reference (this micro-assembly step is not illustrated here). Figure discloses SEQ ID NOS 1-4, respectively, in order of appearance.

FIG. 6A: Example of Multiplexed Primer Partitioning

FIG. 6A depicts two examples of multiplexed primer partitions. Both partitions, A and B, contain exactly 10 distinct primers. The primers are numbered by their identifiers; their oligo sequences are not depicted in any way. The primer identified as number 1 appears in both partitions and is the only primer held in common between the two partitions.

FIG. 6B: Positive and Negative Outcomes for Multiplexed Partitions

FIG. 6B illustrates the means by which a multiplexed partition could yield either a positive or negative assay call. FIG. 6B adds the detail of multiple target molecules (or amplicons) that are assumed to have been previously injected into the partition. Partition A, for example, shows three instances of an amplicon molecule that is binding to three instances of the oligonucleotide for primer number 1. Partition B shows three distinct primers, each binding to a third of the available target molecules. Partitions A and B would both yield a single assay-positive call. Partition C illustrates the only means by which a partition may yield an assay-negative call: if and only if all of the primers contained therein negatively hybridize.

FIG. 7A: Results of 5-plex Experiment

Assay results are shown in FIG. 7A. Results are shown as standard deviation distance from the mis-matched-assay-primer signal ({[fluorescence]−[average fluorescence of mis-matched-assay-primers]}/[standard deviation mis-matched-assay-primers]). Combining assay-primers did not interfere with assay performance and results remained consistent throughout the primer-assay sets. Sets containing matched-assay-primers generated consistently high signal across all combinations and sets containing mis-matched-assay-primers generated consistent low signal regardless of the number of assay-primers included in the combined sets.

FIG. 7B: Results of 10-plex Experiment

Assay results are shown in FIG. 7B. As with the 5 assay-primer set experiment combining assay-primers did not interfere with assay performance and results remained consistent throughout the primer-assay sets with sets containing matched-assay-primers generating consistently high signal across all combinations and sets containing mismatched-assay-primers generating consistent low signal regardless of the number of assay-primers included in the combined sets.

FIG. 8: Degenerate bases in primer oligonucleotides

FIG. 8 illustrates some options for adding degenerate bases to primers.

FIG. 9: Temporal Segmentation Based on Contradiction Rate

FIG. 9 shows the rate at which primer partitions seen more than once within a fixed window in time have contradicted themselves in terms of assay state. The vertical bars that intersect the local minima in the contradiction rate mark the temporal boundaries between primer partition measurements that represent different PCR-partitions.

FIG. 10: Partition Vector for a Reference Sequence

FIG. 10 illustrates the software mechanism used to precompute a partition vector for a single reference sequence. A partition vector stores the expected assay outcomes for every partition in the primer partition library with respect to the corresponding wild type reference sequence. A depicts a reference sequence corresponding to the wild type of some region of interest captured by one of the PCR primer pairs in the PCR partition library. Each of the partitions C, D and E are depictions of a subset of the actual multiplexed primer partitions in a sequencing library. Each of C, D, and E are labeled in the upper right corner with a "+" or "−" to signify the expected assay outcome for that partition with respect to the reference sequence A. Table B depicts the partition vector for reference sequence 1000. The left column in table 1010 contains the identifiers for each of the partitions in the sequencing library. The right column in table 1010 shows the value that a bit is set to depending on the expected assay outcome for the corresponding partition. Partitions 1020, 1030, and 1040 have arrows pointing to the rows in table 1010 that correspond to their identifier. Partitions 1020 and 1040 are expected to yield positive assay calls when tested against this wild type. Partition 1030 is expected to be assay-negative. In the positive partitions 1020 and 1040, the primer that is the source of the positive signal is highlighted in blue and italicized. The subsequences with reference sequence 1000 that match the positive primer sequences from partitions 1020 and 1040 are also highlighted in blue and italicized. Figure discloses SEQ ID NO: 5.

FIG. 11: Process for Computing Mapping Scores

FIG. 11 illustrates the software process used to compute mapping scores for a cohort of primer partitions. The cohort of partitions labeled as set "1110" is assumed to be a set that has just previously been associated by the temporal segmentation process. Each circle in set 1110 contains a "+" or "−" to represent that partitions assay call. Table "1120" is a bit vector of length equal to the total number of partitions in the sequencing library. The partitions in "1110" are arranged to align with partition identity order. Table 1140 shows the partition identifiers. Table 1130 represents the collection of partition vectors for all of the reference sequences for the sequencing panel being run during the experiment. Column "1132" shows the Hamming distances between each of the reference vectors in "1130" versus the cohort vector in "1120". Note that some of the columns in "1120" are blank. That signifies a partition that happened not to be observed within the cohort. The bit positions within both the cohort vector "1120" and all of the reference vectors in 1130 are masked prior to computing the Hamming Distances. The rectangle "1134" selects the best matching reference sequence since it has the smallest Hamming distance.

FIG. 12: Clustering of Cohort Vectors

FIG. 12 illustrates the software process of clustering cohort vectors in the case where a reference sequence is either unavailable or a sufficiently strong match was not found. "1250" labels a collection of unclustered cohort vectors. 1210, 1220, 1230, and 1240 label the Hamming distance calculation that is made directly between a pair of cohort vectors. This distance calculation is performed for all pairs of cohort vectors in "1250". The cohorts are then clustered agglomeratively and results in the clustered vector sets in "1270". "1260" marks the only bits in the partition vectors that have observed partitions in both vectors and these are the only bits used in the distance calculation.

FIG. 13: Negation Within a Cohort

FIG. 13 illustrates the software process whereby the assay-negative partition data "1310" from a cohort is leveraged to negate the artificial false positive primers resulting from the assay-positive partitions "1300" from the same cohort. The software has precomputed the set intersections between all pairs of partitions. It uses this to negate any primers that are found in both positive and negative partitions within the same cohort. The negative embodiments of primers that are used to negate their positive counterparts are italicized. Primers in the positive partitions that survive the negation process are not crossed out in the figure.

FIG. 14: Negation Between Cohorts

FIG. 14 illustrates another negation step performed by the software wherein the negative partitions from one cohort are used to negate the false positive primers in a different but related cohort. This process is identical to that illustrated in FIG. 13 with the exception that the relatedness between the cohorts must be established first, either by clustering them together or directly or indirectly by way of mapping to the same reference sequence. In this figure, negative primers are either italicized if they negate positives within the same cohort or underlined if they negate positives in the other cohort. In this figure, the two cohorts "1420" and "1440" are associated via mapping to the same reference sequence "1400". Figure discloses SEQ ID NO: 5.

FIG. 15: Illustration of Gapped Primers

FIG. 15 illustrates several examples of gapped probes. Section A lists three different gapping schemes that span sequence contexts ranging in length from 6 base pairs to 9 base pairs. Every gapping scheme in section A uses exactly 6 designate bases, resulting in a total addressable complexity of 4096 distinct designate hexamer patterns. Section B illustrates the utility of two complementary gapping schemes. In particular, they allow a single probe with only 6 designate bases to span tandem repeat and homopolymer contexts that are as large as the combined length of the gapped oligo itself in this case 9 nucleotides. Figures discloses SEQ ID NO: 6.

FIG. 16: Illustration of Assembly Process

FIG. 16 illustrates the de novo assembly process. In this illustration a general embodiment of a primer partition library that contains primer sequences that adhere to a mixture of gapping schemes is assumed. Negative evidence is leveraged at several stages of the process in order to prune false branches in the overlap graph, eliminate false fill-ins within the assembly scaffold as well as eliminate false positive mutation hypotheses. Figures discloses SEQ ID NOS 7, 6, and 8, respectively, in order of appreareance.

FIG. 17: Illustration of basic micro-assembly using positive and negative evidence.

(1710) Positively binding probes are colored in blue. (1705) A hypothetical C/T polymorphism is corroborated by several overlapping hexamer probes that tested positive for the assay. (1712) A subset of the probes that corroborates the C/T polymorphism also supports an alternate hypothesis of a 1712 insertion polymorphism. The 1712 insertion hypothesis is contradicted by the other positive probes that align well to the same region of the reference sequence. (1722) The C insertion hypothesis is further contradicted by several probes that tested negative for the assay and happen to align exactly to the hypothetical C-insertion within the reference context of that hypothesis. In this way, negative evidence is antithetical to a false-positive C-insertion hypothesis. This illustrates, in a simplified manner, the general utility of negative evidence. Further, in (1724) we see that negative evidence is antithetical to the reference sequence itself, which further corroborates the C/T polymorphism hypothesis. This illustrates the general ability of negative evidence to promote true positive hypotheses by negating, or weighing against the wild-type or "reference" allele. Figures discloses SEQ ID NO: 9.

Figure 18:
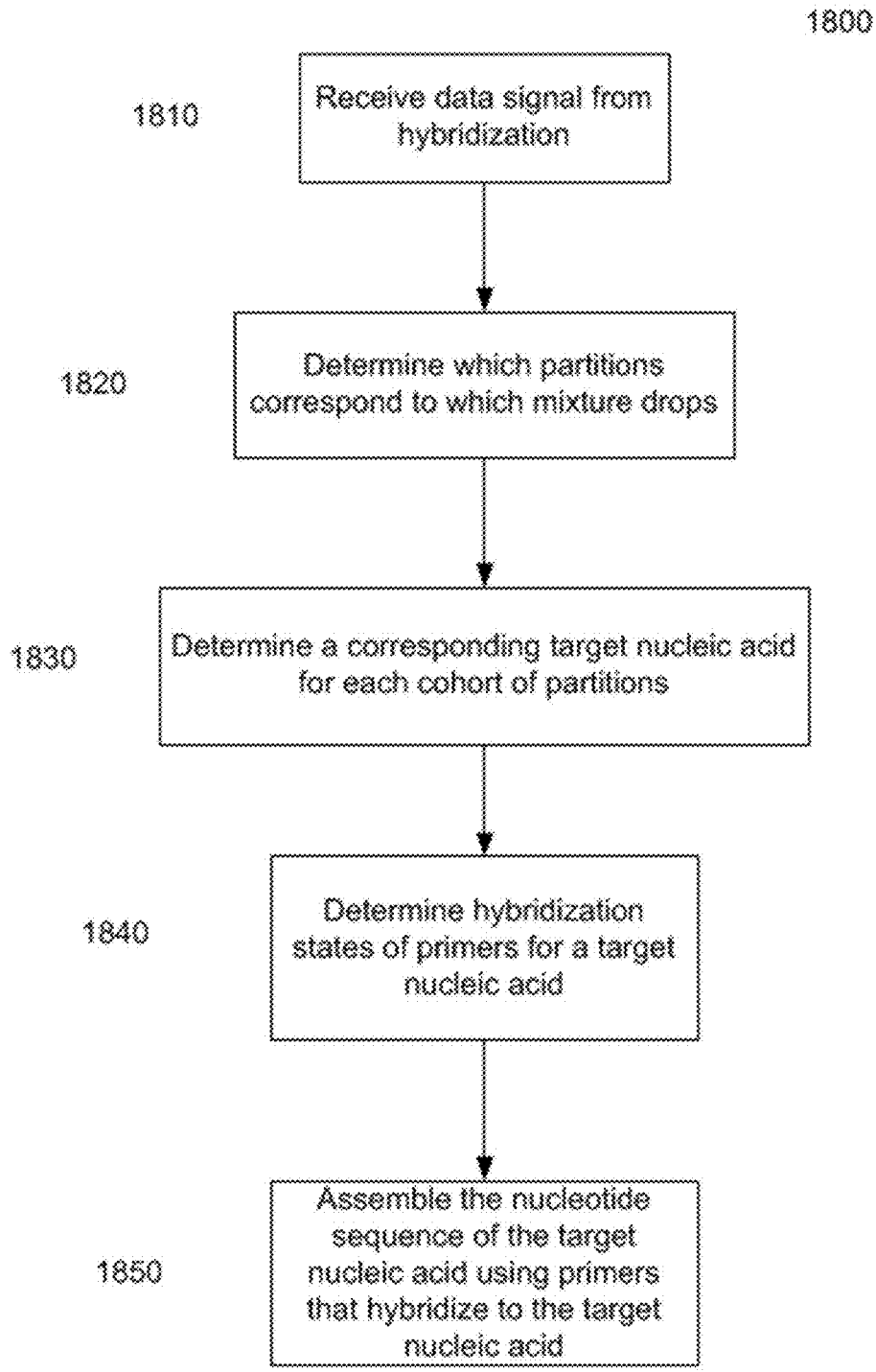

FIG. 18 is a flowchart illustrating a method 1800 for determining a nucleotide sequence of the target nucleic acid according to embodiments of the present invention.

Figure 19:
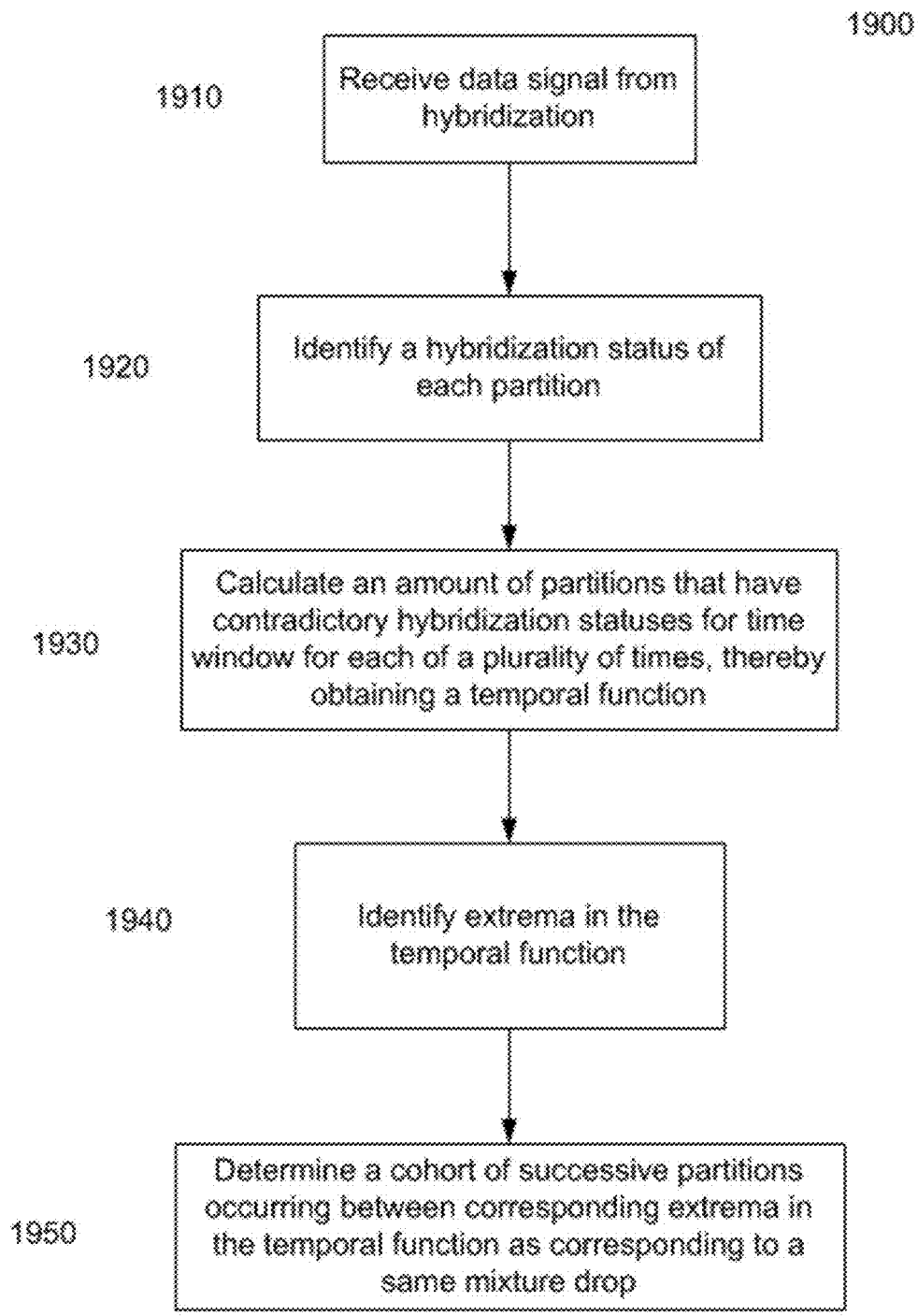

FIG. 19 is a flowchart of a method 1900 of identifying primer/target nucleic acid partitions as being generated from a same target nucleic acid partition mixture drop.

Figure 20:
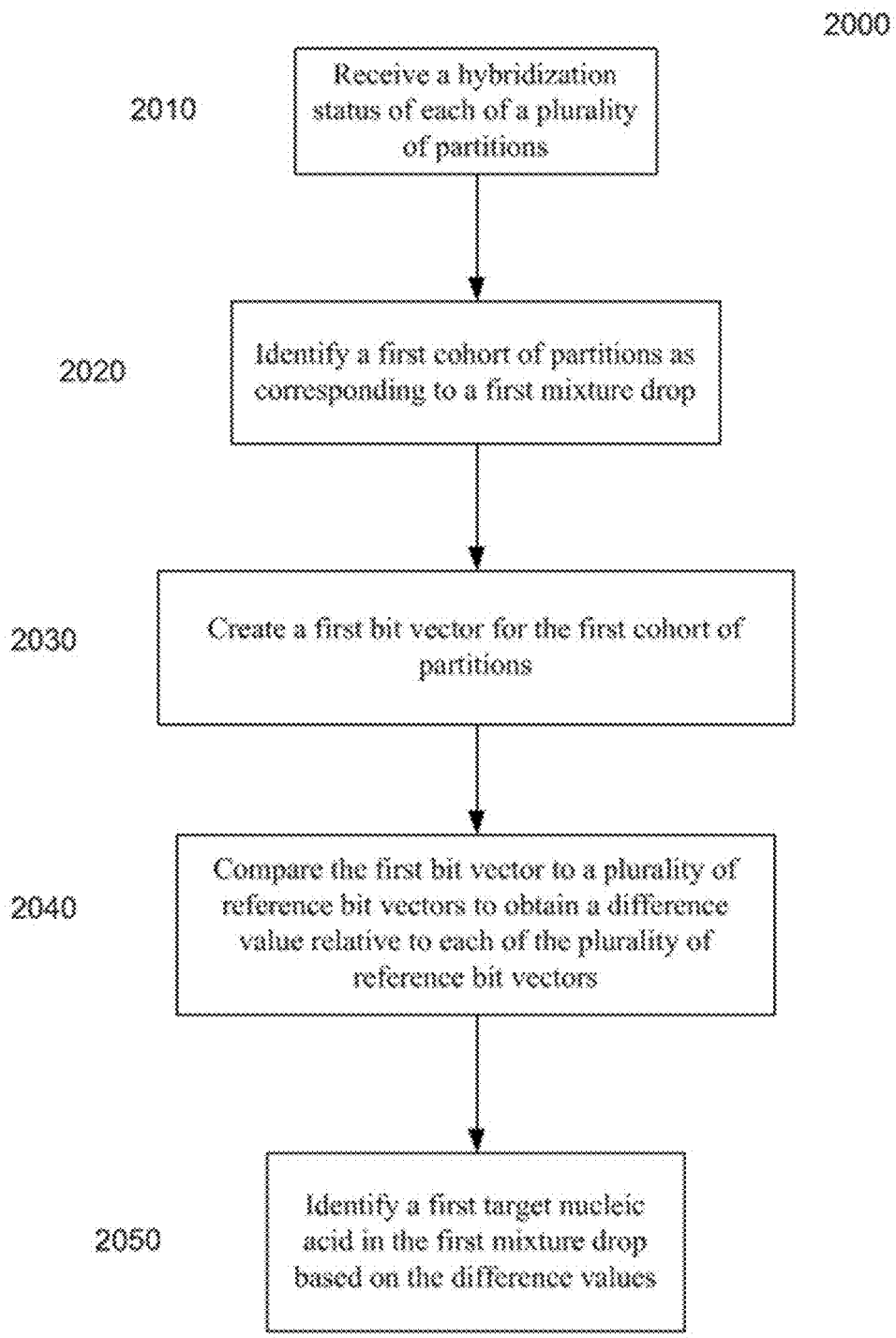

FIG. 20 is a flowchart of a method of identifying a mixture drop as including a target nucleic.

Figure 21:
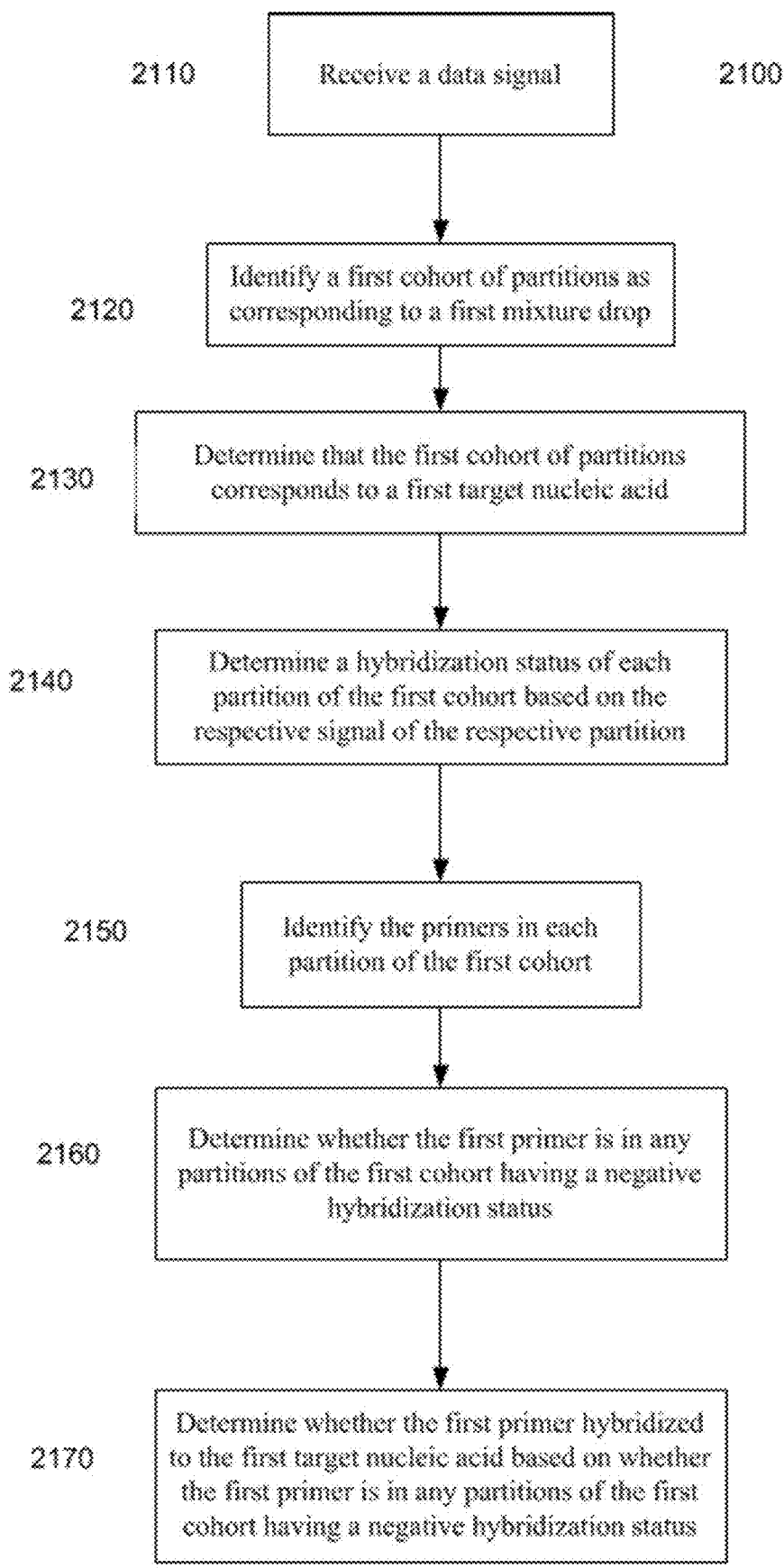

FIG. 21 is a flowchart of a method of determining a hybridization state of a primer for a mixture drop.

Figure 22:
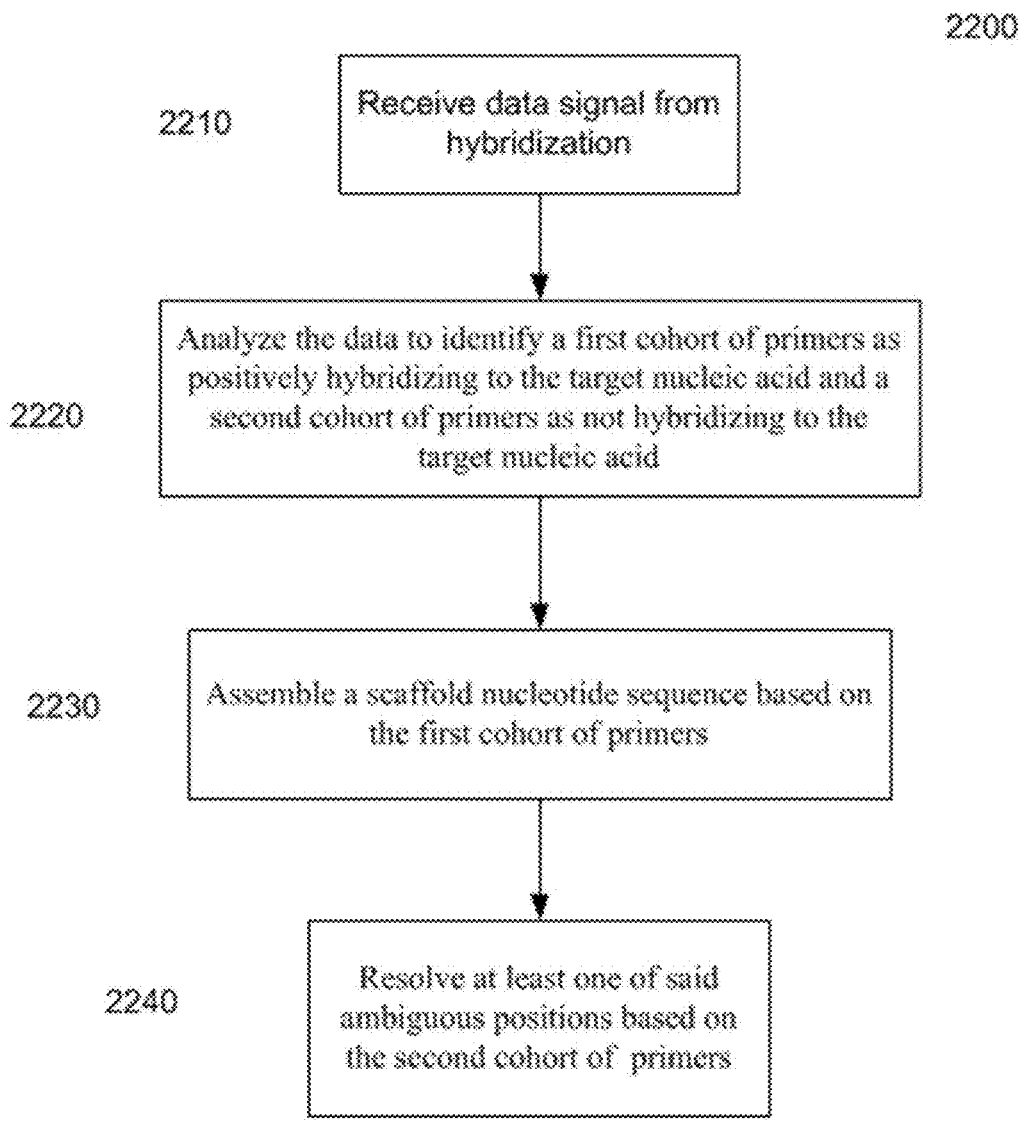

FIG. 22 is a flowchart of a method 2200 of determining a nucleotide sequence of a target nucleic acid based on hybridization of primers according to embodiments of the present invention.

Figure 23:
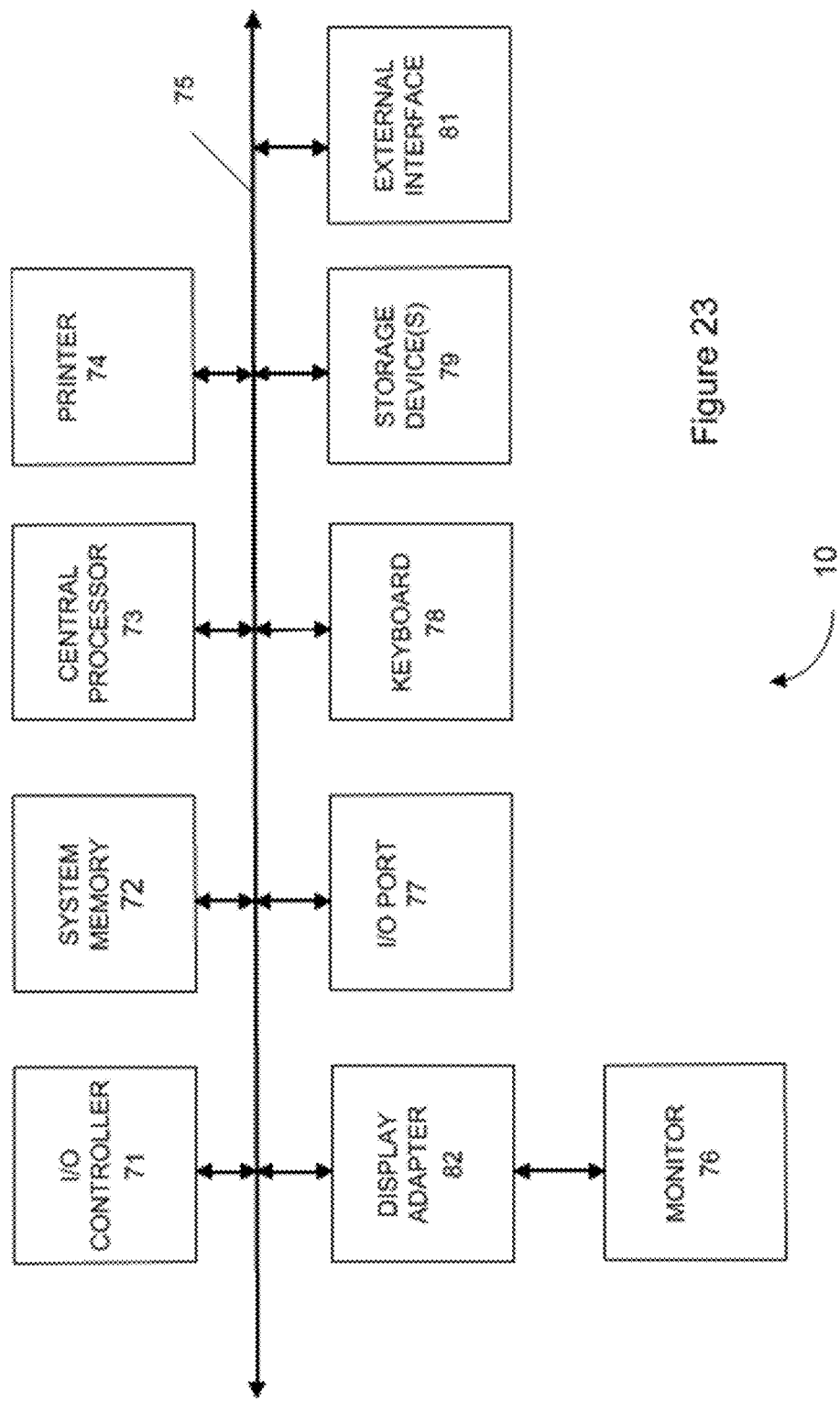

FIG. 23 illustrates a computer system

DETAILED DESCRIPTION OF THE INVENTION

Introduction

Provided herein are methods for determining a nucleotide sequence of a target nucleic acid based on primer hybridization to the target nucleic acid, wherein hybridization indicates that the nucleotide sequence complementary to the primer is present and lack of hybridization of the primer indicates the absence of the precise complement of the primer. As described herein, the method is performed in partitions (for example, in drops in an emulsion), and in particular involving generation of (i) partitions comprising the target nucleic acid ("target partitions") and (ii) partitions comprising one or more primer ("primer partitions") and combining portions of the target partitions with primer partitions on a one-for-one basis to generate a hybridization reaction in merged partitions ("reaction partitions"), which can subsequently be assayed for hybridization.

In some aspects, the methods involve combining multiple primers having different sequences in the same primer partition that subsequently is combined with a portion of a target partition. The hybridization reaction is then assayed for the presence or absence of hybridization of any of the primers. Combined primer partitions can be designed such that hybridization of various combinations of partitions can be deconvoluted to generate a logical sequence of the target based on the hybridization of the various multiple primer sets. Design of multiple primer sets is described in detail below.

Also provided herein as libraries of primer partitions as describe herein as well as systems for performing the methods and analyzing the results.

While in some circumstances the target nucleic acid nucleotide sequence will be completely unknown, in many embodiments, the general structure and sequence of the target nucleic acid sequence will be known, however, the precise nucleotide sequence will not be known. For example, a particular genetic biomarker sequence will be known, but it will not be known what exact genetic variant an individual is carrying. The methods describe herein are particularly useful for determining the precise genetic variant of a known genetic sequence in a sample, e.g., from an individual.

Sequencing by Hybridization Overview

The methods described herein rely on hybridization, or lack thereof, of a large number of different primer sequences to a target nucleic acid. By detecting hybridization of overlapping primers and absence of hybridization of primers of similar but different sequence, one can predict the nucleotide sequence of a target sequence. One example of sequencing by hybridization is depicted in FIG. 17, which shows a predicted target nucleic acid in bold and a series of different variant primers. Only fully complementary primers bind to the target nucleic acid whereas primers that are not fully complementary do not bind. In FIG. 17, primer sequences above the predicted target sequence have been identified in the assay as hybridizing to the target nucleic acid whereas primer sequences below the target sequence have been identified as not hybridizing to the target nucleic acid. While the target nucleic acid in FIG. 17 is depicted as a single-stranded sequence in the same orientation as the primers, it will be appreciated that in fact the primers will hybridize to their complementary sequences in the other strand of the target.

Primers in partitions may be used to determine the sequence of nucleic acids as described in PCT Publication No. WO2012/078710. For example, the assay can comprise incorporating a detector (for example the detector may comprise a fluorescent label) into a target nucleic acid and adding this target nucleic acid into the primer partitions. In addition the primer partitions may comprise a polymerase enzyme (for example Klenow fragment (New England Biolabs® Inc.), Taq DNA polymerase (QIAGEN), 9°N™ DNA polymerase (New England Biolabs® Inc.), Deep Vent™ DNA polymerase (New England Biolabs® Inc.), Manta DNA polymerase (Enzymatics®), Bst DNA polymerase (New England Biolabs® Inc.), and phi29 DNA polymerase (New England Biolabs® Inc.), reverse transcriptase (New England Biolabs) or another commercially available polymerases), dNTP, a nucleic acid inhibitor (for example the inhibitor may comprise a quencher attached to a nucleic acid sequence matching a fluorescently labeled target nucleic acid), dye labels and salt buffers requires for the polymerase enzyme reaction (salt buffer needs are polymerase specific and include components such as for example KCL, Tris-HCl, and MgCl).

The primer combinations used may be designed such that they act in concert in a single assay. For example, primers may vary in length so that they match in melting temperature. For example the following primers: GACTGTCA, AGGCGTT, ATTGAACTT, ATTTTAACTT (SEQ ID NO: 10)vary in length and have similar melting temperature so that they all can hybridize to the nucleic acid target at the same temperature and assay conditions. In other embodiments gaps are introduced into primer sequences using universal bases. In yet other embodiments, gaps are introduced by a mixture of methods including but not limited to degenerate bases and universal bases.

The precise number of different primer sequences used to determine a target nucleic acid sequence will be a function of the length and complexity of the target sequence, and the number of designated (discussed further below) nucleotides and other positions in the primers. Once the results of hybridization of the primers is known, deconvoluting methods and software can be used to logically derive the target nucleic sequences based on the knowledge of what sequences are present or absent, which is derived from the hybridization.

Much attention has been given to the optimal selection of these probe sets, their combined sequence complexity, and the optimal surface conditions in an effort to maximize hybridization signal as well as to maximize the resolvable size of the target molecule and this information can be applied in the present invention. See, e.g., R. Drmanac, et al., Science 260:1649-1652 (1993); R. Drmanac, et al., J. Biomol. Struct. Dyn. 5: 1085 (1991); PEVZNER, et al., J. BIOMOLECULAR STRUCTURE & DYNAMICS 9(2): 399-410 (1991); B. HUDSON: "An Experimental Study of SBH with Gapped Probes" TECHNICAL REPORT CS-99-07, DEPT. OF COMPUTER SCIENCE, BROWN UNIVERSITY, April 1999; PCT Patent Publication No. WO 2000/022171.

In general, when a "primer" is said to be present in a partition or reaction mixture, it is intended that a number of copies of that primer is included in that partition unless the copy number is specifically referred to in the text. For example, if two primers are said to be in a partition, a large number of copies of each of the two primers is in fact included in the partition.

Generation and Use of Primer Sets

Each primer hybridization reaction is determined within a partition. In some embodiments, multiple different (i.e., having different sequences) primers are included in each primer partition. Hybridization is determined as presence or absence of hybridization.

In some embodiments, the multiple different primers ("sets") are placed within each partition. Sets of primers can be selected such that the sets are not random, but instead each contains a known number and identity of primers. The number of primer sets will generally be at least 50, 100, 200, 500, 1000, 10000, 50000, 100000, 200000, or more. For example, 1024 different sets of primers can be provided where each set contains ten different primers. Each set may, but does not necessarily have to, include the same number of primers. In some embodiments, each primer occurs in multiple sets. An example of this is depicted in FIG. 2 wherein two classes of multiplexed emulsions are shown, each containing 10 distinct probes. The probes are numbered only to distinguish them from one another in the set and act as identifiers across partitions in the figure.

The primers added to primer partitions may have any nucleic acid sequence. For example, the nucleic acid sequences may have between 4 to 15 nucleotides. In another example multiple primers may be combined together in a primer partition. For example, a combination of primers may include a common nucleic acid sequence and a variable nucleic acid sequence. One example of a primer combination may be NACTTCA where N designates a variable sequence consisting of A, G, C, or T for the following primer combination: AACTTCA, CACTTCA, TACTTCA, and GACTTCA. Other primer combinations may include multiple variable sequences of any type, for example NNNATGCT, CTNGGN, or GTCVTGC where V is A C or G. In another example primers that differ in length and/or sequence may be combined together such as, but not limited to: AACTTCAGG, GTCGC, and GGTCACT. In another example primer combinations may include primers comprising of natural nucleotides and chemically modified nucleotides. For example primers may include Locked Nucleic Acids, fluorescent labels (for example Cy5, Cy3, FAM, MAX, TAMRA and others), biotin, nitroindoles, deoxyInosines, deoxyUridine or other modifications.

In some embodiments, no intersection of any two primer sets contains more than one primer. This type of relationship is depicted in FIG. 2 wherein partitions A and B share only the probe identified as number "1" in common.

When a large number of different primers are tested against a target nucleic acid, generally a significant portion (e.g., >20%, >30%, >40%, >50%, >60%, >70%, >80%) will not hybridize to the one or more target nucleic acid present in a reaction partition. This is at least in part because the complexity of a given target sequence is much less than the complexity of the series of primers tested. Accordingly, if each primer was tested in individual partitions, most partitions will provide only a limited amount of information *(one primer did not hybridize). However, by combining multiple primers in partitions and testing the primers in a partition simultaneously, it is possible to gain considerably more information for each partition (e.g., 2, 3, 4, 5, 6, 7, 8, 9, etc., different primers do not hybridize to the target).

In some embodiments, the series of primers include at least 40, 50, 60, 70, 80, 90, or 100% of the possible combination of primer sequences for the designated nucleotides. For example, there are 4096 different combinations of hexamers where all nucleotides are designated.

The number of primers in a partitions can be the same (e.g., 1, 2, 3, 4, 5, 6, 7, 8, 9, 10, 11, 12, 13, 14, 15, 16, 17, 18, 19, 20, or more per partition) or the number of primers can vary between partitions. As discussed further below, the identity of the particular primer or primers in a partition can be determined by inclusion of one or more specific spectroscopic characteristics in the partition, wherein each primer set is represented by a different characteristic.

In some embodiments, all primers in the set have the same number of designated nucleotides (e.g., each primer has six designated nucleotides). More frequently, it will be desirable that the primer set comprise primers of differing number of designated nucleotides (e.g., some primers having 5 designated nucleotides, some primers having 6 designated nucleotides, some primers having 7 designated nucleotides).

Hybridization is determined as presence or absence of hybridization in the partition. Thus, in an example where the partition contains ten primers, if for example one of ten, or nine of ten, of the primers in the primer partition hybridizes to the target nucleic acid, the partition is scored as hybridizing, whereas if none of the ten primers hybridize, the partition is scored as not hybridizing. Examples of the types of aggregate outcomes measurable are depicted in FIG. 3. In case A, only one of the primers within the drop binds to the target molecule(s), and therefore the partition in its entirety appears as a positive. In case B, primers bind to the target and again, the emulsion in its entirety appears to be positive. Only in case C, where none of the primers binds to the target, does the partition appear to be in a negative state. The negative results (lack of hybridization) can be used, such as in case C, to counter false positives that can occur for example in cases such as A and B. Furthermore, positive probes can be verified based on the distinct overlaps between two partitions having a known overlap of primer(s), e.g., as depicted in FIG. 6A. Negative results are also helpful for ruling out otherwise logical alternative sequences. For instance, in part 1722 of FIG. 17, the negative primers such as CACTTT indicate that the alternative of a "C" in the indicated "–" of the target sequence does not in fact exist (otherwise CATTT would have hybridized).

In some embodiments, one or more primers use in the partitions are "gapped" primers wherein some positions of the primer have a designated nucleotide and other positions (i.e., gaps) are degenerate or otherwise allow for hybridization at that position to any base. Thus a gapped primer will include regions of designated nucleotide(s) which, under the hybridization conditions, selectively base-pair by A-T or G-C pairing or the like, and regions of universal nucleotide(s) which display degeneracy (i.e., as a mixture of primers having either A, C, T and G at that position), or substantially no selectivity between nucleotides. Exemplary universal nucleotides include but are not limited to 5-nitroindole, 3-nitropyrrole and deoxyinosine. Design of gapped primers is described in, for example, US Patent Publication No. 2003/0064382.

In addition to the primer sequences described above, additional nucleotides can be added to the primer sequence, generally at the 5' end, to adjust the melting temperature (Tm) of the primers. In some embodiments, the set of primers used will be Tm "balanced," that is the Tm of individual primers in the set that are lower than the mean Tm of the set will be adjusted upward by addition of one or more nucleotide (e.g., degenerate, universal or designated) at the 5' end of the primer, such that the resulting primer set has a more narrow Tm range than the initial primer set. This allows use of all of the primers in the set to function in hybridization conditions of the assay. In some embodiments, no more than 0%, 1%, 5%, 10%, 15%, or 20% of Tms of the primers in the set differ by more than 1, 2, 3, 4, 5, 7, 10, 15, or 20° C. from the mean Tm of the primers of the set.

FIG. 15 illustrates several possible exemplary gapping patterns where six nucleotide positions have been designated, i.e. are fixed, in the primer sequence. In some embodiments, the series of primers comprise a mixture of gapped and ungapped primers. In some embodiments, at least 10, 20, 30, 40, 50, 60, 70, 80, or 90% of the primers in a series are gapped.

A mixture of gapping patterns in the primer set can achieve one or more of the following:
 The assembly process can span longer, otherwise repetitive stretches of nucleotide sequence;
 Longer target sequences can be unambiguously assembled due to overall increase in complexity of the primer sequence set, i.e., increasing the probability of any given primer hybridizing and being unique within the target nucleic acid;
 The number of target partitions does not need to increase to compensate for the increased complexity of the primer library.

Partition of Primers, Spectroscopic Characteristic

Partitions as described herein can contain additional markers to identify reagents (e.g., primers) within particular partition. For example, in some embodiments, one or more marker reagent can be inserted into each different primer partition such that each primer set is represented by a pre-determined and known unique signal based on the one or more marker reagent in the primer partition. By allowing for a unique detectable characteristic for each primer set used, one can thereby determine which primer set resulted in hybridization. For example, in some embodiments, presence/absence of hybridization (e.g., as described elsewhere herein) and the marker characteristic are detected for each reaction partition, with the marker characteristic indicating the identity of the primers in the reaction. In a simple example, if two sets of primers are used and primer set A includes marker characteristic X and primer set B includes marker characteristic X, then the result of "hybridization and characteristic X" indicates that the primers of primer set A hybridize and the result of "no hybridization and characteristic B" indicates none of the primers of set B hybridize. One can then look up the precise primer sequences of primer set A and B because the marker characteristic is predetermined and unique.

In some embodiments, the marker characteristic is generated by the presence of one or more spectroscopic substance. In some embodiments, the spectroscopic substance comprises one or more selectively absorbent molecule. A "selectively absorbent molecule", as used herein, is a molecule that absorbs certain characteristic colors or wavelengths of light while allowing other colors or wavelengths of light to pass or transmit through the molecule when a broadband light source is directed at the molecule. One of skill in the art will know and appreciate the numerous selectively absorbent molecules that may be used to comprise the selectively absorbent substance/constituent according to the present invention, including but not limited to, those commercially available from Exciton (Dayton, OH) and QCR Solutions, Corp. (Port St. Lucie, Fla.).

In another aspect of this embodiment, the spectroscopic substance comprises one or more fluorescent molecule. A "fluorescent molecule", as used herein, means a "fluorescent material" or "fluorescent label" or "fluorophore" or "fluorescent dye", each of which as used herein may be a fluorescent molecule, a fluorescent semiconductor nanoparticle (referred to as a "quantum dot"), or a chelated lanthanide or lanthanoid, having the ability to absorb energy from light of a specific wavelength, and then emit this energy as fluorescence having another specific wavelength characteristic for the particular molecule or quantum dot. In this manner, the fluorophore will facilitate the final assay readout indicating the presence or absence of a particular target of interest in the sample.

The particular fluorophore employed is not critical to the present invention. Fluorophores are known in the art and are described, for example, by Marras, "Selection of Fluorophore and Quencher Pairs for Fluorescent Nucleic Acid Hybridization Probes", In: V. Didenko, ed. 2006. Fluorescent Energy Transfer Nucleic Acid Probes: Designs and Protocols (Methods in Molecular Biology, vol. 335). New Jersey: Humana Press Inc., pp.3-16. Examples of fluorophores that may be employed in the present invention include, but are not limited to, those described by Marras 2006 and further described herein below. One of skill in the art will appreciate the various fluorescent dyes that may serve as fluorescent molecules and that may be employed in the present invention and which are available from various commercial vendors.

A wide array of fluorescent dyes may be used to label primer partitions. Fluorescent dyes are commercially available from various vendors. Some examples include but are not limited to: Cyanine dyes (various vendors e.g. GE Healthcare, AAT Bioquest, Thermo Scientific) for example Cy3, Cy5, Cy5.5, Cy7; Dylight dyes (Thermo Scientific) for example Dylight 550, Dylight 594, Dylight 633, Dylight 650, Dylight 680; Atto dyes (Atto-Tec) for example Atto 610, Atto 647, Atto 680; IFluor dyes (AAT Bioquest) for example iFluor 633, iFluor 647, iFluor 750, iFluor 790; Pycoerythrin and PerCP fluorescent proteins (various vendors e.g. Life technologies, AnaSpec, Columbia Biosiences); fluorescein and derivatives thereof (e.g., fluorescein isothianate (FITC), carboxyfluorescein (FAM), tetrachlorofluorescein (TET), 2',7'-difluorofluorescein (Oregon Green® 488), Oregon Green® 514 carboxylic acid, and a fluorescein with chloro and methoxy substituents (JOE and 6-JOE)); rhodamine derivatives (e.g., tetramethyl rhodamine (TAMRA), tetramethyl rhodamine iso-thiocyanate (TRITC), tetramethylrhodamine (TMR), carboxy-X-rhodamine (ROX), Texas Red (a mixture of isomeric sulfonyl chlorides and sulforhodamine; Invitrogen™) and Texas Red-X (Texas Red succinimidyl ester, which contains an additional seven-atom aminohexanoyl spacer ("X") between the fluorophore and its reactive group; Invitrogen™), and Rhodamine X); cyanine derivatives (e.g., indocarbocyanine (Quasar® 570, Quasar® 670 and Quasar® 705), Oregon Green® isothiocyanate, and eosin isothiocyanate (EITC)); N-hydroxysuccinimidyl 1-pyrenebutyrate (PYB); N-hydroxysuccinimidyl 1-pyrenesulfonate (PYS); (5-(2'-aminoethyl)aminonaphthalene (EDANS); CAL Fluor® Gold 540, CAL Fluor® Orange 560, Fluor® Red 590, CAL Fluor® Red 610, and CAL Fluor® Red 635 (proprietary fluorophores available from Biosearch Technologies, Inc.); VIC®; HEX® (a 6-isomer phosphoramidite); and NED®.

The concentration of fluorescent dyes required to label primer partitions is dependent on the detection system used. For example dye concentration in primer partitions in sm embodiments range from 10 nM to 1000 nM for the non-protein dyes in the examples listed and from 0.1 ug/ml to 50 ug/ml for protein dyes or dyes that are conjugated to fluorescent proteins. Different detection systems may require higher or lower dye concentrations than the examples provided.

The particular quantum dot (QD) employed is not critical to the present invention. Quantum dots are known in the art and are described, for example, by Han et al., "Quantum-dot-tagged Microbeads for Multiplexed Optical Coding of Biomolecules", Nat Biotechnol (July 2001) vol. 19, pp. 631-635. One of skill in the art will appreciate the various quantum dots that may serve as fluorescent labels and that can be employed in the present invention and which are available from various commercial vendors. Examples of quantum dots (QDs) that may be employed in the present invention include, but are not limited to, the following: cadmium selenide (CdSe) quantum dot nanoparticles (e.g., CdSe Quantum Dot Cores, 480-640 nm emission spectra, Sigma-Aldrich®); cadmium sulfide (CdS) quantum dot nanoparticles (e.g., CdS Quantum Dot Cores, 380-480 nm emission spectra, Sigma-Aldrich®); zinc sulfide-capped cadmium selenide (ZnS-capped CdSe) nanocrystals (e.g., CdSe/ZnS Lumidots™ and CdSe/ZnS NanoDots™, 480-640 nm emission spectra, Sigma-Aldrich®); and cadmium-free quantum dots (e.g., CFQD™, 400-650nm emission spectra, Sigma-Aldrich®).

The particular chelated lanthanide or lanthanoid employed is not critical to the present invention. Lanthanides and lanthanoids are known in the art to comprise the fifteen metallic chemical elements with atomic numbers 57 through 71, from lanthanum (La) through lutetium (Lu). Examples of lanthanides or lanthanoids in chelated form that may be employed in the present invention include, but are not limited to, the following: lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu).

Dyes may be incorporated into a vehicle, such as a droplet, either at the time of droplet formation or after droplet formation using any injection method known and appreciated by one of skill in the art. Dyes may be incorporated during droplet formation by flowing or streaming the desired dye composition as a fluid stream into a droplet-maker design. Droplet-making designs and methods include but are not limited to those described in International Patent Publications WO 2004/002627 and WO 2006/096571, each of which is incorporated herein in its entirety.

According to the method of the present invention, the sample to be tested may be analyzed for spectroscopic intensity measurements of each spectroscopic substance, wherein the spectroscopic intensity measurement of the reference spectroscopic substance may be used to correct the spectroscopic intensity measurement of one or more sample spectroscopic substances. Depending on the application, the spectroscopic properties may comprise: light scattered from a sample to be tested following illumination of the sample to be tested; light emitted as chemiluminescence by a chemical process within the sample to be tested; light selectively absorbed by a sample to be tested following direction of a broadband light source at the sample to be tested; or light emitted as fluorescence from a sample to be tested following excitation of the sample to be tested.

The spectroscopic intensity and wavelength of a spectroscopic substance may be measured by any methods for spectroscopic analysis known and appreciated by one or ordinary skill in the art. Spectroscopic methods that may be utilized in the present invention include, but are not limited to, a laser and photodetector pair system or more complex optics known to those of skill in the art where the path of an optical beam intersects with the path of a spectroscopic substance and the excitation or illumination of the spectroscopic substance is captured by an optical path comprising one or more objective, mirror, and/or lens to direct the light to a photomultiplier tube (PMT) or photosensitive camera. A known fluoroscopy method that will be known and appreciated by one of skill in the art for use in the present invention is the use of flow cytometry instrumentation. As an example, by providing four different dyes at eight different dye concentrations, one can generate $8^4$ (=4096) different unique identifiers, each of which can be used to identify a unique primer set.

The spectroscopic intensity measurements may comprise one or more methods, including but not limited to, light scatter, absorption, chemiluminescence, fluorescent intensity, radiation decay counts, colorimetric, and so forth. Samples to be tested are placed in the path of an excitation energy source such as a light source selected from but is not limited to, lasers, light-emitting diodes (LEDs), arc lamps, broadband light source, and high intensity light bulbs. The spectroscopic substances in the sample to be tested scatter, absorb, chemiluminesce, or fluoresce (also referred to herein as "signal") in the form of light at a wavelength substantially different from the wavelength of the light source. This light from the sample to be tested is then captured by a detector or sensor, which may be selected from but is not limited to, a camera, a charge coupled device (CCD), a complementary metal-oxide-semiconductor (CMOS) (alternatively referred to as a complementary-symmetry metal-oxide-semiconductor (COS-MOS)), one or more individual photodiodes, photodiode arrays (PDAs), avalanche photodiodes (APDs), avalanche photodiodes arrays, photomultiplier tubes (PMTs), or photomultiplier tube arrays.

Known optical or electronic means may be optionally used to amplify the light from the light source and/or the light from the sample to be tested and/or to separate one or both into its component wavelengths. Selecting a reference spectroscopic substance and one or more sample spectroscopic substances for a particular sample to be tested such that each spectroscopic substance scatters light, selectively absorbs light, emits light in the form of chemiluminescence or fluorescence, depending upon the spectroscopic substance and particular application, at substantially different wavelengths allowing for easier separation of the respective wavelengths. The difference between the reference spectroscopic substance's expected value and measured value can be used to quantify the contribution of "noise" to the output, assuming the reference spectroscopic substance and the one or more sample spectroscopic substances are subject to the same measurement conditions (e.g., the power of the light source, detector or sensor noise, humidity, heat, pH of the sample to be tested, and the vehicle that the sample to be tested itself is in). The contribution of "noise" to the reference spectroscopic substance signal should correlate with the contribution of noise to the signal of the one or more sample spectroscopic substances. This correlation may be, and is typically, proportional but could vary linearly, exponentially, or in other manners or functions as well.

Additional information for generation of unique signals for marking individual primer partitions can be found in, e.g., WO2012/135327.

Target Nucleic Acid

Target nucleic acids can be any nucleic acid, natural or synthetic, that can be involved in "Watson-Crick" base pairing. In many embodiments, the target nucleic acid will be DNA or RNA. The nucleic acids can be derived from any organism. In some embodiments, the target nucleic acid can be obtained from one or more eukaryotic or prokaryotic cells can be used in the present invention. In some embodiments, the cells are animal cells, including but not limited to, human, or non-human, mammalian cells. Non-human mammalian cells include but are not limited to, primate cells, mouse cells, rat cells, porcine cells, and bovine cells. In some embodiments, the cells are non-mammalian cells, e.g., avian, reptilian, or other cells. In some embodiments, the cells are plant cells. Cells can be, for example, cultured primary cells, immortalized culture cells or can be from a biopsy or tissue sample, optionally cultured and stimulated to divide before assayed. Cultured cells can be in suspension or adherent prior to and/or during the permeabilization and/or DNA modification steps. In some embodiments, the cells can be from a tumor biopsy or other diseased tissue.

The target nucleic acids can be double- or single-stranded. The target nucleic acids can be of ay length as desired. Generally, longer target nucleic acids will require more complex deconvolution (due to an increased number of logical alternatives that need to be resolved). In some embodiments, the target nucleic acid is 50-1000 bp, 100-500 bp, or 100-250 bp.

In some embodiments, the target nucleic acid comprises, or is a portion of, a genetic biomarker for a disease, prognosis, or indication. As an example, in some embodiments, the target nucleic acid's genotype is associated with a particular cancer or diabetes phenotype. In some embodiments, the biomarker is useful for predicting responsiveness to a drug for treating an indication, including but not limited to, cancer.

In some embodiments, the target nucleic acid is an amplicon, i.e., generated by amplification. Amplification of a DNA locus using PCR reactions is well known (see U.S. Pat. Nos. 4,683,195 and 4,683,202; PCR PROTOCOLS: A GUIDE TO METHODS AND APPLICATIONS (Innis et al., eds, 1990)). Typically, PCR is used to amplify DNA templates. However, alternative methods of amplification have been described and can also be employed. In some embodiments, the double-stranded amplicon can be rendered converted into a single stranded nucleic acid, for example by the methods described in Mitsis et al., *Nucleic Acids Res* (1999) vol. 27, no. 15, pp. 3057-3063; Sanchez, et al., *PNAS* (2004) vol. 101, no. 7, pp. 1933-1938; Chen, et al., "Asynchronous PCR", In: D. Park, ed. 2011. PCR Protocols (Methods in Molecular Biology, vol. 687). New Jersey: Humana Press Inc., pp. 231-243.

In some embodiments, the target nucleic acid is generated in partitions, for example, with a PCR reaction. Partitions comprising target nucleic acids are sometimes referred to herein as "slugs." As shown in FIG. 1, a PCR primer library can be provided that amplifies one or more target nucleic acids. Partitions comprising the appropriate primers to amplify the target nucleic acid are combined with template polynucleotides (e.g., sample genomic DNA, cDNA, mitochondrial DNA, RNA, etc.) and then submitted to thermocyclic conditions for a number of cycles (e.g., 5, 10, 15, 20, 25, 30, or more) to generate an amplicon. As shown in FIG. 1, one way to submit the partitions to thermocyclic conditions is to pass the partitions through a microfluidic channel in a serpentine fashion such that different regions of the serpentine are exposed to different temperatures (e.g., a primer extension temperature, a primer annealing temperature, etc.) of the thermocyclic reaction.

While the methods described above have discussed target nucleic acids in the singular (e.g., one target nucleic acid in the target nucleic acid partition contacted with the primer sets to detect hybridization), in some embodiments, the target nucleic acid partitions comprise more than one target nucleic acids of different sequence. For example, in some embodiments, the target nucleic acid partitions contain two or three or four different target nucleic acids. "Different nucleic acids" in this context means that the target nucleic acids are of different sequences and are not allelic (i.,e., they are from different genomic regions and are not simply two alleles from a heterozygous individual). Each of the different nucleic acids can occur in multiple copies. The use of multiple target nucleic acids is most useful in circumstances where the general target nucleic acid sequence is known (e.g., two known human gene sequences) but the precise allele in an individual is not known. The inventors have found that due to the presence of many negatively-hybridizing partitions for any particular target sequence, the combination of two or three target nucleic acids can be detected and deconvoluted simultaneously. The deconvolution of sequences can be assisted by knowing the general structure of the genes in advance, thereby "anchoring" hybridization of certain primers to a particular target nucleic acid and thereby allowing the deconvolution process to build separate target sequences based on those anchors. Multiple target nucleic acids can be generated, for example, by multiplex amplification of sample nucleic acids to generate multiple target amplicons. Alternatively, separate amplicons can be generated and subsequently mixed. In yet another embodiment, different target nucleic acid partitions will contain different target nucleic acid sequences but resulting hybridization of primers will be determined without prior knowledge of which target nucleic acid was in a particular partition. The subsequent deconvolution can then logically determine which hybridization comes from which target nucleic acid.

Partitions comprising the target nucleic acid (target partitions) can subsequently be combined with primer partitions. In view of the number of primer partitions to be combined with the target nucleic acid, in some embodiments, a portion of the target nucleic acid partition can be combined with a primer partition, such that all desired primer partitions (having different primer sets) are each contacted to a different portion of the target nucleic acid partition, thereby subdividing the target partition and injecting each subdivision into a different primer partition. Methods of injecting droplets into other drops are described in, e.g., US2012/0132288. In some embodiments, a target nucleic acid partition can be divided into at least 50, 100, 200, 300, 400 or more (e.g., 50-1000, 50-500, 50-5000) portions, where each portion is then injected (mixed) with a different primer partition to form a reaction partition. Note that while it is desirable to combine a portion of the target nucleic acid partition with each different type of primer partition, this is generally not required to obtain an accurate sequence. Indeed, it may be common in some embodiments that 5%, 10%, 20% or more primers in a set are not reacted with the target nucleic acid.

Primer Hybridization Assay

As discussed above, the method involves detecting the presence or absence of hybridization of one or more primers in a reaction partition(s). This can be achieved as desired and convenient. In one embodiment, hybridization is detected as described in WO 2012/078710, which is incorporated herein by reference in its entirety. Briefly, this method can involve generating a target nucleic acid comprising florescent label or other detectable substance, e.g., a nucleic acid sequence covalently-linked fluorescent label, and annealed to an inhibitor polynucleotide comprising a quencher such that hybridization of the inhibitor polynucleotide to the target nucleic acid results in quenching of the fluorescent label signal. The detector nucleic acid (i.e., the sequence associated with the target to which the inhibitor polynucleotide hybridizes) can be part of the target sequence or added to the target nucleic acid sequence. A test primer (i.e., one or more primer in a reaction partition) can be combined with the target nucleic acid/inhibitor polynucleotide duplex with a strand displacing polymerase such that if the primer anneals to the target nucleic acid, the polymerase extends the primer and displaces the inhibitor polynucleotide, thereby generating a fluorescent signal, indicating that the primer has hybridized. If the primer does not hybridize, the quencher is not displaced and no (or reduced) signal is detected. Note, in an alternative configuration, the quencher and fluorescent label can also be linked to the target nucleic acid and the inhibitor polynucleotide, respectively. The strand displacement assay can occur isothermally and thus does not require thermocycling. In some embodiments, the target nucleic acid will be generated as an amplicon, having a 5' fluorescent label and optionally, a 3' stem (i.e., double stranded end formed by hybridization of an oligonucleotide to the 3' end) or stem loop.

The detector nucleic acid is an oligonucleotide incorporated into the target nucleic acid to function as a binding site for an inhibitor of the reaction. In one embodiment, the detector nucleic acid is incorporated into the target nucleic acid by ligation of adaptors. In one example of this embodiment, the adaptors are two oligonucleotides analogous to each other. In this example, the adaptors attach the detector to the target nucleic acid. In another embodiment, the detector nucleic acid is incorporated into the nucleic acid sample using PCR primers. In one example of this embodiment, the PCR primers include a target-specific sequence (on the 3' end of the primer), a universal nucleic-acid sequence designed to hybridize to the inhibitor in downstream steps (on the 5' end of the primer), and a detector. See, e.g., WO 2013/122826. In any embodiment, the detector nucleic acid is incorporated into the target nucleic acid sequence and oriented 5' of the target nucleic acid sequence.

In one embodiment, the detector nucleic acid is conjugated to a fluorophore. The fluorophore is a molecule that has the ability to absorb energy from light of a specific wavelength, and then emit this energy as fluorescence in another specific wavelength characteristic for the particular fluorophore. In this manner, the fluorophore will facilitate the final assay readout indicating the presence or absence of a target nucleic acid. The particular fluorophore employed is not critical to the present invention. Fluorophores are known in the art and are described, for example, by Marras, "Selection of Fluorophore and Quencher Pairs for Fluorescent Nucleic Acid Hybridization Probes", In: V. Didenko, ed. 2006. Fluorescent Energy Transfer Nucleic Acid Probes: Designs and Protocols (Methods in Molecular Biology, vol. 335). New Jersey: Humana Press Inc., pp. 3-16. Examples of fluorophores that can be employed in the present invention include, but are not limited to, those described by Marras 2006 and further described herein below. The particular location of the fluorophore in relation to the detector nucleic acid is not critical to the present invention. The fluorophore can be attached anywhere along the detector nucleic acid, including the 5' end, the 3' end or anywhere internally along the detector nucleic acid.

The inhibitor is an oligonucleotide that hybridizes with the detector nucleic acid. The inhibitor functions to allow a signal to be detected only if an oligonucleotide probe matches the target nucleic acid. Hybridization of the inhibitor to the detector nucleic acid takes place in standard reaction buffer, for example, in a DNA polymerase reaction buffer whereby the detector nucleic acid and the inhibitor are mixed in the buffer at the appropriate temperature. In one example, the reaction may be heated to 95° C. for a period of 30 seconds and then chilled to 5° C. below the annealing temperature of the inhibitor.

In one embodiment, the inhibitor polynucleotide is conjugated to a quencher. The quencher is a molecule that functions to decrease, i.e., quench the intensity of the fluorescence by transferring energy from a first fluorophore to a second fluorophore or to a non-fluorescent molecule. The particular quencher employed is not critical to the present invention. Quenchers are known in the art and are described, for example by, Marras 2006. Examples of quenchers that can be employed in the present invention include, but are not limited to, those described by Marras 2006 and further described herein below. The particular location of the quencher in relation to the inhibitor is not critical to the present invention. The quencher can be attached anywhere along the inhibitor polynucleotide, including the 5' end, the 'Y end or anywhere internally along the inhibitor.

In an alternative embodiment, the detector nucleic acid is conjugated to a quencher.

Displacement of the inhibitor in the presence of a hybridizing primer can be achieved with any displacing polymerase. Examples of commercially available polymerase enzymes include, but are not limited to: Klenow fragment (New England Biolabs® Inc.), Taq DNA polymerase (QIAGEN), 9°N™ DNA polymerase (New England Biolabs® Inc.), Deep Vent™ DNA polymerase (New England Biolabs® Inc.), Manta DNA polymerase (Enzymatics®), Bst DNA polymerase (New England Biolabs® Inc.), and phi29 DNA polymerase (New England Biolabs® Inc.).

As noted above, in some aspects the target nucleic acid is generated with a 3' stem or stem loop. The stem loop portion will comprise a sequence forming the first half of the stem, followed by a number of nucleotides forming the loop followed by a reverse complement of the first half of the stem. The first half and second half of the stem will generally be the exact same length though in some embodiments, one half can have one nucleotide more than the other stem half such that when the two halves anneal, one nucleotide of one half does not anneal. Each half of the stem can be any size as desired, for example, between 5-15 nucleotides long, e.g., 5, 6, 7, 8, 9, 10, 11, 12, 13, 14, or 15 nucleotides. The loop will have at least one nucleotide, and in some embodiments, between 2-6, e.g., 2, 3, 4, 5, or 6 nucleotides. In some embodiments, the stem will have a melting temperature (Tm) of at least 40, 45, 50, 55, 60, or 65° C. In some embodiments, for example, the Tm is at least 5 or 10 degrees higher than the temperature of the primer extension assay employed. The Tm of the loop can be determined empirically, and in some embodiments can be estimated, e.g., using formulas as described in F. Baldino, Jr, M.-F. Chesselet, and M. E. Lewis, Methods in Enzymology 168:766 (1989). In some embodiments, the stem has a minimum free energy (delta-G) of −8.5, −3, or less at 37° C. Ideally, the polynucleotide 3' end sequence will allow for few or no alternative conformations (e.g., other alternative secondary structures). These aspects can be analyzed by software available to those of ordinary skill in the art. Examples of such software include the UNAFold software available at mfold.rna.albany.edu. Alternatively, more complicated (e.g., hammerhead) secondary structures can be formed so long as the structure impairs availability of the 3' end to reduce spurious priming. In some embodiments, the final 3' end of the polynucleotide coincides with the 3' terminus of the stem (i.e., the last nucleotide in the stem structure). Alternative, in some embodiments, at the 3' end, 1, 2, 3, 4, 5 or 6 nucleotides can be present at the 5' end that is/are not part of the stem loop due to lack of complementarity to nearby nucleotides in the 5' direction of the stem.

Exemplary Workflow

The following is provided as an example and is not necessarily intended to limit the claimed invention.

Referring to FIG. 1, target primers and other PCR reagents including a polymerase are provided in partitions (FIG. 1, A). Genomic DNA (FIG. 1, B) from a sample is injected into the partitions and submitted to thermocyclic conditions by being driven by pressure through a serpentine microfluidic channel (FIG. 1, C), thereby generating an amplicon, which is the target nucleic acid. The amplification reaction also introduces a fluorescent molecule to the 5' end of the target nucleic acid.

Simultaneously, a provided primer partition library is provided in a vessel. The primer partitions comprise multiple primers (a set), wherein different partitions comprise different primer sets. As an example, a library of contiguous (or gapped) hexamers of every sequence possible (4096) are provided in sets of ten primers, where each set includes one primer that also occurs in at least one other set. The primer partitions further comprise one or more different dyes at one of several possible concentrations, such that the concentration of the different dyes indicates the identity of the primer set in a particular primer partition. A strand displacement polymerase is added to the primer partitions before or after they are merged with the target nucleic acid partitions. Portions of the target nucleic acid partitions are injected into the primer partitions (such that one target nucleic acid is injected into many primer partitions) to form reaction partitions (FIG. 1, D).

The reaction partition, comprising a displacing polymerase and a hybridizing quencher polynucleotide, proceed through the microfluidic channel under conditions to allow for displacement of the quencher polynucleotide if at least one of the primers from the primer partition hybridize to the target nucleic acid.

Signal from the reaction partitions can be generated continuously. The signal is detected by one or more detector (FIG. 1, F). Signal detected includes the presence or absence (or differential level) of fluorescence from the fluorescent molecule on the target nucleic acid, thereby determining hybridization. Also detected is the level and identity of the various dyes in the partition, thereby providing the identity of the particular primers in the partition. Several embodiments of the present invention make use of the software architecture depicted in FIG. 6A. FIG. 2 is laid out to show which software modules are executed at which stage of the process and acting at which temporal granularity and operating on which inputs. For example, the signal processing module is executed once for every primer partition measured by the optical detector.

The resulting signals are subsequently processed. For instance, the level of identity of the various dyes (e.g., each detected at a different wavelength) is used to determine the identity of the primer set, and thus the sequence of every primer in the reaction partition. The data can thus be sorted into primer sets that do not hybridize and those that do hybridize. The presence or absence of hybridization of a particular primer can be logically determined (e.g., via computer software) from the pattern of hybridization of the sets. For example, a positively-hybridizing partition initially indicates that potentially all primers in the partition hybridize. By review of negatively hybridizing partitions however, one can determine that overlapping primers between negatively and positively-hybridizing partitions in fact do not hybridize. The resulting information of primer hybridization can then be used (again via computer software), in combination with knowledge of the general structure of the target nucleic acid to generate a predicted target sequence based on the presence or absence of hybridization of the primers.

Further, the signal from the reactions can be monitored continuously to determine the edges of signal originating from different target nucleic acid partitions, i.e., when portions from a first target nucleic acid partition are exhausted and partitions from a second target nucleic acid partition (mixed with primer partitions) are being detected. This method is particularly useful in the situation where multiple target nucleic acids are being assayed in the system (e.g., in embodiments in which different primer pairs are used to generate different target nucleic acid partitions, or in the case of allelic variance or sample variation) at least in part because one can subsequently predict and sort the signal from the partitions based on the predicted identity of the target nucleic acid in the partitions. As an example, if two targets may be present in the system, and the wildtype sequence of each target is known, then one can predict which prime partitions will hybridize and which will not to a wildtype reference sequence. This pattern of primer partition hybridization can then be compared to the actual pattern of primer partition hybridization to determine which target is being assayed in a particular target nucleic acid partition ("slug"). This information can be helpful later when assembling sequences as one will know which hybridization signals applied to target 1 compared to target 2, for example, prior to assembly of the target sequence.

FIG. 16 illustrates an exemplary assembly process by which a target nucleic acid sequence is determined based on the presence or absence of hybridization of primers in the series. As an initial stage, hybridizing primers are arrayed in an unambiguous overlapping pattern to generate an initial target scaffold sequence. In many embodiments, the scaffold will be incomplete with gaps in the sequence that cannot be determined solely by positive hybridization. For example, in some cases a hybridizing primer could logically be placed in an array in the scaffold in two or more positions. In this case, primers of similar but different sequence that negatively (do not) hybridize can be applied to resolve ambiguous positions. This aspect is also illustrated in FIG. 17 where the circled positively hybridizing primers could logically occur at either position in the scaffold. Negative primers 1722 and 1724 can then be used to resolve that the circled primers belong at position C. In some embodiments, in view of resolving certain positive primers with the negative primer data, additional previously ambiguous positive primer sequences can then be placed in the scaffold. Optionally, a reference sequence (i.e., the general structure of a target sequence) can be compared to the scaffold to resolve ambiguities. As an example, if a portion of p53 was the target sequence, the database reference p53 sequence could be used as a reference to the scaffold for comparison.

Partitions

Partitions can include any of a number of types of partitions, including solid partitions (e.g., wells or tubes) and fluid partitions (e.g., aqueous droplets within an oil phase). In some embodiments, the partitions are droplets. In some embodiments, the partitions are microchannels. Methods and compositions for partitioning a sample are described, for example, in published patent applications WO 2010/036352, US 2010/0173394, US 2011/0092373, US 2011/0092376, US2012/0222748; WO2013/09573; and US 2011/0218123 the entire content of each of which is incorporated by reference herein.

In some embodiments, the sample is partitioned into a plurality of droplets. In some embodiments, a droplet comprises an emulsion composition, i.e., a mixture of immiscible fluids (e.g., water and oil). In some embodiments, a droplet is an aqueous droplet that is surrounded by an immiscible carrier fluid (e.g., oil). In some embodiments, a droplet is an oil droplet that is surrounded by an immiscible carrier fluid (e.g., an aqueous solution). In some embodiments, the droplets described herein are relatively stable and have minimal coalescence between two or more droplets. In some embodiments, less than 0.0001%, 0.0005%, 0.001%, 0.005%, 0.01%, 0.05%, 0.1%, 0.5%, 1%, 2%, 3%, 4%, 5%, 6%, 7%, 8%, 9%, or 10% of droplets generated from a sample coalesce with other droplets. The emulsions can also have limited flocculation, a process by which the dispersed phase comes out of suspension in flakes.

In some embodiments, the droplet is formed by flowing an oil phase through an aqueous solution comprising the label(s) to be detected. In some embodiments, the aqueous sample comprising the label(s) to be detected comprises a buffered solution and reagents for detecting the label(s). The oil for the oil phase may be synthetic or naturally occurring. In some embodiments, the oil comprises carbon and/or silicon. In some embodiments, the oil comprises hydrogen and/or fluorine. Exemplary oils include, but are not limited to, silicone oil, mineral oil, fluorocarbon oil, vegetable oil, or a combination thereof.

The oil phase may comprise a fluorinated base oil which may additionally be stabilized by combination with a fluorinated surfactant such as a perfluorinated polyether. In some embodiments, the base oil comprises one or more of a HFE 7500, FC-40, FC-43, FC-70, or another common fluorinated oil. In some embodiments, the oil phase comprises an anionic fluorosurfactant. In some embodiments, the anionic fluorosurfactant is Ammonium Krytox (Krytox-AS), the ammonium salt of Krytox FSH, or a morpholino derivative of Krytox FSH. Krytox-AS may be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of Krytox-AS is about 1.8%. In some embodiments, the concentration of Krytox-AS is about 1.62%. Morpholino derivative of Krytox FSH may be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of morpholino derivative of Krytox FSH is about 1.8%. In some embodiments, the concentration of morpholino derivative of Krytox FSH is about 1.62%.

In some embodiments, the oil phase further comprises an additive for tuning the oil properties, such as vapor pressure, viscosity, or surface tension. Non-limiting examples include perfluorooctanol and 1H,1H,2H,2H-Perfluorodecanol. In some embodiments, 1H,1H,2H,2H-Perfluorodecanol is added to a concentration of about 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.25%, 1.50%, 1.75%, 2.0%, 2.25%, 2.5%, 2.75%, or 3.0% (w/w). In some embodiments, 1H,1H, 2H,2H-Perfluorodecanol is added to a concentration of about 0.18% (w/w).

In some embodiments, the emulsion is formulated to produce highly monodisperse droplets having a liquid-like interfacial film that can be converted by heating into microcapsules having a solid-like interfacial film; such microcapsules may behave as bioreactors able to retain their contents through an incubation period. The conversion to microcapsule form may occur upon heating. For example, such conversion may occur at a temperature of greater than about 40°, 50°, 60°, 70°, 80°, 90°, or 95° C. During the heating process, a fluid or mineral oil overlay may be used to prevent evaporation. Excess continuous phase oil may or may not be removed prior to heating. The biocompatible capsules may be resistant to coalescence and/or flocculation across a wide range of thermal and mechanical processing.

Following conversion, the microcapsules may be stored at about −70°, −20°, 0°, 3°, 4°, 5°, 6°, 7°, 8°, 9°, 10°, 15°, 20°, 25°, 30°, 35°, or −40° C. In some embodiments, these capsules are useful in biomedical applications, such as stable, digitized encapsulation of macromolecules, particularly aqueous biological fluids comprising a mix of target molecules such as nucleic acids, proteins, or both together; drug and vaccine delivery; biomolecular libraries; clinical imaging applications; and others.

The microcapsule partitions may contain one or more affinity agents as described herein and may resist coalescence, particularly at high temperatures. Accordingly, the capsules can be incubated at a very high density (e.g., number of partitions per unit volume). In some embodiments, greater than 100,000, 500,000, 1,000,000, 1,500,000, 2,000,000, 2,500,000, 5,000,000, or 10,000,000 partitions may be incubated per mL. In some embodiments, the sample-probe incubations occur in a single well, e.g., a well of a microtiter plate, without inter-mixing between partitions. The microcapsules may also contain other components necessary for the incubation.

In some embodiments, the droplets that are generated are substantially uniform in shape and/or size. For example, in some embodiments, the droplets are substantially uniform in average diameter. In some embodiments, the droplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets that are generated are non-uniform in shape and/or size.

In some embodiments, the droplets that are generated are substantially uniform in volume. For example, in some embodiments, the droplets that are generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

Libraries

Also provided are libraries of primer partitions as described herein. For example, in some embodiments, a library of partitions are provided, wherein the partitions comprise multiple different primers and at least 1000; 10,000; 100,000; or more different unique primer sets are provided in the partitions, with one primer set per partition. In some embodiments, the sets will contain 2-20 (e.g., 5-15, 5-10, 7-12) different primers. In some embodiments, the primers will include at least 4, 5, 6,7, 8, 9, 10, or more designated nucleotides as well as optionally 1, 2, 3, 4, 5, or more "gap" degenerate positions.

In some embodiments, the library of partitions will further comprise one or more spectroscopically distinguishable molecule for determining the identity of the primes in the partition. Thus for example, if there are n different sets of primers represented in the partitions, there will be n different spectroscopically distinguishable characteristics, with each different set assigned to a particular characteristic. As noted above, this can be achieved, for example, by providing 1, 2, 3, 4, 5 or more different detectable dyes, each at one or 2, 3, 4, 5, 6, 7, 8, 9, 10, or more concentrations, such that combination of the concentrations of the dyes provides a unique spectroscopically distinguishable characteristics for each primer set. Methods and systems for monitoring combinations of spectroscopic intensity are described in, e.g., WO 2012/135327.

Systems

Also provided are systems for performing the methods described herein. In some embodiments, the systems include a first vessel comprising a series of primers in a plurality of primer partitions (e.g., drops) as described herein. In some embodiments, the system further comprises a first microfluidic channel providing fluid communication between the first vessel and a detector and the detector. In some cases, the system also includes a second vessel comprising primer pairs for amplifying the target nucleic acid; a second microfluidic channel providing fluid communication between the second vessel and the first microfluidic channel; and a sample nucleic acid vessel in fluid communication with the second microfluidic channel. See, e.g., FIG. 1. In some embodiments, the first channel comprises a serpentine portion configured to such that different portions of the serpentine channel can be set at different temperatures (e.g., with Peltier elements or other temperature control elements and optionally a thermostat). In some embodiments, all of the above described components are provided as part of a single cartridge. In some embodiments, the cartridge can in turn be inserted into a manifold allowing for attachment to one or more pumps configured to pump drops through the microfluidic channels.

In some embodiments, the system further comprises a one or more droplet injector. In some embodiments, the system comprises a first droplet injector configured to inject nucleic acids from the sample nucleic acid vessel into drops comprising primer pairs from the second vessel and located in the second microfluidic channel to form mixture drops and a second droplet injector configured to inject portions of the mixture drops into primer drops that travel down the first microfluidic channel. Droplet injectors are described in, e.g., US 2012/0132288.

Exemplary system components are described in, e.g., US2011/0267457, US2011/0151578, US2011/0218123, US2012/0222748, US2011/0218123, 2012/0222748, WO2012/135201, WO2012/135259, WO2014/043388, WO 2012/135327.

Detectors as described herein can detect one or both of signal from (i) the hybridization assay or (ii) the dyes in the primer partitions for identifying the primers. In some embodiments, the droplets in an emulsion flow through microfluidic channels passed an optical detector that measures a fluorescent signal coming from the assay. In some embodiments, multiple sets of measurements of the same target molecule signal over time are generated and aggregated The spectroscopic intensity and wavelength of a spectroscopic substance may be measured by any methods for spectroscopic analysis known and appreciated by one or ordinary skill in the art. Spectroscopic methods that may be utilized in the present invention include, but are not limited to, a laser and photodetector pair system or more complex optics known to those of skill in the art where the path of an optical beam intersects with the path of a spectroscopic substance and the excitation or illumination of the spectroscopic substance is captured by an optical path comprising one or more objective, mirror, and/or lens to direct the light to a photomultiplier tube (PMT) or photosensitive camera. A known fluoroscopy method that will be known and appreciated by one of skill in the art for use in the present invention is the use of flow cytometry instrumentation.

The spectroscopic intensity measurements may comprise one or more methods, including but not limited to, light scatter, absorption, chemiluminescence, fluorescent intensity, radiation decay counts, colorimetric, and so forth.

Samples to be tested are placed in the path of an excitation energy source such as a light source selected from but is not limited to, lasers, light-emitting diodes (LEDs), arc lamps, broadband light source, and high intensity light bulbs. The spectroscopic substances in the sample to be tested scatter, absorb, chemiluminesce, or fluoresce (also referred to herein as "signal") in the form of light at a wavelength substantially different from the wavelength of the light source. This light from the sample to be tested is then captured by a detector or sensor, which may be selected from but is not limited to, a camera, a charge coupled device (CCD), a complementary metal-oxide-semiconductor (CMOS) (alternatively referred to as a complementary-symmetry metal-oxide-semiconductor (COS-MOS)), one or more individual photodiodes, photodiode arrays (PDAs), avalanche photodiodes (APDs), avalanche photodiodes arrays, photomultiplier tubes (PMTs), or photomultiplier tube arrays.

Known optical or electronic means may be optionally used to amplify the light from the light source and/or the light from the sample to be tested and/or to separate one or both into its component wavelengths. Selecting a reference spectroscopic substance and one or more sample spectroscopic substances for a particular sample to be tested such that each spectroscopic substance scatters light, selectively absorbs light, emits light in the form of chemiluminescence or fluorescence, depending upon the spectroscopic substance and particular application, at substantially different wavelengths allowing for easier separation of the respective wavelengths. The difference between the reference spectroscopic substance's expected value and measured value can be used to quantify the contribution of "noise" to the output, assuming the reference spectroscopic substance and the one or more sample spectroscopic substances are subject to the same measurement conditions (e.g., the power of the light source, detector or sensor noise, humidity, heat, pH of the sample to be tested, and the vehicle that the sample to be tested itself is in). The contribution of "noise" to the reference spectroscopic substance signal should correlate with the contribution of noise to the signal of the one or more sample spectroscopic substances. This correlation may be, and is typically, proportional but could vary linearly, exponentially, or in other manners or functions as well.

In some, but not all embodiments, all components of the systems and methods described herein are microfluidic. "Microfluidic," as used herein, refers to a device, apparatus or system including at least one fluid channel having a cross-sectional dimension of less than 1 mm, and a ratio of length to largest cross-sectional dimension perpendicular to the channel of at least about 3:1. A "microfluidic channel," as used herein, is a channel meeting these criteria.

Microfluidic systems may be provided that are able to cause two or more droplets to fuse or coalesce into one droplet, for example, in cases where the two or more droplets ordinarily are unable to fuse or coalesce, for example due to composition, surface tension, droplet size, etc. as known to those of ordinary skill in the art. Examples of embodiments in which two or more droplets are fused have been described above. The fluidic droplets may be fused together using any suitable technique, for example, as discussed in U.S. patent application Ser. No. 11/246,911, filed Oct. 7, 2005, entitled "Formation and Control of Fluidic Species," by Link, et al., published as U.S. Patent Application Publication No. 2006/0163385 on Jul. 27, 2006; or U.S. patent application Ser. No. 11/360,845, filed Feb. 23, 2006, entitled "Electronic Control of Fluidic Species," by Link, et al., published as U.S. Patent Application Publication No. 2007/0003442 on Jan. 4, 2007, each incorporated herein by reference. As an example, in microfluidic systems, the surface tension of the droplets, relative to the size of the droplets may prevent fusion or coalescence of the droplets from occurring. In one embodiment, two droplets may be given opposite electrical charges (i.e., positive and negative charges, not necessarily of the same magnitude), which may increase the electrical interaction of the two droplets such that fusion or coalescence of the droplets can occur. Electrical charges (positive or negative) may be imparted onto droplets through the use of Taylor cones, or through any other suitable techniques. For instance, an electric field may be imposed on a reactor containing the droplets, the droplets may be passed through a capacitor, a chemical reaction may occur to cause the droplets to become charged, flowing the droplets over a region with opposite wetting properties, etc.

The "cross-sectional dimension" of the channel is measured perpendicular to the direction of fluid flow. Most fluid channels in components of the invention have maximum cross-sectional dimensions less than about 2 mm, and in some cases, less than about 1 mm. In one set of embodiments, all fluid channels containing embodiments of the invention are microfluidic or have a largest cross sectional dimension of no more than about 2 mm or about 1 mm. In another embodiment, the fluid channels may be formed in part by a single component (e.g. an etched substrate or molded unit). Of course, larger channels, tubes, chambers, reservoirs, etc. can be used to store fluids in bulk and to deliver fluids to components of the invention. In one set of embodiments, the maximum cross-sectional dimension of the channels) containing embodiments of the invention are less than about 500 microns, less than about 200 microns, less than about 100 microns, less than about 50 microns, or less than about 25 microns.

A "channel," as used herein, means a feature on or in an article (substrate) that at least partially directs the flow of a fluid. The channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and outlet(s). A channel may also have an aspect ratio (length to average cross sectional dimension) of at least about 2:1, more typically at least about 3:1, at least about 5:1, or at least about 10:1 or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

The channel may be of any size, for example, having a largest dimension perpendicular to fluid flow of less than about 5 mm or about 2 mm, or less than about 1 mm, or less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm. In some cases the dimensions of the channel may be chosen such that fluid is able to freely flow through the article or substrate.

The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, positioned to intersect with each other, etc.

Non-limiting examples of microfluidic systems that may be used with the present invention are disclosed in U.S. patent application Ser. No. 11/246,911, filed Oct. 7, 2005, entitled "Formation and Control of Fluidic Species," published as U.S. Patent Application Publication No. 2006/0163385 on Jul. 27, 2006; U.S. patent application Ser. No. 11/024,228, filed Dec. 28, 2004, entitled "Method and Apparatus for Fluid Dispersion," published as U.S. Patent Application Publication No. 2005/0172476 on Aug. 11, 2005; U.S. patent application Ser. No. 11/360,845, filed Feb. 23, 2006, entitled "Electronic Control of Fluidic Species," published as U.S. Patent Application Publication No. 2007/000342 on Jan. 4, 2007; International Patent Application No. PCT/US2006/007772, filed Mar. 3, 2006, entitled "Method and Apparatus for Forming Multiple Emulsions," published as WO 2006/096571 on Sep. 14, 2006; U.S. patent application Ser. No. 11/368,263, filed Mar. 3, 2006, entitled "Systems and Methods of Forming Particles," published as U.S. Patent Application Publication No. 2007/0054119 on Mar. 8, 2007; U.S. Provisional Patent Application Ser. No. 60/920,574, filed Mar. 28, 2007, entitled "Multiple Emulsions and Techniques for Formation"; and International Patent Application No. PCT/US2006/001938, filed Jan. 20, 2006, entitled "Systems and Methods for Forming Fluidic proplets Encapsulated in Particles Such as Colloidal Particles," published as WO 2006/078841 on Jul. 27, 2006, each incorporated herein by reference in their entireties.

Software

As discussed above, the methods described herein generate data relating to positively-hybridizing primers as well as negatively-hybridizing primers. Accordingly, in some embodiments, methods of resolving a target nucleic acid sequence are provided that use both the positive and negative data. In some embodiments, hybridizing primers are arrayed in an unambiguous overlapping pattern to generate an initial target scaffold sequence. In this step, only unambiguous alignments are employed. In many embodiments, the scaffold will be incomplete with gaps in the sequence that cannot be determined solely by positive hybridization. For example, in some cases one or more hybridizing primer could logically be placed in an array in the scaffold in two or more positions. In this case, primers of similar but different sequence that negatively (do not) hybridize are applied to resolve ambiguous positions based solely on positive hybridization. In some embodiments, in view of resolving certain positive primers with the negative primer data, additional previously ambiguous positive primer sequences can then be placed in the scaffold. Optionally, a reference sequence (i.e., the general structure of a target sequence) can be compared to the scaffold to resolve ambiguities.

In embodiments in which portions of a target nucleic acid partition (also referred to herein as a "slug" or a "mixture drop") are combined with different primer portions to form reaction partitions, it is desirable to determine which reaction signals were derived from which target nucleic acid partitions. For example, in a simple example, portions of a first target nucleic acid partition are combined with primer partitions to generate first target nucleic acid reaction partitions, which generate signal. As soon as the first target nucleic acid partition is depleted, the system generates portions from a second target nucleic acid partition and combines those portions with other primer partitions on a one-for-one basis. It can therefore be desirable to determine from the signal generated where data derived from one mixture drop (e.g., from the first target nucleic acid partition) ends and another mixture drop (e.g., from the second target nucleic acid partition) begins, especially in the case in which different target nucleic acid partitions may contain different alleles, amplicons, etc.

FIG. 18 is a flowchart illustrating a method 1800 for determining a nucleotide sequence of the target nucleic acid according to embodiments of the present invention. Method 1800 can be performed wholly or partially by a computer system.

At block 1850, a data signal is received. The data signal corresponds to an experiment involving hybridization of a plurality of primers to a target nucleic acid, e.g., as described above. The data signal can be obtained by the detector over a time period. The data signal can be composed of respective signals, each for a respective reaction partition generated from the merger of a portion of a mixture drop with a primer partition. Multiple mixture drops can be used, and each mixture drop can include copies of one or more target nucleic acids. Each reaction partition includes one or more primers, and all the partitions can include a plurality of primers.

At block 1820, it is determined which partitions correspond to which mixture drops. The data signal can be a continuous stream of data collected by a detector. As each new partition passes by the detector, additional data is received. Given that each mixture drop is partitioned into a plurality of reaction partitions and that there is a continuous stream of partitions passing by the detector, it is not readily known for the partitions where one mixture drop ends and where the partitions for the next mixture drop begin. The partitions corresponding to a same mixture drop are herein called a cohort.

In one embodiment, the beginning of a cohort (end of the previous cohort) can be determined by analyzing the hybridization data of the partitions. If a cohort of partitions correspond to a same mixture drop, the hybridization of those partitions should be similar. For example, a same primer should hybridize to the target nucleic acid regardless of which partition of the cohort that primer is in. Contradictions in the hybridization data can be tracked, and minimums in the amount of contradictory data at a particular point in time can indicate an end of one cohort and the beginning of the next cohort.

At block 1830, a corresponding target nucleic acid is determined for each cohort of partitions. Because there can be many target nucleic acids in total over the plurality of mixture drops, it is not readily known which target nucleic acid is contained within a mixture drop. Additionally, this is complicated by the fact that mixture drops can include more than one target nucleic acid.

In one embodiment, a hybridization profile (e.g., a bit vector) can be created for a particular cohort of partitions. The hybridization profile can be compared to reference hybridization profiles, each of which corresponds to a different reference (e.g., wildtype) target nucleic acid. And, a closest reference hybridization profile can be identified. A cohort can be identified as corresponding to the target nucleic acid with the closest hybridization profile. Multiple cohorts can correspond to a same target nucleic acid. And, one cohort can correspond to multiple target nucleic acids (e.g., where mixture drop includes a plurality of target nucleic acids).

At block 1840, hybridization states of the primers are determined for target nucleic acid. A hybridization state of a primer specifies whether the primer has hybridized to the particular target nucleic acid. A hybridization status of a partition specifies that at least one primer in the petition has hybridized to the particular target nucleic acid. The hybridization status of a partition can be determined based on the signal from the petition. For example, the signal can be a binary value depending on whether a particular color is emitted from the partition and detected by the detector.

Since a partition can include a plurality of primers, the hybridization state of a primer in a partition is not readily known from the hybridization status of the partition. However, a same primer is included in multiple partitions. And, when the number of partitions is large, the specific primers within any one partition will vary. In one embodiment, the hybridization status of partitions having a same primer can be compared to identify contradictory status. Such an analysis can indicate a hybridization state of that same primer.

At block 650, primers that hybridize to the target nucleic acid are used to assemble the nucleotide sequence of the target nucleic acid. For example, the sequences of these primers can be assembled by determining or overlapping nucleotides that are consistent with each other. Knowledge of primers that do not hybridize to the target nucleic acid can also be used. For example, multiple options might be available where a primer might aligned to the target nucleic acid, and a negative primer (i.e., one that does not hybridize) can help to rule out one of the options.

A. Determining Cohorts

The determination of a cohort can be considered a temporal segmentation of primer partition readout. Information that a primer does not hybridize can be used in various ways. Since primers within a partition have no means by which to cancel one another's positivity, one can look to other partitions that were measured at different times during the run. This involves associating partitions to each other. In some embodiments, one association is between partitions from a same mixture drop, i.e., intra cohort. Since the partitions within a cohort likely include a same target nucleic acid, primers that are shared among partitions from the same mixture drop should reflect the same hybridization to the target nucleic acid of the mixture drop.

FIG. 9 shows a plot 900 showing edges of cohorts partitions according to embodiments of the present invention. The horizontal axis corresponds to partition number, which corresponds to a particular time. The vertical axis corresponds to a contradiction value.

A contradiction rate 910 is shown between partition zero and partition 50,000. The contradiction rate is calculated using a sliding window over the partitions. In various embodiments, the center or start of each sliding window can provide the data point at that partition. For example, the contradiction value at 10,000 can be determined from the next 2,000 partitions after (possibly including) partition 10,000.

When all partitions correspond to a same mixture drop, the amount of contradictions should be in a minimum, given that the hybridization status is measuring hybridization to the same target nucleic acid. Whereas, when the partitions are from different mixture drops, the different partitions have hybridization status is that are measured against different target nucleic acids; and thus the contradiction rate is at maximum. In FIG. 9, edges 920 between mixture drops (slugs) are shown at the minima of contradiction rate 910 between the peaks. In other embodiments, the edges can be identified at maximum, depending on how the sliding window is defined, e.g., where sliding window the centered at a particular time.

Contradiction rate 910 can be determined as a ratio or a raw number. For the ratio, the numerator can correspond to an amount of partitions that show contradictory hybridization status. The amount can be counted as a number of partitions or a number of primers that show contradictory data. For example, two partitions can have a same primer but have different hybridization status, this can be seen as contradictory data. In various embodiments, the number of partitions that are contradicted can be counted, or the number of primers that are contradicted can be counted.

FIG. 19 is a flowchart of a method 1900 of identifying primer/target nucleic acid partitions as being generated from a same target nucleic acid partition mixture drop.

At block 1910, a data signal obtained by a detector over a time period is received. The data signal can include signals from a plurality of reaction partitions generated from a plurality of mixture drops. Each mixture drop can correspond to a cohort of partitions and include copies of at least one target nucleic acid. Each partition can include one or more primers. The data signal includes data about whether at least one primer in a partition hybridizes to a target nucleic acid.

At block 1920, a hybridization status of each partition is identified based on the respective signal of the respective partition. The hybridization status of a partition can indicate whether a primer in the partition hybridized to a target nucleic acid. A signal of a particular partition corresponds to a particular time.

At block 1930, an amount of partitions that have contradictory hybridization statuses and include a same primer is calculated, thereby obtaining a temporal function. An amount is determined for each of a plurality of particular times in the time period. The amount at a particular time is determined from partitions within a time window corresponding to the particular time.

In one embodiment, the amount of partitions that have contradictory hybridization statuses corresponds to an amount of primers that are in partitions with contradictory hybridization statuses. For example, the amount can be a count of primers that are in one partition with a positive hybridization status and that are in one partition with a negative hybridization status. In another embodiment, the amount can be a count of partitions having a same primer but contradictory hybridization status.

The amount of partitions can normalized by a number of distinct partitions in the time window. Two partitions can be distinct when the two partitions include at least one different primer.

In one implementation, the time window can be specified as a number of partitions. The time window is can start at or be centered around a partition at the particular time. The number of partitions in the time window can be selected based on the number of partitions created from a mixture drop.

At block 1940, extrema are identified in the temporal function. The extrema can be maxima or minima. The extrema are local extrema. Any suitable technique for determining extreme can be used. For example, a lowest value between two peaks can be used as a minimum.

At block 1950, a cohort of successive partitions occurring between corresponding extrema in the temporal function is determined as corresponding to a same mixture drop. The cohort can be analyzed together. In some embodiments, when a first cohort of successive partitions correspond to a first mixture drop that includes a first target nucleic acid, it can be determined whether each primer in the first cohort hybridizes to the first target nucleic acid based on the signals for the first cohort. Further details for this determination are provided below. Then, the primers in the first cohort and a hybridization state of the primers in the first cohort can be used to determine a nucleotide sequence of the first target nucleic acid.

B. Determining Target for a Cohort

FIG. 10 is a diagram showing the determination of a hybridization profile for a mixture drop according to embodiments of the present invention. FIG. 10 shows the sequence of a target nucleic acid 1000. The exact sequence for a sample being tested may not be known, but a reference sequence for the same region can be obtained. The sequence of target nucleic acid 1000 is shown for illustrative purposes.

A bit vector 1010 is generated as a hybridization profile. A bit vector is defined as any way to specify a hybridization status of each partition in the cohort corresponding to the mixture drop. As a hybridization status is true or false, the values can be specified by bits. The bit values can be zero or one, or any combination of two numbers. Only a portion of bit vector 1010 is shown, namely the values for the first 10 partitions of the cohort. In this example, partition zero has a positive hybridization status and partition nine as a positive hybridization status.

The hybridization statuses are further illustrated by illustrating primers in various partitions. The cohort of primers 1020 include CGTAGG, which is present in the sequence of target nucleic acid 900, and thus the hybridization status as positive. The cohort of primers 1030 are not present in the sequence of the target nucleic acid 1000. The cohort of primers 1040 include GATGCT, which is present in the sequence of target nucleic acid 1000.

FIG. 11 is a diagram showing the comparison of a hybridization profile of a mixture drop compared to a reference hybridization profiles associated with reference nucleic acids according to embodiments of the present invention. Row 1110 shows the hybridization status measured for each partition of a cohort. Each symbol corresponds to a different partition. Row 1140 provides the partition number. Row 1120 shows a hybridization status of a particular partition represented as a binary value. Some partitions do not show up in this cohort, and thus do not have corresponding measurements.

Array 1130 corresponds to hybridization profiles of known reference sequences. Each row in array 1130 corresponds to a different reference sequence, and thus is a different hybridization profile. As the primers of each partition are known, the expected bit value for a partition can be determined. The bit vectors for the reference sequences can be determined for all possible partitions, and thus bit values are not missing from these hybridization profiles.

Column 1132 corresponds to a difference between bit vector 1120 and the reference bit vectors. For example, bit vector 1120 differs from the first reference bit vector at three partitions (0, 7, and 8). Thus, the difference is three. Other distances between the vectors can be used. Reference bit vector 1134 is the most similar to bit vector 1120; and in fact, the two are the same for the partitions included in the cohort.

Various criteria can be used to select one or more of the reference how position profiles. For example, a minimum similarity can be required. The minimum similarity can be a raw value, e.g., less than one or two differences. Another criteria can be that the lowest difference value is sufficiently different than the next lowest difference value, e.g., the two values must be separated at least by N, where N is a pretty predetermined value.

FIG. 12 is a diagram showing the comparison of hybridization profiles of mixture drops to each other according to embodiments of the present invention. A cohort 2150 of hybridization profiles of various mixture drops are shown. Two of the specific hybridization profiles of the cohort 1250 are shown. Rows 1210 and 1240 shows a hybridization status of partitions. Rows 1220 and 1230 show the corresponding bit values. The bit vectors for the mixture drops can be compared to each other for partitions 1260 that are common among the hybridization profiles.

The differences between the hybridization profiles can be used to cluster the hybridization profiles. The hybridization profiles of a given cluster can be taken as corresponding to a same target nucleic acid. In this example, the reference hybridization profiles (bit vectors) correspond to the hybridization profiles of other mixture drops.

FIG. 20 is a flowchart of a method of identifying a mixture drop as including a target nucleic. Method 2000 can use features from other methods described herein. Method 2000 can be performed wholly or partly by a computer system.

At block 2010, a hybridization status of each of a plurality of partitions is received. Each partition includes one or more primers, and each can include a plurality of primers. Each of a plurality of mixture drops may be partitioned and each include copies of one or more target nucleic acids. The hybridization status of a partition can indicate whether at least one primer in the partition hybridized to a target nucleic acid.

At block 2020, a first cohort of partitions can be identifying as corresponding to a first mixture drop. Method 1900 may be used to determine the first cohort.

At block 2030, a first bit vector can be created for the first cohort of partitions. Each value in the bit vector can corresponds to a hybridization status of a respective partition of the first cohort. The hybridization status can be a binary value or have more values.

At block 2040, the first bit vector can be compared to a plurality of reference bit vectors to obtain a difference value relative to each of the plurality of reference bit vectors. Each reference bit vector can correspond to a different reference nucleic acid and include values of hybridization status of each partition in the first cohort relative to the reference nucleic acid.

In one embodiment, a counter is incremented for each partition of the first cohort that has a different hybridization status from the first reference bit vector. This counter can determine a distance (e.g., Hamming distance) between two bit vectors.

In one implementation, each of the reference nucleic acids has a known sequence. For example, the reference sequences can correspond to a reference genome. A reference bit vector can be created by determining an expected hybridization status for each partition in the first cohort. The expected hybridization status for a partition can be determined based on the primers in the partition. For example, the primers in the first cohort are known, and the primers can be compared to the reference sequence to determine whether one of them hybridizes.

In another embodiment, the reference sequences correspond to other cohorts associated with the same target nucleic acid. Thus, the reference nucleic acids can correspond to nucleic acids in other mixture drops. The bit vectors can be clusters. For example, bit vectors of a plurality of mixture drops can be clustered. A first cluster of mixture drops that include the first target nucleic acid can be identified based on a similarity of the bit vectors of the first cluster.

At block 2050, a first target nucleic acid in the first mixture drop is identified based on the difference values. In one embodiment, the reference nucleic acid with a lowest counter is selected as the first target nucleic acid. In another embodiment, the reference nucleic acid with a lowest counter can be selected as the first target nucleic acid when the lowest counter is at least a predetermined amount less than a next highest counter. For example, the lowest value must be at least N lower than the next lowest. Examples of N are between 2-10 or between 10-50.

Once the first target nucleic acid is identified, embodiments can use the primers in the first cohort of partitions to determine a nucleotide sequence of the first target nucleic acid. For example, each partition can include a plurality of primers. Then, primers in the first cohort of partitions that positively hybridize to the first target nucleic acid can be identified. The identified primers can be assembled to determine the nucleotide sequence of the first target nucleic acid.

C. Hybridization State of a Primer

FIG. 13 illustrates the determination of the hybridization state of a primer by comparing a hybridization status of partitions of the same cohort according to embodiments of the present invention. Partitions 1300 and partitions 1310 are part of the same cohort. Partitions 1300 have a positive hybridization status, and have four primers each. Partitions 1310 have a negative hybridization status, and have four primers each.

Taking partitions 1300 by themselves, it is not known which of the four primers in each partition actually hybridize to a target nucleic acid. But, one can cross-reference the negative status of the primers in partitions 1310 to eliminate primers of partitions 1300 as being positively hybridizing. For example, primer 1315 can be identified as having a negative hybridization state (i.e., not hybridizing to the target nucleic acid) since primer 1315 is within a partition having a negative hybridization status. Primer 1315 is also within one of partitions 1300, but can be eliminated since primer 1315 has a negative hybridization state. Primers having a negative hybridization state are shown crossed off in partitions 1300, thereby allowing identification of primers 1303 and 1306 as having a positive organization state.

FIG. 14 illustrates the determination of the hybridization state of a primer by comparing a hybridization status of partitions of different cohorts according to embodiments of the present invention. FIG. 14 shows a sequence of a target nucleic acid 1400. Partitions 1420 are from a first cohort associated with target nucleic acid 1400, and partitions 1440 are from a second cohort also associated with target nucleic acid 1400.

In this example, certain primers in the partitions that have a positive hybridization status can be eliminated based on the primers in partitions that have a negative hybridization status. As the two cohorts correspond to a same target nucleic acid 1400 the hybridization of the primers should show the same or similar results. For example, primer 1445 is within a partition of the second cohort having a negative hybridization status, and thus primer 1445 can be identified as having a negative hybridization state, even though primer 1445 appears in a partition of the first cohort that has a positive hybridization status.

FIG. 21 is a flowchart of a method of determining a hybridization state of a primer for a mixture drop. Method 2100 can use features from other methods described herein. Method 2100 can be performed wholly or partly by a computer system.

At block 2110, a data signal obtained by a detector. The data signal includes signals from a plurality of partitions of a plurality of mixture drops. Each mixture drop can correspond to a cohort of partitions and including copies of at least one target nucleic acid. Each partition can include a plurality of primers.

At block 2120, a first cohort of partitions is identified as corresponding to a first mixture drop. This may be done as described herein.

At block 2130, it is determined that the first cohort of partitions corresponds to a first target nucleic acid. This may be done as described herein.

At block 2140, a hybridization status is determined of each partition of the first cohort based on the respective signal of the respective partition. The hybridization status of a partition can indicate whether at least one primer in the partition hybridized to the first target nucleic acid.

At block 2150, the primers in each partition of the first cohort are identified. A plurality of the partitions of the first cohort include a first primer.

At block 2160, it is determined whether the first primer is in any partitions of the first cohort having a negative hybridization status. In one embodiment, the first primer can be determined not to have hybridized to the first target nucleic acid when the first primer is in one or more partitions having a negative hybridization status. In another embodiment, the first primer can be determined not to have hybridized to the first target nucleic acid when the first primer is in at least a specified proportion of partitions having a negative hybridization status relative to partitions having a positive hybridization status. The propotion can be a percentage. For example, at least 5% or 10% of the partitions can be determined to have a negative hybridization status.

At block 2170, it is determined whether the first primer hybridized to the first target nucleic acid based on whether the first primer is in any partitions of the first cohort having a negative hybridization status. Other sets of partitions can be determine to correspond to the first target nucleic acid and these primers can be used to determine a nucleotide sequence of the first target nucleic acid.

D. Assembling Using Negative Primers

Once it is known which primers hybridize to a target nucleic acid, this first set of primers can be assembled to determine a nucleotide sequence of the target nucleic acid. In some embodiments, the knowledge of which primers do not hybridize can also be used in the assembly process. For example, the second set of primers that do not hybridize can be used to resolve ambiguities for where the first set of primers can align. Thus, a first primer (which does hybridize) can be determined not to align to a particular position in the nucleotide sequence, on the basis that a second primer (which does not hybridize) would align to the resulting sequence of the first primer was placed at the particular position.

FIG. 16 shows stages of an assembly process according to embodiments of the present invention. In stage 1, an unambiguous path is determined in an overlap graph. Various primers that hybridize to the target nucleic acid are shown overlapping with each other. These primers overlap with each other in an unambiguous manner.

In stage 2, an initial scaffold is created from the overlap graph. As one can see, the positions of the primers and their overlapping correspond to the initial scaffold. Dashes an initial scaffold referred to ambiguous positions where the specific nucleotide is not known.

As part of determining the initial scaffold, one can start with a seed and add primers that overlap with the seed. As the seed is extended, different possible nucleotides can be identified, which can correspond to ambiguous positions. Certain nucleotides can be excluded when the resulting nucleotide sequence would include a primer that did not hybridize. In this manner, an ambiguous position can be resolved. This process can be repeated to fill in the ambiguous positions identified with dashes.

After stage 2, ambiguous primers may remain. These ambiguous primers are ones that hybridize to the target nucleic acid, but might aligned to more than one location in the initial scaffold. These impious primers might fill in the ambiguous positions, but it is not known which of the alignment positions are correct. The primers that did not hybridize (negative primers) can be used to resolve the alignment position of the ambiguous primers.

In stage 3, the negative primers can be used to eliminate certain alignment positions of the ambiguous primers. In the example shown (which does not correspond to the initial scaffold in stage 2), and ambiguous primer #1 is shown as T-A-A-AGA, which could overlap with primer #2 TGATAA to form TGATAAAGA, but then the primer GATAAA should hybridize to the target nucleic acid. However, GATAAA does not hybridize to the target nucleic acid, and thus ambiguous primer #1 does not overlap with primer #2 (i.e., does not align to that particular position). Accordingly this particular alignment of the ambiguous primer can be excluded, thereby eliminating all incorrect alignment positions in leaving the correct alignment position.

In stage 4, a gap (example of ambiguous positions) can be filled in with positive primers that unambiguously align to the gap. An updated scaffold can thus be obtained. In stage 5, stages 3 and 4 can be repeated, where an updated scaffold is obtained at each iteration.

In stage 6, the final assembly can be compared to a reference sequence. In stage 7, negative primers can be used to confirm variant calls in the final assembly relative to the reference sequence.

FIG. 17 shows a diagram for confirming a variant call using negative primers. A reference sequence 1700 that corresponds to the target nucleic acid is shown. A first set of primers 1710 are positive primers that hybridize to the target nucleic acid. A second set of primers 1720 are negative primers that do not hybridize to the target nucleic acid.

The positive primers appear to show a variation relative to the reference sequence at position 1730. However, a portion 1712 of the primer 1710 could also align to ambiguous position 1740. However, if the two primers 1712 did align to ambiguous position 1740 then impious position 1740 would have a C. But, if ambiguous position 1740 data have a C, then negative primers 1722 would align to ambiguous position 1740. Therefore, it can be determined that the two primers 1712 cannot align to ambiguous position 1740. Thus, the two primers 1712 can be confirmed to align to position 1730, and add more confirming data that a variation does exist at position 1730.

FIG. 22 is a flowchart of a method 2200 of determining a nucleotide sequence of a target nucleic acid based on hybridization of primers according to embodiments of the present invention. Method 2200 can use features from other methods described herein. Method 2200 can be performed wholly or partly by a computer system.

At block 2210, data from an experiment involving hybridization of a plurality of primers to a target nucleic acid is received. The data can comprise positive hybridization and negative primer hybridization results. For example, some primers may hybridize to the target nucleic acid and some primers may not.

At block 2220, the data can be analyzed to identify a first cohort of primers as positively hybridizing to the target nucleic acid and a second cohort of primers as not hybridizing to the target nucleic acid.

At block 2230, a scaffold nucleotide sequence can be assembled based on the first cohort of primers. The scaffold nucleotide sequence can comprise unambiguous positions where a particular nucleotide is specified and ambiguous positions where a particular nucleotide is not specified. A first position can be identified as an ambiguous position based on determining that the first primer of the first cohort does not align to the first position of the scaffold nucleotide sequence.

At block 2240, at least one of said ambiguous positions can be resolved based on the second cohort of primers. In one embodiment, resolving a first ambiguous position can include determining that a first primer of the first cohort does not align to a first ambiguous position when such an alignment is consistent with a second primer of the second cohort also aligning to the first ambiguous position. For example, if aligning a positive primer to a position would create a sequence that a negative primer could align to, then the alignment of the positive primer can be determined to be wrong.

In another embodiment, resolving a first ambiguous position can include identifying one or more unambiguous primers of the first cohort by excluding alignment positions for the unambiguous primers based on the second cohort of primers. The one or more unambiguous primers of the first cohort can be used to determine one or more nucleotides at one or more ambiguous positions, thereby obtaining an updated scaffold nucleotide sequence.

In some embodiments, assembling the scaffold nucleotide sequence can includes determining that a first primer of the first cohort does not align to a first position of the scaffold nucleotide sequence when such an alignment is consistent with a second primer of the second cohort also aligning to the first position.

In one embodiment, a first subset of ambiguous primers can be identified. The first subset can be a subset of the first cohort of primers. An ambiguous primer can align to multiple positions in the updated scaffold nucleotide sequence. Alignment positions of a first ambiguous primer of the first subset can be excluded based on the second cohort of primers, thereby making the first ambiguous primer into a first unambiguous primer. The first unambiguous primer can be used to resolve a second ambiguous position in the updated scaffold nucleotide sequence.

II. Computer System

The above analysis can be performed in software on a computer or in a system as described herein. Any of the computer systems mentioned herein may utilize any suitable number of subsystems. Examples of such subsystems are shown in FIG. 23 in computer apparatus 10. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 23 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 977 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of instructions from system memory 72 or the storage device(s) 79 (e.g., a fixed disk, such as a hard drive or optical disk), as well as the exchange of information between subsystems. The system memory 72 and/or the storage device(s) 79 may embody a computer readable medium. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C# or scripting language such as Perl or Python using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary. The use of "or" is intended to mean an "inclusive or," and not an "exclusive or" unless specifically indicated to the contrary.

EXAMPLES

Example 1

One embodiment of the system was used to sequence a human DNA sample in a region of interest with a known mutation status. In the experiment, the region of interest was exon 15 of the BRAF gene.

Primer mixtures were designed such that each mixture contained six common 3' nucleotides (common region) and a mixture of 5' nucleotides. In total 4096 primer mixtures were designed with all possible 6 nucleotide common regions. The number of 5' nucleotides added in each primer mixture was optimized to keep Tm constant across the full set of 4096 mixtures as shown in FIG. 8. Each primer mixture (2 uM) was mixed with the following components: Thermopol buffer 1× (New England Biolabs), BSA 0.2 mg/ml (New England Biolabs), Inhibitor oligonucleotide 0.4 uM (3' Dabcyl labeled 20nt oligonucleotide-IDT), dTNP 0.2 uM (New England Biolabs), DNA amplicon 0.08 uM (to generate the amplicon exon 15 of the BRaf gene was PCR amplified using a FAM labeled forward PCR-primer which included a 5' sequence tag designed to hybridize to the Dabcyl quencher inhibitor, and a 5' phosphate-reverse PCR-primer), Lambda exonuclease 0.3 kU/ul (to facilitate conversion of the double stranded DNA amplicon to single strand), and BST 2.4 kU/ul (New England Biolabs). In addition, the following dyes (Columbia Biosciences) were added to each of the assay-primer-mixtures in 4096 unique combinations to facilitate identification of the primer-mixtures upon result-readout: Phycoerythrine (R-PE) (in one of 8 concentrations ranging from 0 to 6.7 ug/ml), R-PE conjugated Dylight 594 (in one of 8 dye concentrations, ranging between 0 to 9.6 ug/ml), R-PE conjugated Dylight 633 (in one of 8 concentrations ranging from 0.4 12.5), and R-PE conjugated Cy5.5 (in one of 8 dye concentrations, ranging from 0 to 13.3 ug/ml). Each primer-mixture was then emulsified into drops (water in oil emulsion as described in PCT Patent Publication No. WO2012/078710) and the drops from the full set of 4096 mixtures were mixed together and incubated at 34° C. for 30 minutes. Assay results were read out using an optical system as described in (PCT Patent Publication No. WO2012/135327 and WO2012/135201)

In several embodiments, the primer partitions contain more than one distinct primer. An example embodiment is depicted in FIG. 6A, and is referred to as a multiplexed primer partition. In this embodiment, the partition as a whole yields either a positive or negative binding signal, just as in the case of a single primer type per partition. The difference, however, is that the partition will only yield a negative result if all of the primers within the partition bind negatively, while the partition as a whole yields a positive result if any of the primers contained within positively binds. This dynamic is illustrated in FIG. 6B.

Assay-Primer-Multiplexing (up to 5 Primers Per Set)

One embodiment of the system was used to test various multiplexing strategies, including one strategy where 5 primers exist in each partition. Eight assay-primers were combined into 19 sets ranging between 1 to 5 assay-primers per set in a multi-well plate (2 uM concentration was used for each assay-primer added, ranging from 2 uM to 10 uM total for 1 to 5 assay-primers per set respectively). Each assay-primer set was then mixed with the following components: Thermopol buffer 1× (New England Biolabs), BSA 0.2 mg/ml (New England Biolabs), 0.4 uM Inhibitor oligonucleotide (a 3' Dabcyl labeled 20nt oligonucleotide-IDT), dTNP 0.2 uM (New England Biolabs), DNA amplicon 0.08 uM (to generate the amplicon exon 2 of the KRas gene was PCR amplified using a FAM labeled forward PCR-primer which included a 5' sequence tag designed to hybridize to the Dabcyl quencher inhibitor, and a 5' phosphate-reverse PCR-primer), Lambda exonuclease 0.3 kU/ul (to facilitate conversion of the double stranded DNA amplicon to single strand), and BST 2.4 kU/ul (New England Biolabs). In addition the following dyes (Columbia Biosciences) were added to each of the assay-primer-sets in unique combinations to facilitate identification of the assay-primer-sets upon result-readout: PE conjugated Dylight 594 (in one of 6 dye concentrations for each of the primer sets, ranging between 0 to 6.3 ug/ml), and PE conjugated Cy5.5 (in one of 4 dye concentrations for each of the primer sets, ranging from 0.8 to 6 ug/ml). Each assay-primer set mixture was then emulsified into drops (water in oil emulsion as described in PCT Publication No. WO2012/078710) and the drops from each of the 19 mixtures were mixed together and incubated at 37° C. for 30 minutes. Assay results were read out using an optical system as described in (PCT Patent Publication No. WO2012/135327 and WO2012/135201). Three of the eight primers were designed to hybridize to the DNA target (matched-assay-primers) and the other five did not have a complementary sequence within the DNA target (mis-matched-assay-primers).

Results:

Assay results are shown in FIG. 7A. Results are shown as standard deviation distance from the mis-matched-assay-primer signal ({[fluorescence]−[average fluorescence of mis-matched-assay-primers]}/[standard deviation mis-matched-assay-primers]). Combining assay-primers did not interfere with assay performance and results remained consistent throughout the primer-assay sets. Sets containing matched-assay-primers generated consistently high signal across all combinations and sets containing mis-matched-assay-primers generated consistent low signal regardless of the number of assay-primers included in the combined sets.

Assay-Primer-Multiplexing (up to 10 Primers Per Set)

Yet another embodiment of the system was used to test a multiplexing strategy where 10 primers were contained in each partition. Seventeen assay-primers were combined into 30 sets ranging from a single assay-primer to 10 combined assay-primers per set (2 uM concentration was used for each assay-primer, ranging from 2 uM to 20 uM total, for 1 assay-primer to 10 assay-primers per set respectively). The experiment performed was identical to the 5-primer-set experiment with the following exceptions:

Assay-primer-sets included up to 10 assay-primers each.

PE conjugated 594 dye was added to the assay-primer-sets in one of eight levels (ranging in concentration from 0 to 9.6 ug/ml), and the PE conjugated Cy5.5 was added to assay-primer-sets in one of six levels (ranging in concentration from 0.8 to 10.8 ug/ml) to generate the 30 unique identity dye "bar-codes" included in the experiment.

Results:

Assay results are shown in FIG. 7B. As with the 5 assay-primer set experiment combining assay-primers did not interfere with assay performance and results remained consistent throughout the primer-assay sets with sets containing matched-assay-primers generating consistently high signal across all combinations and sets containing mis-matched-assay-primers generating consistent low signal regardless of the number of assay-primers included in the combined sets.

Discussion:

The embodiments discussed in FIGS. 7A and 7B above contained either 5 or 10 distinct primers per multiplexed partition. Furthermore, all of the multiplexed partitions in those embodiments contained the same number of primers.

Other embodiments allow for as few as 2 primers per multiplexed partition or as many as 20 primers per multiplexed partition. Further embodiments also allow the partitions in the library to vary the number of primers they contain and any given partition is allowed to contain as few as 1 primer (and is therefore uniplex) to as many as 20 primers. In general, this allows the system's performance to be optimized around either empirical results of a primer vetting process or to answer a specific question about a sample. For instance, if a primer happens to yield poorer signal to background when multiplexed, we can supplement the partition library with a uniplex partition containing only that primer.

The embodiments used in the 5-plex and 10-plex experiments above placed each primer into multiple combinations of primers in different partitions. This is done primarily as an aid to the downstream deconvolution process (detailed below). Referring back to the example illustrated in FIG. 6B, if primer number 770, which is negative for the target, only belonged to partition "B", then we would not be able to rule it out as a false positive for that target since it would appear positive every time we encountered that target. Primer 770 needs to be given at least a second chance to yield its true negative result in the context of that target in order for its result to be correctly deconvolved from the results of its sister primers in partition "B".

Some embodiments place a strict constraint on the minimum number of multiplexed combinations that they must appear in. This minimum varies ranges from 2 to 20 between different embodiments and typically, but not necessarily, depends on the general degree of multiplexing in the library. For instance, one embodiment comprises a multiplexed partition library requiring that each primer appear in at least 10 different combinations of 10 primers each. Such an embodiment is an attempt to balance the probability that any single primer will be correctly deconvolved independent of the target sequence.

Still other embodiments further restrict the combinatorics of the partition library and require that no two combinations of primers contain more than a maximum number of primers in common. This maximum size of the intersection between two combinations can vary from between 1 to 4 among different embodiments. This maximum threshold varies independently of the degree of multiplexing in the library.

Other embodiments allow the combinations of primers within a partition to be randomly selected. Still others further allow the number of primers held in common between two partitions to be random. Yet other embodiments allow some of the primers to appear more than once (effectively at larger percentage of the total concentration) in the same partition. This last allowance helps to compensate for potential variation in binding efficiencies among the primers. For example, one embodiment allows for one primer in a 10-plex partition to comprise 50% of the total primer concentration allowed by the partition. This would leave enough primer concentration for an additional 5 primers at 10% concentration each, or two more primers at 25% concentration each. Some of the aforementioned embodiments that allow a variable number of primers per partition in the same library also vary the concentration allotments per primer in this manner. The percentage of total concentration allotted to any one primer within a partition may vary from as little as 0.4% up to as much as 100%.

Further embodiments place restrictions on the relationships among the sequences of the primers contained within a multiplexed partition. For instance, one embodiment does not allow any two primers within the same partition to overlap at their ends by more than some maximum number of nucleotides. This maximum number may vary from 1 to 8 among various embodiments. This is done primarily to avoid any contextual bias whether it is a function of hybridization kinetics, or inadvertently introduced by the many other library design parameters, or any other unforeseen source of contextual bias. Many embodiments place no such restrictions on the primers contained within partitions.

Much of the literature dealing with sequencing by hybridization is concerned with de novo assembly of targets. Of particular interest is the maximization of the complexity of targets that can be unambiguously assembled while constraining both the length and quantity of hybridization primers needed to resolve the sequence. The current invention is subject to similar constraints. As shown in Pevzner et. al., the upper limit on the length of sequence that can be unambiguously assembled from a collection of K-mers is 2K. For instance, setting K to equal 6, the current invention would need to have a primer library containing the full complement of 4096 hexamer sequences to unambiguously assemble targets with lengths no greater than 64 nucleotides.

In the embodiment detailed above, however, the 4096 hexamer primer sequences were used to sequence an amplicon that was over 100 nucleotides in length. This was possible because it was a not a de novo sequencing application. PCR primers were designed that captured and enriched for the region of interest. Those designs were based on wild type reference sequence taken from Genbank. This reference sequence was leveraged further downstream by the assembly and variant calling software modules to assemble a consensus sequence for the target (detailed below).

This type of reference-assisted assembly has also been studied in the literature (refs) and is often referred to as "re-sequencing" and the vast majority of so-called next generation sequencing applications follow this model. Reference-assisted assembly allows for a much more complex target to be elucidated with primers of a given length. It rests on the assumption that the majority of the target material will be similar to the reference sequence. The criteria then becomes the likelihood that a primer will align ambiguously to the reference sequence. In other words, the probability that a primer of a given length will have more than one exact sequence match in a target of a desired length.

For the embodiment used in the BRAF experiment, the full complement of hexamer probes was of greater overall complexity than necessary for a target of 100 bp since it was reference-assisted. The full complement of hexamers is sufficiently complex to re-sequence targets of up to 1 kilobase in length.

There are additional embodiments that allow for a number of designate bases that vary from as few as 4 nucleotides to as many as 24. Some of these embodiments have primers that all have the same number of designate bases, just as was done for the BRAF experiment.

Yet another embodiment allows the primers in the primer partition library to vary in their number of designate bases. For instance, in one embodiment, the partition library that contains the full complement of hexamers is supplemented with primers with a larger number of designate bases that yield the ability to span longer stretches of dinucleotide repeats (e.g. "ATATATATAT")(SEQ ID NO: 11)) or homopolymers (e.g. "TTTTTTTTTT") (SEQ ID NO: 12)). This can be done instead of the much more costly, but still feasible, embodiment of a partition library consisting of the full complement of 11-nucleotide sequences of designate bases. Embodiments that vary the number of designate bases among their primers may include the full range of between 4 and 24 designate nucleotides.

Some embodiments also make use of a technique that we refer to as "Tm normalization" or "Tm balancing" whereby degenerate bases are added to the 5' end of the oligo until that oligo's predicted melting temperature falls within an acceptable range. This is done because the microfluidic workflow subjects all of the primer partitions to the same thermal conditions during assay incubation. Some embodiments allow for oligo designs to have predicted Tm's that fall +/−20% outside of the universal thermal conditions for incubation. Other embodiments are more stringent and allow for as little as +/−5%. Yet another embodiment strives for balance within some range, e.g. +/−10%, but only for the majority of oligos. For example, in on embodiment, at least 70% of oligos must have Tm's that fall within +/−10% of target range while the remainder are designed to be as close as possible to the target range.

Additional embodiments allow primer oligos to have degenerate bases in locations other than merely the 5' end. This effectively introduces gaps or "wildcard" bases interspersed among the designate bases of the oligo. Examples of such "gapped primers" are illustrated in FIG. 15. These gapped primers allow the Assembly and Variant Calling software modules to resolve longer targets without having to increase the number of designate bases (detailed below). The number of gaps introduced thusly can vary in number between 1 and 6 and can be added to oligos with any number of designate bases between 4 and 24. Some embodiments contain mixtures of gapped primers and non-gapped primers in the same partition library. Some embodiments further vary the number of designate bases among the primers, both gapped and non-gapped. This confers the ability to tailor the content bias (or lack thereof) in potential sequencing contexts to the desired application. Some applications require a mixture of de novo sequencing elements as well as reference-assisted re-sequencing and may additionally require a very targeted assay of a known, singular event.

Example 2

Referring to the microfluidic schematic in FIG. 1, the point in the sequencing process where the software obtains its inputs is at the optical detector at point "E" in the microfluidic workflow. The inputs for the software take the form of images taken by the CCD sensor that is connected to the primary detection apparatus. The software processes the CCD images to locate the regions of the image that correspond to the primer partitions that are flowing past the detector. In one embodiment the software uses a watershed segmentation method to segment the image into regions corresponding to primer partitions. Alternate embodiments may use different image segmentation methods such as edge detection methods, blob detection methods, etc. It then extracts a spectral profile from each of the partition regions in the image.

In one embodiment the signal processing module then uses a generalized least squares method to perform a spectral decomposition on the partition fluorescence profile. This step produces a fluorescence intensity for each of the fluorescent dye components contained within the partitions. The barcode assignment module then uses these dye intensities to compute a normalized Euclidean distance to find the dye cluster that corresponds to the correct partition identity. The identity of the dye cluster is known before the experiment in some embodiments and a simple lookup of a grid position is used. In other embodiments the identity grid is fit to the dye clusters during the experiment using one of several grid fitting methods.

In the BRAF experiment detailed above, 4096 distinct dye barcode clusters existed and were found by the clustering method. In that embodiment the DBSCAN algorithm was used to cluster dye intensity vectors. Other embodiments use different variations of density based clustering methods as well as template matching methods where there is an expected map of dye cluster centroids established prior to the run. The dye clusters from the BRAF experiment are plotted in FIGS. 3A and 3B.

Example 3

Partition Assay Calling

FIG. 4A shows a plot of the raw assay intensities collected from the sequencing primer partitions used in the aforementioned BRAF experiment. These fluorescence intensities have not been normalized or otherwise translated in any way other than having been extracted from the spectral profile via generalized least squares decomposition.

It is clear from the figure that the two populations of partitions, assay-positive and assay-negative, are linearly separable. There are many methods available for partitioning two such populations. In this embodiment, a Naïve Bayesian classifier was used to determine which partitions were positive and which were negative. A small, random subset of the raw assay intensities were used as a training set for the classifier. In this embodiment, 20% of the partitions were used as the training set. In other embodiments, the training set represents a different percentage and can be as low as 5% or as much 50%.

FIG. 4B calls out the robustness of the assay with respect to degenerate bases. The figure contains the same scatter plot found in FIG. 4A. In this figure, however, the clusters that correspond to partitions that contain primers with exactly 3 degenerate bases are singled out. The remainder of the partitions captured by this scatter plot contain primers that have fewer than 3 degenerate bases and range from zero to 2 degenerate bases. This is to demonstrate that in the worst case, there is no correlation between the number of degenerate bases and the resulting assay intensity for primers in either the positive or negative binding states.

Temporal Segmentation

From the perspective of the Barcode Identifier and Assay Caller modules depicted in FIG. 2, a continuous stream of primer partition images are observed. There is no explicit boundary in time that demarcates the end of one PCR-partitions-worth of primer partitions and the beginning of the next. This temporal association must be derived from the primary data (i.e. the stream of primer identities and assay calls).

FIG. 9 illustrates this process that will be referred to as temporal segmentation. To accomplish this a rate of self-contradiction is tracked as a function of time within a sliding window of partitions. For instance, in the embodiment that was used to sequence the BRAF target a sliding window of 2400 primer partitions was checked to see how many of the primer partitions that were observed more than once actually contradicted themselves with respect to their assay state. That rate is plotted as a function of time in FIG. 9. The rate naturally displays a series of local minima and maxima. The local minima are the estimates of the temporal boundaries between each PCR-partitions-worth of primer measurements. In FIG. 9, the vertical bars mark the local minima and thereby the PCR partition boundaries in time. In one embodiment, once a set of primer partitions are associated in time by this module, it remains in place for the remainder of the analysis process. In other embodiments, the association is allowed to be broken if a stronger hypotheses can be generated by swapping primer partitions at the temporal boundaries.

Example 4

Clustering of Partition Sets

The design of the software system is such that it can support a set of related assumptions that any given set of primer partition measurements that is taken of a particular PCR partitions is:

a) not guaranteed to be a complete sampling of the entire primer partition library
b) not guaranteed to come in any particular order
c) not guaranteed to repeat itself exactly the next time that amplicon (i.e., target nucleic acid) is measured
d) in the general case there will be multiple PCR partitions in the PCR partition library that target the same regions of interest in the sample.

Given these assumptions, the software design enables a complete picture of not only the amplicon, but also of sub-populations of allelic variants within a sample to be accumulated over time. This is accomplished by identifying the most likely genomic region of interest that corresponds to the set of measurements at hand. We refer to the process of identifying the reference sequence corresponding to the amplicon as mapping.

The mapping process begins before the sequencing run begins by building a lookup table with one entry per reference sequence in the panel of amplicons being targeted. The identification process is performed via a simple scoring mechanism whereby each reference sequence for each region of interest in the panel is assigned a scoring vector, with one element per partition in the primer partition library. Each vector is initialized to contain a one (1) where the corresponding partition is expected to yield a positive binding event, and a zero (0) where the corresponding partition is expected to yield a negative. Such a table is illustrated in FIG. 10.

When the next set of partition measurements comes through the software system, that set of measurements is converted to a vector with structure identical to those assigned to each reference sequence. The vector elements are similarly initialized to one (1) where a positive was encountered and a zero (0) otherwise.

This measurement vector is then compared against each of the reference vectors and a score is determined. In one embodiment a Hamming distance is calculated between the bits in each vector corresponding to the primer partitions observed in the current temporally segmented set. The reference sequence that shows the maximum score is chosen as the most likely region of origin, and that set of measurements is assigned to it for future steps in the analysis workflow. This scoring process is illustrated in FIG. 11.

Other embodiments use alternate reference sequence lookup tables including table entries that include counts of primer instances in the reference sequence. Further embodiments included secondary tables and indices into the original reference lookup table that have precomputed distance metrics to particular subsets of reference table entries. These secondary indices allow for faster lookup times during the mapping process.

In another embodiment, a variant of the same identification method is provided to accomplish the analogous task in de novo applications where reference sequences do not exist. This variant of the method is depicted in FIG. 12. In this embodiment, the table of reference vectors is built up dynamically during the course of a run. The vectors are initialized by the same rules as for any set of primer partition measurements. Each new set of measurements is compared with all previous sets of measurements. The scoring metric could be the same Hamming distance as used above, but in this case it is used as a distance metric for the purposes of agglomerative clustering of measurements (refs for agglomerative clustering).

We refer to the set of all measurements associated with a particular reference sequence or measurement centroid as a "read stack", borrowing from the vernacular of the so-called next generation sequencing field. Once all of the measurements have been taken for a sample, further clustering can be performed within a read stack to identify distinct allelic sub-populations. This sub-clustering process uses the same scoring mechanism as was used in the agglomerative clustering step used in the de novo case above.

It should be clear from the figures that all of the mapping and clustering steps can take place without having to deconvolve the primers that are contained within each of the multiplexed partitions. This is a useful capability given that there may be strict constraints on compute resources and running time, depending on the application. It is highly advantageous, from the standpoint of efficiency, to be able to get through as much of the analysis work flow as possible prior to deconvolution.

Example 5

Negative Evidence and Deconvolution of Multiplexed Partitions

Negative evidence is leveraged by the analysis software in several ways during analysis. The utility of negative data in the mapping process was discussed above in the context of computing an appropriate mapping score. However, during the mapping and clustering processes, negative data remains at the granularity of a partition, not a particular primer, for the purpose of efficiency. There are further uses of negative evidence, including those at the finer granularity of individual primers.

As described above during the primer selection process, the multiplexing of primers within partitions naturally, but only temporarily, introduces artificial false positives. Using the examples from FIG. 6B, exactly 9 false positives primers are introduced at the time when partition "A" is measured by the primary detector. Ideally, all 9 of these false positives will be eliminated from consideration without affecting the final variant calls and allele counts for the sample at hand. This is accomplished by leveraging the true negative evidence obtained from the wholly negative partitions, that is to say from the partitions where every primer therein was negatively hybridized to the target amplicon. The true negatives are used to negate the false positives, i.e., primers that do not actually hybridize but are in partitions with at least one hybridizing primer.

In order to be able to perform this negation properly, there must be a correct association that exists between wholly positive and wholly negative partitions that correspond to the same events in the sample, i.e. either the same clonal population for an amplicon or the same allele.

Since primers within a partition have no means by which to cancel one another's positivity, the analysis software uses other partitions that were measured at different times during the run. This requires that the software associate partition measurements with the same endogenous instances of amplicons (i.e. measurements taken from the same PCR-partition) as well as between instances of the same allelic variant.

The first type of association, between measurements of the same particular clonal population, is performed by the aforementioned temporal segmentation process depicted in FIG. 9. Once this is done for a set of primer partition measurements, they form a grouping referred to herein as a "cohort," an association that remains unbroken throughout the remainder of the analysis process. This association allows us to use the primers known to reside in the wholly negative partitions as countermeasures for the false positives introduced by the wholly positive partitions. This process is illustrated in FIG. 13. Each of the primers from the negative partitions effectively negates the false positive instances of the matching primer found in a positive partition.

The second type of association, between cohorts representing the same amplicon or allele, is performed by the mapping and clustering processes described above and in FIGS. 10, 11 and 12. The negation process is the same as in the intra-cohort analog depicted in FIG. 13. However, in this case, negative primers taken from one set of partitions are allowed to negate their matching primer instances who are members of positive primer partitions in other sets. This type of negation is illustrated in FIG. 14.

It is expected that a cohort may represent a small enough random sample of the larger partition library that we are not guaranteed to observe a matching negative primer for every false positive introduced by the positive partitions. In such cases, the first type of association yields an incomplete deconvolution for that cohort. The second type of association, between cohorts, can be guaranteed to compensate for this potential lack of countermeasures to an extent that yields sufficiently accurate variant calls. The method can guarantee this by increasing the number of PCR-partitions in the PCR partition library that represent any region of interest. That is to say, increase the expected number of repeated measurements of the same region of interest. This is analogous to the notion of "coverage depth" in the literature. In essence, the system gives itself more chances to observe the negative counterparts to previous false positive measurements by setting the coverage depth to appropriate level. This capability simply expands the number of sets of partition measurements that we can draw from in order to perform the inter-set negation detailed in FIG. 14.

This is a useful capability of the system: the ability to postpone the deconvolution of its own false positive measurements to a later stage of the process by way of association of sets of primer partition measurements either directly to one another via clustering (the de novo case) or indirectly via mapping to a reference, wild type sequence.

Example 6

Variant Call and Assembly

After any multiplexed partitions have been deconvolved and all of the sets of primer partitions have either been clustered to one another or against a reference sequence, the next stage of the analysis process is to invoke the Assembly software module and call variants.

In the BRAF experiment detailed above, the relevant embodiment was targeting a reference-assisted re-sequencing application of the technology. As such, a reference sequence was leveraged in the assembly of a consensus of the target sequence. This process is illustrated in FIG. 5.

FIG. 5 depicts the reference-assisted assembly process that was performed by the assembly software for an amplicon representing exon 15 of the BRAF gene. The wild type sequence "D" was used as the reference for the comparative assembly process. In the figure, only a subsequence of the full reference sequence is depicted. The sets of primers that yielded positive assay calls, sets "A" and "E" were used to initialize the hypothesis space of potential mutations with respect to the wild type. Positive primer "G" was found to align to the reference sequence at the location near set "E" within an edit distance of 1 while aligning at the location near set "A" with a larger edit distance of 2. However, the hypothesis that is generated by the consensus of set "A" was found by the software to have a much higher likelihood of being correct. The software used both the positive set "E" combined with the negatively binding primers of set "H" to form a consensus in that region of the reference that matches the wildtype and with far higher likelihood of being correct than the G/A mismatch hypothesized by primer "G". The final consensus sequence that was called for this target is listed in sequence "I" and contains the correctly called 2-nucleotide substitution mutation from the sample as corroborated through the Sanger sequencing method. This illustrates the basic steps of the reference assisted assembly; look for alignments against the reference sequence for every primer within some edit distance threshold, use the overlap relationships with other positive and negative primers to rank the candidate alignments and do this for every base position in the reference sequence, then choose the maximum likelihood hypotheses at every position of the reference. If any primers are left outside of the final collection of winning hypothetical consensus sequences, then they are compared with other primers to attempt a reference-free assembly of a potential insert with respect to the reference.

In a de novo application, the clustered primer partition sets are fed into the Assembly module. The assembly process is illustrated in FIG. 16. In this illustration a general embodiment of a primer partition library that contains primer sequences that adhere to a mixture of gapping schemes is assumed.

In one embodiment, the first stage of the process is to find an initial scaffold to be filled out in later stages of the process. This stage is accomplished using a De Bruijn graph traversal method similar to the approach taken by the Velvet assembler. Primers with a negative assay state, or "negative evidence" are used to counter spurious branch points or edges in the De Bruijn graph during this stage. In one embodiment, only edges that have no contradictions in the negative evidence are allowed to remain in the graph. In other embodiments, the confidence score for the assay call underlying a negative primer (obtained from the Assay Calling module) is taken into account.

In the same embodiment depicted in FIG. 16, the next stage of the process attempts to fill in any gaps in the initial scaffolds. Again, negative evidence is leveraged to counter any potentially false filler. Again, no primer is allowed to fill a gap if the consensus formed by the act of merging the sequences results in a contradiction with any negative evidence. This gap filling process is iterative and order dependent, meaning that the number of iterations required may depend on the order in which primers are selected to fill in gaps. A primer that is ambiguous at in one iteration may be unambiguous with respect to a later version of the evolving assembly.

Finally, once all of the positive primers have been exhausted either by contributing to the assembly or having been unavoidably countered by negative evidence, the final assembly is reported in the data readout. If a reference sequence was provided, the final assembly is compared to that reference using a pairwise alignment method, such as the Smith-Waterman method, to find hypothetical variants with respect to that reference. If, in this case, variants are found, the negative evidence can be used as a counterweight to those potential variants just as it was applied in the comparative re-sequencing process above.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for determining a nucleotide sequence in a target nucleic acid, the method comprising,
providing a plurality of partitions, the partitions comprising a set of two or more different primers and a target nucleic acid, wherein different partitions contain different sets of primers with a majority of primers in the sets being common with a different primer set but wherein any two different partitions having a common primer contain no more than one common primer; and
hybridizing the target nucleic acid to the primers in the reaction partitions under conditions in which fully complementary primers hybridize to the target sequence and primers that are not fully complementary do not hybridize to the target nucleic acid.

2. The method of claim 1, wherein the sets of primers comprise primers of at least 2, 3, or 4 different number of designated nucleotides over 4 nucleotides.

3. The method of claim 1, wherein at least 100 partitions are provided and each of the 100 partitions contain a different set of primers.

4. The method of claim 1, wherein the target nucleic acid is an amplicon.

5. The method of claim 1, wherein the target nucleic acid comprises a fluorescent moiety and is annealed to a quenching oligonucleotide that comprises a quencher, wherein annealing of the quencher to the target nucleic acid quenches fluorescence of the fluorescence moiety.

6. The method of claim 5, further comprising detecting presence or absence of primer hybridization to the target nucleic acid in the partitions, wherein the detecting comprises contacting the target nucleic acid annealed to the quencher oligonucleotide with a primer-dependent polymerase, wherein extension of the primers, if hybridized, results in displacement of the quencher oligonucleotide, thereby generating a fluorescent signal.

7. The method of claim 6, wherein the partitions comprise multiple primers having different sequences, and
wherein the detecting comprises:
detecting the presence or absence of the fluorescent signal, wherein presence of the fluorescent signal indicates that one of the multiple primers hybridized to the target nucleic acid and lack of the fluorescent signal indicates none of the multiple primers hybridized to the target nucleic acid; and
the method further comprises deconvoluting the nucleotide sequence of the target nucleic acid based on the presence or absence of the fluorescent signal and the sequences of the primers.

8. The method of claim 1, wherein the partitions contain one or more spectroscopic substances that coincide with particular primers in the partition such that the sequences of the primers in the partition is determinable by detection of a spectroscopic characteristic of the partition and wherein the determining further comprises detecting the spectroscopic characteristic and correlating the spectroscopic characteristic to the sequences of the primers.

9. The method of claim 1, wherein n number of sets of primers are present in n partitions, with different partitions containing different sets of primers, wherein different sets of primers have 2-20 different unique primers and different partitions have no more than one primer in common, wherein n is between 1000-300,000.

10. The method of claim 9, wherein partitions for each of the n sets contain one or more spectroscopic substances such that each of the n sets can be distinguished by a spectroscopic characteristic.

11. The method of claim 1, wherein no two primers in a partition has a sequence overlap of greater than two nucleotides.

12. The method of claim 1, wherein some of the primers in the sets have 6-18 designated nucleotides.

13. The method of claim 1, wherein the designated nucleotides are contiguous.

14. The method of claim 1, wherein at least some of the designated nucleotides are non-contiguous such that at least two of the designated nucleotides are separated by at least one degenerate nucleotide position or universal nucleotide.

15. The method of claim 1, wherein between 400-16000 primers of different sequence occur in the partitions.

16. The method of claim 1, wherein the target nucleic acid is between 50-1000 nucleotides long.

17. The method of claim 1, wherein the target nucleic acid comprises a 3' stem loop.

18. The method of claim 1, wherein the partitions are drops.

19. The method of claim 18, wherein the drops are contained in an emulsion.

20. The method of claim 1, further comprising, detecting presence or absence of primer hybridization to the target nucleic acid in the partitions, wherein a partition yields an assay-negative call if and only if all of the primers contained therein negatively hybridize;
determining which primers in the series bind to the target nucleic acid; and determining the nucleotide sequence in a target nucleic acid based on which primers bind to the target nucleic acid.

21. The method of claim 1, further comprising combining (i) target partitions comprising the target nucleic acid with (ii) primer partitions on a one-for-one basis to form the partitions.

22. The method of claim 1, wherein the two or more different primers have at least 4 designated nucleotides, with other nucleotide positions of the primers, if any, being degenerate positions or universal nucleotides.

* * * * *

SEQUENCE LISTING

<160> NUMBER OF SEQ ID NOS: 12

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: synthetic positive primer "G"

<400> SEQUENCE: 1
cagtaaaaat a                                                            11

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: synthetic primer "C"

<400> SEQUENCE: 2
ctacagagaa at                                                           12

<210> SEQ ID NO 3
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: synthetic wild-type BRAF exon 15 amplicon
      reference subsequence "D"

<400> SEQUENCE: 3
acagtaaaaa taggtgattt tggtctagct acaatgaaat ctcgatggag tgggtcccat        60
cagt                                                                    64

<210> SEQ ID NO 4
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: synthetic final consensus target sequence "I"

<400> SEQUENCE: 4
acagtaaaaa taggtgattt tggtctagct acagagaaat ctcgatggag tgggtcccat        60
cagt                                                                    64

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: synthetic wild-type reference sequence 1000,
      reference sequence 1400, stage 6 final assembly

```
<400> SEQUENCE: 5
tagctatgac gtagggtact tagatgctga ccgttagc                              38

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: synthetic target molecule

<400> SEQUENCE: 6
aatgggtagg gggggtataa ttgagagaga tgaggtgt                              38

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: synthetic stage 2 initial scaffold, assembly
      scaffold, initial target scaffold sequence
<220> FEATURE:
<221> NAME/KEY: modified_base
<222> LOCATION: (2)..(2)
<223> OTHER INFORMATION: a, c, t, or g
<220> FEATURE:
<221> NAME/KEY: modified_base
<222> LOCATION: (4)..(4)
<223> OTHER INFORMATION: a, c, t, or g
<220> FEATURE:
<221> NAME/KEY: modified_base
<222> LOCATION: (8)..(8)
<223> OTHER INFORMATION: a, c, t, or g
<220> FEATURE:
<221> NAME/KEY: modified_base
<222> LOCATION: (10)..(10)
<223> OTHER INFORMATION: a, c, t, or g
<220> FEATURE:
<221> NAME/KEY: modified_base
<222> LOCATION: (12)..(12)
<223> OTHER INFORMATION: a, c, t, or g
<220> FEATURE:
<221> NAME/KEY: modified_base
<222> LOCATION: (16)..(16)
<223> OTHER INFORMATION: a, c, t, or g
<220> FEATURE:
<221> NAME/KEY: modified_base
<222> LOCATION: (18)..(18)
<223> OTHER INFORMATION: a, c, t, or g
<220> FEATURE:
<221> NAME/KEY: modified_base
<222> LOCATION: (20)..(20)
<223> OTHER INFORMATION: a, c, t, or g
<220> FEATURE:
<221> NAME/KEY: modified_base
<222> LOCATION: (24)..(24)
<223> OTHER INFORMATION: a, c, t, or g
<220> FEATURE:
<221> NAME/KEY: modified_base
<222> LOCATION: (26)..(26)
<223> OTHER INFORMATION: a, c, t, or g
<220> FEATURE:
<221> NAME/KEY: modified_base
<222> LOCATION: (28)..(28)
<223> OTHER INFORMATION: a, c, t, or g
<220> FEATURE:
<221> NAME/KEY: modified_base
<222> LOCATION: (32)..(32)
<223> OTHER INFORMATION: a, c, t, or g
<220> FEATURE:
```

```
<221> NAME/KEY: modified_base
<222> LOCATION: (34)..(34)
<223> OTHER INFORMATION: a, c, t, or g
<220> FEATURE:
<221> NAME/KEY: modified_base
<222> LOCATION: (36)..(36)
<223> OTHER INFORMATION: a, c, t, or g

<400> SEQUENCE: 7
antnggtngn gnggnanan ttgngngnga tnangngt                             38

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: synthetic stage 7 reference sequence (optional)
<220> FEATURE:
<221> NAME/KEY: modified_base
<222> LOCATION: (23)..(23)
<223> OTHER INFORMATION: a, c, t, or g

<400> SEQUENCE: 8
aatgggtagg gtgggtataa ttnagagaga tgaggtgt                            38

<210> SEQ ID NO 9
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: synthetic reference sequence 1700, target
      nucleic acid, wild-type or "reference" allele
<220> FEATURE:
<221> NAME/KEY: modified_base
<222> LOCATION: (36)..(36)
<223> OTHER INFORMATION: a, c, t, or g

<400> SEQUENCE: 9
aaaaacaacc gagctccgac ggattttgt tcgcantttt gtatat                    46

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: synthetic primer

<400> SEQUENCE: 10
attttaactt                                                          10

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: synthetic primer partition library supplemental
      dinucleotide repeat primer

<400> SEQUENCE: 11
```

```
atatatatat                                                                  10

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: synthetic primer partition library supplemental
      homopolymer primer

<400> SEQUENCE: 12
tttttttttt                                                                  10
```